US012692320B2

(12) United States Patent
Ahmadi et al.

(10) Patent No.: US 12,692,320 B2
(45) Date of Patent: *Jul. 28, 2026

(54) BISPECIFIC ANTIBODIES AGAINST CD3 AND CD20

(71) Applicant: GENMAB A/S, Valby (DK)

(72) Inventors: Tahamtan Ahmadi, Rydal, PA (US);
Manish Gupta, Skillman, NJ (US);
Tommy R. Li, Edison, NJ (US);
Roberto Oliveri, Copenhagen (DK);
Dena DeMarco, Chatham, NJ (US);
Ida Hiemstra, Utrecht (NL);
Christopher Chiu, Warren, NJ (US);
Brian Elliott, Hoboken, NJ (US); Ada Azaryan, North Bethesda, MD (US)

(73) Assignee: GENMAB A/S, Valby (DK)

( * ) Notice: Subject to any disclaimer, the term of this patent is extended or adjusted under 35 U.S.C. 154(b) by 738 days.

This patent is subject to a terminal disclaimer.

(21) Appl. No.: 17/923,317

(22) PCT Filed: May 7, 2021

(86) PCT No.: PCT/EP2021/062231
§ 371 (c)(1),
(2) Date: Nov. 4, 2022

(87) PCT Pub. No.: WO2021/224499
PCT Pub. Date: Nov. 11, 2021

(65) Prior Publication Data
US 2023/0227570 A1 Jul. 20, 2023

Related U.S. Application Data

(60) Provisional application No. 63/022,212, filed on May 8, 2020, provisional application No. 63/078,667, filed on Sep. 15, 2020, provisional application No. 63/121,690, filed on Dec. 4, 2020.

(51) Int. Cl.
| | |
|---|---|
| *C07K 16/28* | (2006.01) |
| *A61K 31/573* | (2006.01) |
| *A61K 39/00* | (2006.01) |
| *A61K 39/395* | (2006.01) |
| *A61K 45/06* | (2006.01) |
| *A61P 35/00* | (2006.01) |

(52) U.S. Cl.
CPC ........ *C07K 16/2887* (2013.01); *A61K 31/573* (2013.01); *A61K 39/3955* (2013.01); *A61K 45/06* (2013.01); *A61P 35/00* (2018.01); *C07K 16/2809* (2013.01); *A61K 39/00* (2013.01); *A61K 2039/505* (2013.01); *A61K 2039/545* (2013.01); *C07K 2317/21* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 4,946,778 | A | 8/1990 | Ladner et al. |
| 5,589,466 | A | 12/1996 | Felgner et al. |
| 5,731,168 | A | 3/1998 | Carter et al. |
| 5,736,137 | A | 4/1998 | Anderson et al. |
| 5,739,277 | A | 4/1998 | Presta et al. |
| 5,973,972 | A | 10/1999 | Kwon et al. |
| 6,077,835 | A | 6/2000 | Hanson et al. |
| 7,262,028 | B2 | 8/2007 | Van Berkel et al. |
| 7,375,118 | B2 | 5/2008 | Sircar et al. |
| 7,612,181 | B2 | 11/2009 | Wu et al. |
| 7,951,918 | B2 | 5/2011 | Glaser et al. |
| 8,236,308 | B2 | 8/2012 | Kischel et al. |
| 9,150,663 | B2 | 10/2015 | Labrijn et al. |
| 9,212,230 | B2 | 12/2015 | Schuurman et al. |
| 10,273,227 | B2 | 4/2019 | Kettle et al. |
| 10,344,050 | B2 | 7/2019 | Gramer et al. |
| 10,407,501 | B2 | 9/2019 | Van Den Brink et al. |
| 10,465,006 | B2 | 11/2019 | Van Den Brink et al. |
| 10,544,220 | B2 | 1/2020 | Engelberts et al. |
| 10,590,206 | B2 | 3/2020 | Labrijn et al. |
| 10,597,464 | B2 | 3/2020 | Labrijn et al. |
| 10,882,907 | B2 | 1/2021 | Rehder et al. |
| 10,906,991 | B2 | 2/2021 | Schuurman et al. |
| 11,180,572 | B2 | 11/2021 | De Jong et al. |

(Continued)

FOREIGN PATENT DOCUMENTS

| | | |
|---|---|---|
| CN | 101309703 A | 11/2008 |
| CN | 102250246 A | 11/2011 |

(Continued)

OTHER PUBLICATIONS

Lugtenburg et al. First-in-Human, Phase 1/2 Trial to Assess the Safety andClinical Activity of Subcutaneous GEN3013 (DuoBody (R)-CD3xCD20) in B-Cell Non-Hodgkin Lymphomas. (Blood (2019) 134 (Supplement_1) (Year: 2019).*
NCT03625037 (Viewing V3 (Sep. 13, 2018)). First-in-Human (FIH) Trial in Patients With Relapsed, Progressive or Refractory B-Cell Lymphoma (EPCORE™ NHL-1) (Year: 2018).*
Withoff, S. et al., Characterization of BIS20x3, a bi-specific antibody activating and retargeting T-cells to CD20-positve B-cells,: British Journal of Cancer, vol. 84(8):1115-1121 (2001).
Committee for Medicinal Products for Human Use (CHMP), "Guideline on the evaluation of anticancer medicinal products in man," European Medicines Agency, Science Medicines Health, EMA/CHMP/205/95 Rev.5, Sep. 22, 2017, 43 pages.

(Continued)

*Primary Examiner* — Maher M Haddad
(74) *Attorney, Agent, or Firm* — Nelson Mullins Riley & Scarborough LLP; Jane E. Remillard, Esq.; Christopher L. Frank

(57) ABSTRACT

The present invention relates to bispecific antibodies (bs-Abs) and the use of such antibodies in the treatment of disease in subjects. Moreover, advantageous treatment regimens are provided for the treatment of B-cell Non-Hodgkin Lymphoma (B-NHL).

31 Claims, 7 Drawing Sheets

Figure 1:
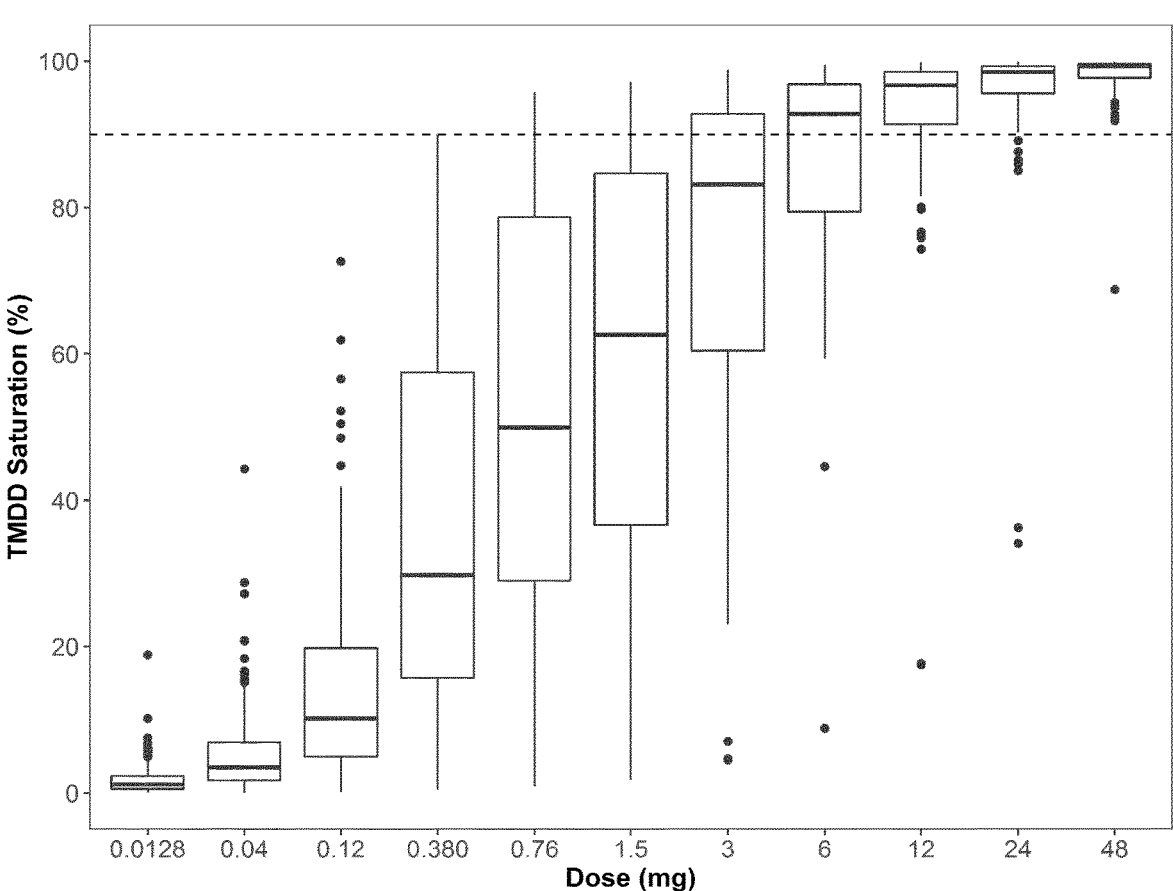

Specification includes a Sequence Listing.

(56)          References Cited

U.S. PATENT DOCUMENTS

| | | | |
|---|---|---|---|
| 11,359,015 B2 | 6/2022 | Rademaker et al. | |
| 11,485,796 B2 | 11/2022 | Labrijn et al. | |
| 11,492,371 B2 | 11/2022 | Gramer et al. | |
| 11,535,679 B2 * | 12/2022 | Elliott | C07K 16/468 |
| 11,548,952 B2 * | 1/2023 | Elliott | A61K 31/7068 |
| 11,608,383 B2 * | 3/2023 | Elliott | A61P 35/02 |
| 11,613,575 B2 | 3/2023 | Van Den Brink et al. | |
| 11,845,805 B2 * | 12/2023 | Elliott | A61K 31/573 |
| 11,858,995 B2 * | 1/2024 | Elliott | C07K 16/468 |
| 11,866,514 B2 | 1/2024 | Labrijn et al. | |
| 12,415,859 B2 | 9/2025 | Alfonso Martin et al. | |
| 12,435,154 B2 * | 10/2025 | Ahmadi | A61K 31/135 |
| 2004/0167319 A1 | 8/2004 | Teeling et al. | |
| 2010/0015513 A1 | 1/2010 | Nakahama et al. | |
| 2010/0105874 A1 | 4/2010 | Schuurman et al. | |
| 2010/0155133 A1 | 6/2010 | Makwinski et al. | |
| 2010/0297106 A1 | 11/2010 | Sloey et al. | |
| 2011/0275787 A1 | 11/2011 | Kufer et al. | |
| 2012/0301400 A1 | 11/2012 | Williams et al. | |
| 2013/0039913 A1 | 2/2013 | Labrijn et al. | |
| 2013/0216556 A1 | 8/2013 | Fowler et al. | |
| 2014/0088295 A1 | 3/2014 | Smith et al. | |
| 2014/0112914 A1 | 4/2014 | Nezu et al. | |
| 2014/0303356 A1 | 10/2014 | Gramer et al. | |
| 2015/0071943 A1 | 3/2015 | Bishop et al. | |
| 2015/0166661 A1 | 6/2015 | Chen et al. | |
| 2015/0175707 A1 | 6/2015 | De Jong et al. | |
| 2015/0209430 A1 | 7/2015 | Benedict et al. | |
| 2015/0225479 A1 | 8/2015 | Huille et al. | |
| 2015/0337049 A1 | 11/2015 | Labrijn et al. | |
| 2016/0046727 A1 | 2/2016 | Labrijn et al. | |
| 2016/0159330 A1 | 6/2016 | Anderson et al. | |
| 2016/0159930 A1 | 6/2016 | Schuurman et al. | |
| 2016/0168247 A1 | 6/2016 | Van Den Brink et al. | |
| 2016/0199399 A1 | 7/2016 | Knudsen | |
| 2016/0333095 A1 | 11/2016 | Van Den Brink et al. | |
| 2017/0233497 A1 | 8/2017 | Labrijn et al. | |
| 2017/0349657 A1 | 12/2017 | Saville et al. | |
| 2017/0355767 A1 | 12/2017 | Engelberts et al. | |
| 2018/0134798 A1 | 5/2018 | Chu et al. | |
| 2019/0284278 A1 | 9/2019 | Rademaker et al. | |
| 2020/0048304 A1 | 2/2020 | Gramer et al. | |
| 2020/0123255 A1 | 4/2020 | Van Den Brink et al. | |
| 2020/0190200 A1 | 6/2020 | Alfonso Martin et al. | |
| 2020/0199229 A1 | 6/2020 | Van Den Brink et al. | |
| 2020/0199231 A1 | 6/2020 | Engelberts et al. | |
| 2020/0262932 A1 | 8/2020 | Labrijn et al. | |
| 2020/0332022 A1 | 10/2020 | Labrijn et al. | |
| 2021/0032358 A1 | 2/2021 | Valbjoern et al. | |
| 2021/0230301 A1 | 7/2021 | De Jong et al. | |
| 2021/0371538 A1 | 12/2021 | Ahmadi et al. | |
| 2022/0088070 A1 | 3/2022 | Albertson et al. | |
| 2022/0112287 A1 | 4/2022 | Elliott et al. | |
| 2022/0112300 A1 | 4/2022 | Elliott et al. | |
| 2022/0112301 A1 | 4/2022 | Elliott et al. | |
| 2022/0112309 A1 | 4/2022 | Elliott et al. | |
| 2022/0119544 A1 | 4/2022 | Elliott et al. | |
| 2022/0144964 A1 | 5/2022 | Elliott et al. | |
| 2022/0380464 A1 | 12/2022 | Rademaker et al. | |
| 2022/0389101 A1 | 12/2022 | Rademaker et al. | |
| 2022/0411505 A1 | 12/2022 | Valbjoern et al. | |
| 2023/0027394 A1 | 1/2023 | Rademaker et al. | |
| 2023/0227495 A1 | 7/2023 | Gramer et al. | |
| 2023/0227570 A1 | 7/2023 | Ahmadi et al. | |
| 2023/0241211 A1 | 8/2023 | Chiu et al. | |
| 2023/0303693 A1 | 9/2023 | Chiu et al. | |
| 2023/0310599 A1 | 10/2023 | Benonisson et al. | |
| 2023/0312757 A1 | 10/2023 | Elliott et al. | |
| 2023/0312758 A1 | 10/2023 | Elliott et al. | |
| 2023/0312759 A1 | 10/2023 | Elliott et al. | |
| 2023/0322947 A1 | 10/2023 | Labrijn et al. | |
| 2023/0355753 A1 | 11/2023 | Elliott et al. | |
| 2023/0357440 A1 | 11/2023 | Elliott et al. | |
| 2023/0374131 A1 | 11/2023 | Van Den Brink et al. | |
| 2024/0034812 A1 | 2/2024 | Elliott et al. | |
| 2024/0174761 A1 | 5/2024 | Elliott et al. | |
| 2024/0209117 A1 | 6/2024 | Labrijn et al. | |
| 2024/0301078 A1 | 9/2024 | Elliott et al. | |
| 2024/0368297 A1 | 11/2024 | Li et al. | |
| 2024/0400685 A1 | 12/2024 | Hibbert et al. | |
| 2024/0409656 A1 | 12/2024 | Kilavuz et al. | |
| 2025/0101102 A1 | 3/2025 | Chiu et al. | |
| 2025/0115665 A1 | 4/2025 | Chiu et al. | |
| 2025/0304689 A1 | 10/2025 | Elliott et al. | |

FOREIGN PATENT DOCUMENTS

| | | |
|---|---|---|
| CN | 1729203 B | 2/2014 |
| CN | 103796677 B | 5/2014 |
| CN | 104271122 A | 1/2015 |
| CN | 104922668 A | 9/2015 |
| CN | 104922688 A | 9/2015 |
| CN | 103703024 B | 11/2017 |
| CN | 107660214 B | 2/2018 |
| EA | 033992 B1 | 6/2018 |
| EA | 201891694 A1 | 1/2019 |
| EP | 0 629 240 A1 | 12/1994 |
| EP | 1870459 A1 | 12/2007 |
| EP | 4137574 A1 | 2/2023 |
| JP | 2009511521 A | 3/2009 |
| JP | 2010527621 A | 8/2010 |
| JP | 2010527622 A | 8/2010 |
| JP | 2013531470 A | 8/2013 |
| WO | 92/22653 A1 | 12/1992 |
| WO | 9850431 A2 | 11/1998 |
| WO | 2000/46147 A2 | 8/2000 |
| WO | 00/70087 A1 | 11/2000 |
| WO | 2003/074569 A2 | 9/2003 |
| WO | 2004035607 A2 | 4/2004 |
| WO | 2005/004809 A2 | 1/2005 |
| WO | 2005/061547 A2 | 7/2005 |
| WO | 2005103081 A2 | 11/2005 |
| WO | 2007/042261 A2 | 4/2007 |
| WO | 2007/059782 A1 | 5/2007 |
| WO | 2007110205 A2 | 10/2007 |
| WO | 2008/003116 A2 | 1/2008 |
| WO | 2008119353 A1 | 10/2008 |
| WO | 2008119567 A2 | 10/2008 |
| WO | 2008/145137 A2 | 12/2008 |
| WO | 2008/145140 A2 | 12/2008 |
| WO | 2008/145141 A1 | 12/2008 |
| WO | 2008/157379 A2 | 12/2008 |
| WO | 2009009407 A1 | 1/2009 |
| WO | 2009/040562 A1 | 4/2009 |
| WO | 2009058383 A2 | 5/2009 |
| WO | 2009/080254 A1 | 7/2009 |
| WO | 2009/089004 A1 | 7/2009 |
| WO | 2010/015792 A1 | 2/2010 |
| WO | 2010/026923 A1 | 3/2010 |
| WO | 2010059315 A1 | 5/2010 |
| WO | 2010/080538 A1 | 7/2010 |
| WO | 2010111625 A1 | 9/2010 |
| WO | 2010/129304 A2 | 11/2010 |
| WO | 2010134666 A1 | 11/2010 |
| WO | 2011014659 A2 | 2/2011 |
| WO | 2011028952 A1 | 3/2011 |
| WO | 2011066501 A1 | 6/2011 |
| WO | 2011069104 A2 | 6/2011 |
| WO | 2011090762 A1 | 7/2011 |
| WO | 2011/117329 A1 | 9/2011 |
| WO | 2011131746 A2 | 10/2011 |
| WO | 11143545 A1 | 11/2011 |
| WO | 2012023053 A2 | 2/2012 |
| WO | 2012025525 A1 | 3/2012 |
| WO | 2012025530 A1 | 3/2012 |
| WO | 2012/058768 A1 | 5/2012 |
| WO | 2012073985 A1 | 6/2012 |
| WO | 2012/143524 A2 | 10/2012 |
| WO | 2012/158818 A2 | 11/2012 |
| WO | 2012162067 A2 | 11/2012 |
| WO | 2013/026833 A1 | 2/2013 |
| WO | 2013060867 A2 | 5/2013 |
| WO | 2013123114 A2 | 8/2013 |
| WO | 2013157953 A1 | 10/2013 |

(56)　　　　　References Cited

FOREIGN PATENT DOCUMENTS

| WO | 2014047231 A1 | 3/2014 |
|---|---|---|
| WO | 2014081202 A1 | 5/2014 |
| WO | 2014108483 A1 | 7/2014 |
| WO | 2014/131694 A1 | 9/2014 |
| WO | 2014/131711 A1 | 9/2014 |
| WO | 2015001085 A1 | 1/2015 |
| WO | 2015006749 A2 | 1/2015 |
| WO | 2015/143079 A1 | 9/2015 |
| WO | 2016007854 A1 | 1/2016 |
| WO | 2016/081490 A1 | 5/2016 |
| WO | 2016110576 A1 | 7/2016 |
| WO | 2016164404 A1 | 10/2016 |
| WO | 2017123650 A2 | 7/2017 |
| WO | 2017136433 A1 | 8/2017 |
| WO | 2017/210485 A1 | 12/2017 |
| WO | 2018165631 A1 | 9/2018 |
| WO | 2019034580 A1 | 2/2019 |
| WO | 2019155008 A1 | 8/2019 |
| WO | 2019224715 A1 | 11/2019 |
| WO | 2019224717 A2 | 11/2019 |
| WO | 2020088605 A1 | 5/2020 |
| WO | 2020102770 A1 | 5/2020 |
| WO | 2021028587 A1 | 2/2021 |
| WO | 2021224499 A1 | 11/2021 |
| WO | 2022053653 A1 | 3/2022 |
| WO | 2022053654 A1 | 3/2022 |
| WO | 2022053655 A1 | 3/2022 |
| WO | 2022053656 A1 | 3/2022 |
| WO | 2022053657 A1 | 3/2022 |
| WO | 2022053658 A1 | 3/2022 |
| WO | 2022098628 A2 | 5/2022 |
| WO | 2023198839 A2 | 10/2023 |

OTHER PUBLICATIONS

Morschhauser F. et al. "Rituximab plus Lenalidomide in Advanced Untreated Follicular Lymphoma" New England Journal of Medicine, vol. 379(10): 934-947 (2018).

Muller, D, et al., "Bispecific antibodies for cancer immunotherapy: Current perspectives," BioDrugs, vol. 24(2): 89-98 (2010).

Niemann, C et al., "Venetoclax and Ibrutinib for Patients with Relapsed/Refractory Chronic Lymphocytic Leukemia (R/R CLL)—15-Month Safety, Response and MRD Evaluation: Third Interim Analysis from the Phase II Vision HO141 Trial," Blood, vol. 134(1): Abstract 4292, 5 pages (2019).

Oken, M et al., "Toxicity and response criteria of the Eastern Cooperative Oncology Group," Am J Clin Oncol, vol. 5(6): 649-655 (1982).

Olejniczak, S et al., "A quantitative exploration of surface antigen expression in common B-cell malignancies using flow cytometry," Immunol Invest, vol. 35(1): 93-114 (2006).

Paraplatin®, retrieved on Feb. 9, 2022 www.accessdata.fda.gov/drugsatfda_docs/label/2010/020452s005lbl.pdf, 21 pages.

Patel K. et al., "Preliminary Safety and Anti-Tumor Activity of XmAb13676, an Anti-CD20 x Anti-CD3 Bispecific Antibody, in Patients with Relapsed/Refractory Non-Hodgkin's Lymphoma and Chronic Lymphocytic Leukemia", Blood, American Society of Hematology, US, vol. 134, p. 4079 (2019).

Mondello, P. et al. "Bendamustine plus Rituximab Versus R-CHOP as First-Line Treatment for Patients with Follicular Lymphoma Grade 3A: Evidence from a Multicenter, Retrospective Study," The Oncologist, vol. 23(4):454-460 (2018).

Pedersen, I. et al., "The chimeric anti-CD20 antibody rituximab induces apoptosis in B-cell chronic lymphocytic leukemia cells through a p38 mitogen activated protein-kinase-dependent mechanism," Blood, vol. 99(4): 1314-1319 (2002).

Perks, B. et al., "Bispecific antibodies direct the immune system against blood; cancers," The Pharmaceutical Journal, URI: 20068566: 2 pages (2015).

Prescribing Information for Cyclophosphamide, Retrieved on Feb. 9, 2022, www.accessdata.fda.gov/drugsatfda_docs/label/2013/012141s090,012142s112lbl.pdf, 18 pages.

Prescribing Information for Eloxatin Retrieved on Feb. 9, 2022, www.accessdata.fda.gov/drugsatfda_docs/label/2020/021759s023lbl.pdf, 42 pages.

Prescribing Information for Gemzar, Retrieved on Feb. 9, 2022, www.accessdata.fda.gov/drugsatfda_docs/label/2014/020509s077lbl.pdf 18 pages.

Prescribing Information For Infugem, Retrieved on Feb. 9, 2022, www.accessdata.fda.gov/drugsatfda_docs/label/2018/208313Orig1s000lbl.pdf, 30 pages.

Prescribing Information for Rituxan®, Retrieved on Feb. 9, 2022, www.accessdata.fda.gov/drugsatfda_docs/label/2013/103705s5414lbl.pdf, 41 pages.

Prescribing Information for Treanda, 11 pages, (2008) retrieved on Feb. 9, 2022 https://www.accessdata.fda.gov/drugsatfda_docs/label/2008/022303lbl.pdf.

Prescribing Infromation for Bendeka Retrieved on Feb. 9, 2022, www.accessdata.fda.gov/drugsatfda_docs/label/2015/208194s000lbl.pdf. 23 pages.

Prescribing Infromation for Revlimid, Retrieved on Feb. 9, 2022, www.accessdata.fda.gov/drugsatfda_docs/label/2013/021880s034lbl.pdf, 33 pages.

Prevodnik, V. et al., "The predictive significance of CD20 expression in; B-cell lymphomas," Diagn Pathol., vol. 6(33): 6 pages (2011).

Shipp et al., "A predictive model for aggressive non-Hodgkin's lymphoma," N Engl J Med., vol. 329(14): 987-994 (1993).

Shen, Qiu-Dan, et al. "Gemcitabine-oxaliplatin plus rituximab (R-GemOx) as first-line treatment in elderly patients with diffuse large B-cell lymphoma: a single-arm, open-label, phase 2 trial," Lancet Haematology, vol. 5(6): 261-269 (2018).

Relander, T. et al., "Prognostic factors in follicular lymphoma," J Clin Oncol, vol. 28(17): 2902-2913 (2010).

Rigacci, L. et al., "Oxaliplatin-based chemotherapy (dexamethasone, high-dose cytarabine, and oxaliplatin) ± rituximab is an effective salvage regimen in patients with relapsed or refractory lymphoma," Cancer, vol. 116(19): 4573-4579 (2010).

Rossi, D et al., "Integrated mutational and cytogenetic analysis identifies new prognostic subgroups in chronic lymphocytic leukemia," Blood, vol. 121(8):1403-1412 (2013).

Rudikoff, S. et al., "Single amino acid substitution altering antigen-binding specificity," PNAS, vol. 79(6):1979-83 (1982).

Rummel, M. et al.,"Bendamustine plus rituximab versus CHOP plus rituximab as first-line treatment for patients with indolent and mantle-cell lymphomas: an open-label, multicentre, randomised, phase 3 non-inferiority trial," Lancet, vol. 381 (9873):1203-1210 (2013).

Safety and Efficacy Trial of Epcoritamab Combinations in Subjects With B-cell Non-Hodgkin Lymphoma, https://clinicaltrials.gov/ct2/show/NCT04663347 ClinicalTrials.gov Identifier: NCT04663347, Nov. 3, 2021, 13 pages.

Salles, G. et al., "Efficacy and safety of idelalisib in patients with relapsed, rituximab- and alkylating agent-refractory follicular lymphoma: a subgroup analysis of a phase 2 study," Haematologica, vol. 102(4):e159 (2017).

Sarkozy, C. et al., "New drugs for the management of relapsed or refractory diffuse large B-cell lymphoma," Ann Lymphoma, vol. 3(10) 19 pages (2019).

Sehn, L. et al., "The revised International Prognostic Index (R-IPI) is a better predictor of outcome than the standard IPI for patients with diffuse large B-cell lymphoma treated with R-CHOP," Blood, vol. 109(5):1857-1861 (2007).

Seymour, JF et al., "Venetoclax-Rituximab in Relapsed or Refractory Chronic Lymphocytic Leukemia," N Engl J Med, vol. 378(12): 1107-1120 (2018).

Siegel, R et al., "Cancer statistics, 2019," 2019, CA Cancer J Clin, vol. 69(1):7-34 (2019).

Smith, E. et al."A novel, native-format bispecific antibody triggering T-cell killing of B-cells is robustly active in mouse tumor models and cynomolgus monkeys," Nat. Sci. Rep., vol. 5:17943: 12 pages (2015).

Staerz, U. et al., "Hybrid antibodies can target sites for attack by T cells," 1985, Nature, vol. 314(6012):628-31(1985).

(56)     References Cited

OTHER PUBLICATIONS

Tam, C. et al., "Ibrutinib (Ibr) Plus Venetoclax (Ven) for First-Line Treatment of Chronic Lymphocytic Leukemia (CLL)/Small Lymphocytic Lymphoma (SLL): Results from the MRD Cohort of the Phase 2 Captivate Study," Blood, vol. 134 (Supplement_1): Abstract No. 35 (2019) Abstract Only, 8 pages.

Tixier, F et al., "Comparative toxicities of 3 platinum-containing chemotherapy regimens in relapsed/refractory lymphoma patients," Hematol Oncol., vol. 35(4):584-590 (2016).

Uhm, J., "Recent advances in chronic lymphocytic leukemia therapy," Blood Res Seoul, vol. 55(S1):S72-S82(2020).

Vajdos, F. et al., "Comprehensive functional maps of the antigen-binding site of an anti-ErbB2 antibody obtained with shotgun scanning mutagenesis," J Mol Biol., vol. 320(2): 415-28 (2002).

Van der Horst, H. et al., "Duobody-CD3xCD20 Induces Potent Anti-Tumor Activity in Malignant Lymph Node B Cells from Patients with DLBCL, FL and MCL Ex Vivo, Irrespective of Prior Treatment with CD20 Monoclonal Antibodies," Blood, American Soc. of Hem., vol. 134(1): Abstract 4066: 4 pages (2019).

Varadarajan I, et al., "Management of Cytokine Release Syndrome," Chimeric Antigen receptor T-cell therapies for Cancer, Chapter 5 :45-64 (2020).

VinCRIStine Sulfate Rx only Injection, USP, Retrieved on Feb. 9, 2022, www.accessdata.fda.gov/drugsatfda_docs/label/2014/071484s042lbl.pdf, 9 pages.

Wagner-Johnston, N. et al., "Outcomes of transformed follicular lymphoma in the modern era: a report from the National LymphoCare Study (NLCS)," Blood, vol. 126(7): 851-857 (2015).

Wierda, W et al., "Multivariable model for time to first treatment in patients with chronic lymphocytic leukemia," Journ Clin Oncol., vol. 29(31): 4088-4095 (2011).

Wolchok, J et al., "Guidelines for the evaluation of immune therapy activity in solid tumors: immune-related response criteria," Clin Cancer Res, vol. 15(23): 7412-7420 (2009).

Xiong, D. et al., "Efficient inhibition of human B-cell lymphoma xenografts with an anti-CD20 x anti-CD3 bispecific diabody," Cancer Letters., vol. 177(1):29-39 (2002).

Zenz, T. et al., "From pathogenesis to treatment of chronic lymphocytic leukaemia," Nat Rev Cancer, vol. 10(1):37-50 (2010).

Adriamycin (DOXOrubicin HCl) for Injection, retrieved on Feb. 9, 2022 www.accessdata.fda.gov/drugsatfda_docs/label/2012/062921s022lbl.pdf, 1 page.

Almasri, N et al., "Reduced expression of CD20 antigen as a characteristic marker for chronic lymphocytic leukemia," Am J Hematol, vol. 40(4):259-63 (1992).

Amgen, Blinatumomab prescribing information and medication guide, Dec. 2014, 24 pages.

Bacac, M. et al., "CD20-TCB with obinutuzumab pretreatment as next generation treatment of hematological malignancies," Clin Cancer Res., vol. 24(19):4785-4797 (2018).

Barrington, S. et al., "Role of imaging in the staging and response assessment of lymphoma: consensus of the International Conference on Malignant Lymphomas Imaging Working Group," J Clin Oncol., vol. 32(27):3048-58 (2014).

Bedouelle, H. et al., "Diversity and junction residues as hotspots of binding energy in an antibody neutralizing the dengue virus," FEBS J., vol. 273(1):34-46 (2006).

Berek, J. et al., "Catumaxomab for the treatment of malignant ascites in patients with chemotherapy-refractory ovarian cancer: a phase II study," Int. J. Gynecol. Cancer, vol. 24(9): 1583-1589 (2014).

Brown, M. et al., "Tolerance of single, but not multiple, amino acid replacements in antibody VH CDR 2: a means of minimizing B cell wastage from somatic hypermutation?," J Immunol., vol. 156(9):3285-91 (1996).

Burger, J. et al., "Randomized trial of ibrutinib vs ibrutinib plus rituximab in patients with chronic lymphocytic leukemia," Blood, vol. 133(10):1011-1019 (2019).

Casulo, C. et al., "Autologous Transplantation in Follicular Lymphoma with Early Therapy Failure: A National LymphoCare Study and Center for International Blood and Marrow Transplant Research Analysis," Biol Bood Marrow Transplant, vol. 24(6):1163-71 (2018).

Cheson, B. et al., "Recommendations for initial evaluation, staging, and response assessment of Hodgkin and non-Hodgkin lymphoma: the Lugano classification," J Clin Oncol., vol. 32(27):3059-68 (2014).

Cheson, B. et al., "Refinement of the Lugano Classification lymphoma response criteria in the era of immunomodulatory therapy," Blood, vol. 128(21):2489-96 (2016).

Chiorazzi, N. et al., "Chronic lymphocytic leukemia," N Engl J Med., vol. 352(8):804-15. (2005).

Chu, S. et al., "3111 Immunotherapy with Long-Lived Anti-CD20 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias," 56th ASH Annutal Meeting and Exposition, 2 pages (2014).

CLL-IPI, "An international prognostic index for patients with chronic lymphocytic leukaemia (CLL-IPI): a meta-analysis of individual patient data," Lancet Oncol., vol. 17(6):779-790 (2016).

Coiffier, K. et al., "Guidelines for the management of pediatric and adult tumor lysis syndrome: an evidence-based review," J Clin Oncol., vol. 26(16):2767-2708 (2008).

Colman, P., "Effects of amino acid sequence changes on antibody-antigen interactions," Res Immunol., vol. 145(1):33-6 (1994).

Cytarabine—cytarabine injection, solution Hospira, Inc., lebeling, retrieved on Feb. 9, 2022, labeling.pfizer.com/ShowLabeling.aspx?id=4397.

D'Arena, G et al., "Quantitative flow cytometry for the differential diagnosis of leukemic B-cell chronic lymphoproliferative disorders," Am J Hematol, vol. 64(4): 275-281 (2000).

Dexamethasone Sodium Phosphate Label, Retrieved on Feb. 9, 2022, www.accessdata.fda.gov/drugsatfda_docs/label/2014/40572s002lbledt.pdf, 2 pages.

Doxorubicin Hydrochloride for Injection, usp, retrieved on Feb. 9, 2022 www.accessdata.fda.gov/drugsatfda_docs/label/2010/050467s070lbl.pdf, 22 pages.

Fisher, K. et al., "Venetoclax and Obinutuzumab in Patients with CLL and Coexisting Conditions," N Engl J Med., vol. 380 (23):2225-2236 (2019).

Fitzmaurice, C et al., "Global, Regional, and National Cancer Incidence, Mortality, Years of Life Lost, Years Lived With Disability, and Disability-Adjusted Life-Years for 29 Cancer Groups, 1990 to 2016: A Systematic Analysis for the Global Burden of Disease Study," JAMA Oncol., vol. 4(11):1553-68 (2018).

Garber, K., "Bispecific antibodies rise again," Nat. Rev. Drug Discov., vol. 13(11): 799-801 (2014).

GEN3013 Trial in Patients With Relapsed, Progressive or Refractory B-Cell Lymphoma, https://clinicaltrials.gov/ct2/show/study/NCT03625037, GEN3013 Trial in Patients With Relapsed . . . —Full Text View—ClinicalTrials.pdf, 8 pages (1998).

Ginaldi, L. et al., "Levels of expression of CD19 and CD20 in chronic B cell leukaemias," J Clin Pathol., vol. 51(5): 364-369 (1988).

Gisselbrecht, C et al., "Salvage regimens with autologous transplantation for relapsed large B-cell lymphoma in the rituximab era," J Clin Oncol., vol. 28 (27): 4184-90 (2010).

Goede, V et al., "Obinutuzumab plus chlorambucil in patients with CLL and coexisting conditions," N Engl J Med., vol. 370(12):1101-10 (2014).

Gokarn Y. R. et al., "Self-buffering antibody formulations," Journal of Pharmaceutical Sciences, American Chemical Society and American Pharmaceutical Association US, vol. 97(8): 3051-66 (2008).

Hallek, M. et al., "Chronic lymphocytic leukaemia," The Lancet, vol. 391(10129):1524-1537 (2018).

Hallek, M. et al., "Addition of rituximab to fludarabine and cyclophosphamide in patients with chronic lymphocytic leukaemia: a randomised, open-label, phase 3 trial," 2010, Lancet, vol. 376 (9747): 1164-1174 (2010).

Hiddemann, W. et al., "Frontline therapy with rituximab added to the combination of cyclophosphamide, doxorubicin, vincristine, and prednisone (CHOP) significantly improves the outcome for patients with advanced-stage follicular lymphoma compared with therapy

(56) References Cited

OTHER PUBLICATIONS with CHOP alone: results of a prospective randomized study of the German Low-Grade Lymphoma Study Group," Blood, vol. 106(12):3725-3732 (2005).

Howard, S. et al., "The tumor lysis syndrome," N Engl J Med, vol. 364(19): 1844-1854 (2011).

International Search Report and Written Opinion, PCT/EP2020/072927, dated Nov. 18, 2020, 10 pages.

Ito K et al., "Influence of R-CHOP Therapy on Immune System Restoration in Patients with B-Cell Lymphoma," Oncology, vol. 91(6):302-310 (2016).

Jabbour, E. et al., "Phase II Study Of The Hyper-CVAD Regimen In Combination With Ofatumumab As Frontline Therapy For Adults With CD-20 Positive Acute Lymphoblastic Leukemia (ALL)," Blood, vol. 122(21):2664: 5 pages (2003).

Jardin F., " Improving R-CHOP in diffuse large B-cell lymphoma is still a challenge" Lancet Oncology, vol. 20 (5): 605-606 (2019).

Jurinovic, V et al., "Autologous Stem Cell Transplantation for Patients with Early Progression of Follicular Lymphoma: A Follow-Up Study of 2 Randomized Trials from the German Low Grade Lymphoma Study Group," Biol Blood Marrow Transplant, vol. 24(6): 1172-9 (2018).

Kang J, et al, "Rapid formulation Development for Monoclonal Antibodies" Bioprocess International, 6 page, Apr. 12, 2016.

Khan, Y et al., "Acalabrutinib and its use in treatment of chronic lymphocytic leukemia," Future Oncol., vol. 15(6): 579-589 (2019).

Kontermann, R. et al., "Bispecific Antibodies," Drug Discov Today, vol. 20(7):838-847 (2015).

Konternamm R., "Dual targeting strategies with bispecific antibodies" mAbs vol. 4(2):182-197 (2012).

Kurokawa, T. et al., "Immune reconstitution of B-cell lymphoma patients receiving CHOP-based chemotherapy containing rituximab," Hematol Oncol., vol. 29(1): 5-9 (2011).

Labrijn, AF et al., "Efficient generation of stable bispecific IgG1 by controlled Fab-arm exchange," PNAS, vol. 110(13):5145-5150 (2013).

Labrijn, A. et al., "Controlled Fab-arm exchange for the generation of stable bispecific IgG1," Nature Protocols, vol. 9(10): 2450-63 (2014).

Lee, D et al., "ASTCT Consensus Grading for Cytokine Release Syndrome and Neurologic Toxicity Associated with Immune Effector Cells," Biol Blood Marrow Transplant, vol. 25(4): 625-638 (2019).

Leonard, J. P et al., "AUGMENT: A Phase III Study of Lenalidomide Plus Rituximab Versus Placebo Plus Rituximab in Relapsed or Refractory Indolent Lymphoma," J Clin Oncol., vol. 37(14):1188-99 (2019).

Locke, F et al., "Long-term safety and activity of axicabtagene ciloleucel in refractory large B-cell lymphoma (ZUMA-1): a single-arm, multicentre, phase 1-2 trial," Lancet Oncol., vol. 20(1):31-42 (2019).

Lum and Thakur, "Targeting T cells with bispecific antibodies for cancer therapy," BioDrugs, vol. 25(6): 365-379 (2011).

Mau-Soerensen, M. et al. "A phase I trial of intravenous catumaxomab: a bispecific monoclonal antibody targeting EpCAM and the T cell coreceptor CD," Cancer Chemother. Pharmacol., vol. 75(5): 1065-1073 (2015).

MedlinePlus. Lenalidomide, Mar. 22, 2022 pp. 1-7 (2022).

Mendez MJ, et al., "Functional transplant of megabase human immunoglobulin loci recapitulates human antibody response in mice," Nat Genet., vol. 15(2):146-56 (1997).

Mølhøj M, et al., "CD19-/CD3-bispecific antibody of the BiTE class is far superior to tandem diabody with respect to redirected tumor cell lysis," Mol Immunol., vol. 44(8):1935-43 (2007).

Mounier, N. et al., "Rituximab plus gemcitabine and oxaliplatin in patients with refractory/relapsed diffuse large B-cell lymphoma who are not candidates for high-dose therapy. A phase II Lymphoma Study Association trial," Haematologica, vol. 98(11): 1726-1731 (2013).

Mounier, N., "Rituximab plus CHOP (R-CHOP) overcomes bcl-2—associated resistance to chemotherapy in elderly patients with diffuse large B-cell lymphoma (DLBCL)," Blood, vol. 101: 4279-4284 (2003).

Myers EW et al., "Optimal alignments in linear space," Comput Appl Biosci., vol. 4(1):11-17 (1988).

NCT04358458, pp. 1-7, Apr. 20, 2020. (2020).

Needleman and Wunsch, J., "A general method applicable to the search for similarities in the amino acid sequence of two proteins," Mol. Biol., vol. 48(3): 444-453 (1970).

Neelapu SS, et al., "Chimeric antigen receptor T-cell therapy—assessment and management of toxicities," Nat Rev Clin Oncol., vol. 15(1):47-62 (2018).

Paino, T. et al., "CD20 positive cells are undetectable in the majority of multiple myeloma cell lines and are not associated with a cancer stem cell phenotype," Diagnostic Pathology, vol. 6:33 (2011).

Parren PW, et al., "On the interaction of IgG subclasses with the low affinity Fc gamma RIIa (CD32) on human monocytes, neutrophils, and platelets, Analysis of a functional polymorphism to human IgG2," J Clin Invest., vol. 90(4):1537-46 (1992).

Patrizia, M. et al. "Bendamustine plus Rituximab Versus R-CHOP as First-Line Treatment for Patients with Follicular Lymphoma Grade 3A: Evidence from a Multicenter, Retrospective Study," The Oncologist, vol. 23(4):454-460 (2018).

Paul, W. Fundamental Immunology Ch. 7 ( 2nd ed. Raven Press, N.Y. (1989).

Pearce LA, et al., "Linear gene fusions of antibody fragments with streptavidin can be linked to biotin labelled secondary molecules to form bispecific reagents," Biochem Mol Biol Int., vol. 42(6):1179-1188 (1997).

Pluckthun in 'The Pharmacology of Monoclonal Antibodies', vol. 113, Rosenburg and Moore eds. Springer-Verlag, New York, pp. 269 315 (1994).

Poncelet P, et al., "Cytofluorometric quantification of cell-surface antigens by indirect immunofluorescence using monoclonal antibodies," J Immunol Methods, vol. 85(1):65-74 (1985).

Prescribing Information for Imbruvica®, Retrieved on May 4, 2023, https://www.accessdata.fda.gov/drugsatfda_docs/label/2016/205552s007lbl.pdf, 32 pages.

Prescribing Information for Polivy®, Retrieved on May 4, 2023, https://www.accessdata.fda.gov/drugsatfda_docs/label/2019/761121s000lbl.pdf, 19 pages.

Project et al., "A predictive model for aggressive non-Hodgkin's lymphoma," N Engl J Med., vol. 329(14):987-994 (1993) Shipp.

Rasouli M. "Basic concepts and practical equations on osmolality: Biochemical approach," Clin Biochem., vol. 49(12):936-941 (2016).

Remington: The Science and Practice of Pharmacy, 19th Edition, Gennaro, Ed., Mack Publishing Co., Easton, PA, 1995.

Revets H, et al., "Nanobodies as novel agents for cancer therapy," Expert Opin Biol Ther., vol. 5(1):111-24 (2005).

Rummel, M. et al., Lymphoma: Chemotherapy, Excluding Pre-Clinical Models Non-Hodgkin Lymphoma Therapy, Blood, vol. 114 (22) (Abstract No. 405):3 pages (2009).

Sambrook et al., 1989, Molecular Cloning: A laboratory Manual, New York: Cold Spring Harbor Laboratory Press, Ch. 15.

Sarkozy and Sehn, "Management of relapsed/refractory DLBCL," Best Practice & Research in Clinical Hematology, vol. 31: 209-216 (2018).

Sarkozy, C. et al., "Cause of Death in Follicular Lymphoma in the First Decade of the Rituximab Era: A Pooled Analysis of French and US Cohorts," J Clin Oncol., vol. 37:144-152. (2018).

Schakowski F, et al., "A novel minimal-size vector (MIDGE) improves transgene expression in colon carcinoma cells and avoids transfection of undesired DNA," Mol Ther., vol. 3(5 Pt 1):793-800 (2001).

Schoonjans R, et al., "Fab chains as an efficient heterodimerization scaffold for the production of recombinant bispecific and trispecific antibody derivatives," J Immunol., vol. 165(12):7050-7 (2000).

Seiler and Hiddemann, "Advances in the management of follicular lymphoma," Current Opinion in Oncology, vol. 24(6): 742-747 (2012).

(56)            References Cited

OTHER PUBLICATIONS

Sykes KF, et al., "Linear expression elements: a rapid, in vivo, method to screen for gene functions," Nat Biotechnol., vol. 17(4):355-9 (1999).

Tessoulin, B. et al., "Carboplatin instead of cisplatin in combination with dexamethasone, high-dose cytarabine with or without rituximab (DHAC+/–R) is an effective treatment with low toxicity in Hodgkin's and non-Hodgkin's lymphomas," Annals of Hematology, vol. 96: 943-950 (2017).

The EMA Guideline on the Evaluation of Anti-cancer Medicinal Products in Man (EMA, 2012).

The EMA Guideline on the Evaluation of Anti-cancer Medicinal Products in Man (EMA, 2017).

Thieblemont, C. et al., "Epcoritamab, a Novel, Subcutaneous CD3xCD20 Bispecific T-Cell-Engaging Antibody, in Relapsed or Refractory Large B-Cell Lymphoma: Dose Expansion in a Phase I/II Trial," Clinical Oncology, vol. 41 (12): 2238-2247 (2023).

U.S. Department of Health and Human Services, FDA, Center for Drug Evaluation and Research (CDER), Jul. 2005, pp. i-iii and 1-27. (2005).

Van Heeke G, et al. "Expression of human asparagine synthetase in *Escherichia coli*," J Biol Chem., vol. 264(10):5503-9 (1989).

Wang, W. et al., "Antibody Structure, Instability, and Formulation," J Pharm Sci., vol. 96(1)1-26 (2007).

Ward, E. et al. "Binding activities of a repertoire of single immunoglobulin variable domains secreted from *Escherichia coli*," Nature, vol. 341:544-546 (1989).

Webster DM, et al., "Engineering antibody affinity and specificity," Int J Cancer Suppl., vol. 3:13-6 (1988).

Wigler M., et al. "Biochemical transfer of single-copy eucaryotic genes using total cellular DNA as donor," Cell, vol. 14(3):725-31 (1978).

Wranik BJ et al., "LUZ-Y, a novel platform for the mammalian cell production of full-length IgG-bispecific antibodies," J Biol Chem., vol. 287(52):43331-9 (2012).

Wu et al., Generation and Characterization of a Dual Variable Domain Immunoglobulin (DVD-Ig™) Molecule, In: Antibody Engineering, Springer Berlin Heidelberg (2010).

Zalevsky J, et al., "Enhanced antibody half-life improves in vivo activity," Nat Biotechnol., vol. 28(2):157-9 (2010).

Zheng, L., et al., "Expression Improvement and Mechanistic Study of the Retro-Diels-Alderase Catalytic Antibody 10F11 by Site-directed Mutagenesis," Journal of Molecular Biology, vol. 341(3), 807-14 (2004).

Zhu X. et al., "COMBODY: one-domain antibody multimer with improved avidity," Immunol Cell Biol., vol. 88(6):667-75 (2010).

Jabbour, E. et al., "Phase II Study Of The Hyper-CVAD Regimen In Combination With Ofatumumab As Frontline Therapy For Adults With CD-20 Positive Acute Lymphoblastic Leukemia (ALL)," Blood, vol. 122(21):2664: 3 pages (2003).

Kontermann R., "Dual targeting strategies with bispecific antibodies" mAbs vol. 4(2):182-197 (2012).

Labrijn et al, "Controlled fab-arm exchange for the generation of stable bispecific IgG1," Nature Protocols, vol. 9 (10): 2450-2463 (2014).

Labrijn et al., "Efficient generation of stable bispecific IgG1 by controlled Fab-arm exchange," Proc Natl Acad Sci., vol. 110(13):5145-5150 (2013).

Le Tourneau et al., "Dose escalation methods in phase I cancer clinical trials," Clinical Trials, J Natl Cancer Inst, vol. 101(10):708-720 (2009).

Li T. et al., "Novel Semi-Mechanistic Model Leveraging Preclinical and Clinical Data to Inform the Recommended Phase 2 Dose (RP2D) Selection for Epcoritamab (DuoBody CD3xCD20)", Nov. 5, 2020 (Nov. 5, 2020), pp. 1-3, Retrieved from the Internet: URL:https://ashpublications.org/blood/article/136/Supplement%201/35/472423/Novel-Semi-Mechanistic-Model-Leveraging XP055828844 [retrieved on Jul. 29, 2021].

Lugtenburg P., et al., "First-in-Human, Phase 1/2 Trial to Assess the Safety and Clinical Activity of Subcutaneous GEN3013 (DuoBody- CD3xCD2O) in B-Cell Non-Hodgkin Lymphomas," Blood, American Society of Hematology, US, vol. 134 (2019).

Oganesyan, V et al., "Structural characterization of a human Fc fragment engineered for lack of effector functions," Acta. Cryst., D64, 700-704 (2008).

Overdijk, M et al., "Crosstalk between human IgG isotypes and murine effector cells," J. Immunol., vol. 189(7): 3430-3438 (2012).

Parren, P. et al., "Induction of T-cell proliferation by recombinant mouse and chimeric mouse/human anti-CD3 monoclonal antibodies," Res Immunol., vol. 142(9): 749-763 (1991).

Prescribing Information for Bendeka Retrieved on Feb. 9, 2022, www.accessdata.fda.gov/drugsatfda_docs/label/2015/208194s000lbl.pdf. 23 pages.

Prescribing Information for Revlimid, Retrieved on Feb. 9, 2022, www.accessdata.fda.gov/drugsatfda_docs/label/2013/021880s034lbl.pdf, 33 pages.

Schuster, S et al., "Tisagenlecleucel in Adult Relapsed or Refractory Diffuse Large B-Cell Lymphoma," N Engl J Med, vol. 380(1): 45-56 (2019).

Shields, Robert L. et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, vol. 276(9):6591-6604 (2001).

Stanglmaier, M et al., "Bi20 (fBTA05), a novel trifunctional bispecific antibody (anti-CD20 x anti-CD3), mediates efficient killing of B-cell lymphoma cells even with very low CD20 expression levels," Int. J. Cancer, vol. 123(5):1181-1189 (2008).

Sun, L et al., "Anti-CD20/CD3 T cell-dependent bispecific antibody; for the treatment of B cell malignancies," Science Transl Medicine, vol. 7(287): 1-11 (2015).

Tedder, T. et al., "The B cell surface molecule B1 is functionally linked with B cell activation and differentiation," J. Immunol., vol. 135(2):973-979 (1985).

Valentine, M. et al., "Phosphorylation of the CD20 phosphoprotein in resting B lymphocytes. Regulation by protein kinase C," J. Biol. Chem., vol. 264(19):11282-11287 (1989).

Van der Neut-Kolfschoten, M. et al., "Anti-inflammatory activity of human IgG4 antibodies by dynamic Fab arm exchange," Science, vol. 317(5844):1554-1557 (2007).

Wu, C. et al., "Simultaneous targeting of multiple disease mediators by a dual-variable-domain immunoglobulin," Nat Biotechnol., vol. 25(11): 1290-1297 (2007).

Xu, D. et al., "In vitro characterization of five humanized OKT3 effector function variant antibodies," Cell Immunol., vol. 200(1):16-26 (2000).

Alvaro-Naranjo, T. et al., "CD20-negative DLBCL transformation after rituximab treatment in follicular lymphoma: a new case report and review of the literature," Ann Hematol., vol. 82:585-588 (2003).

ASCO Post Staff, "Will Bispecific Antibodies Compete With CAR T-Cell Therapy in Lymphoma?," pp. 1-5 (2020).

Ausubel, F. et al., ed. Current Protocols in Molecular Biology, Greene Publishing and Wiley InterScience New York (1987).

Bargou, R. et al., "Tumor Regression in Cancer Patients by Very Low Doses of a I Cell-Engaging Antibody," Science, vol. 321:974-977 (2008).

Bebbington, C.R. et al., "High-level expression of a recombinant antibody from myeloma cells using a glutamine synthetase gene as an amplifiable selectable marker," Biotechnology, vol. 10(2):169-75 (1992).

Bird, R.E. et al., "Single-chain antigen-binding proteins," Science, vol. 242(4877):423?426 (1988).

Blankenship JW, et al., "Abstract #5465: CD79BxDR ScorpionTM molecule: a single chain, bispecific Immunotherapeutic with potent in vitro activity against B cell lymphoma ," AACR 100th Annual Meeting, Cancer Res/, vol. 69 (9_Supplement):4 pages (2009).

Blinatumomab prescribing information and medication guide, Dec. 2014, pp. 1-20 and 1-4 (2014).

Bostrom, J. et al., "Variants of the antibody herceptin that interact with HER2 and VEGF at the antigen binding site," Science, vol. 323 (5921): 1610-1614 (2009).

Brochet X., "IMGT/V-QUEST: the highly customized and integrated system for IG and TR standardized V-J and V-D-J sequence analysis," Nucl Acids Res., vol. 36:W503-508 (2008).

(56)                    References Cited

OTHER PUBLICATIONS

Brok, H. et al., "An Extensive Monoclonal Antibody Panel for the Phenotyping of Leukocyte Subsets in the Common Marmoset and the Cotton-Top Tamarin," Cytometry, vol. 45:294-303 (2001).

Bruhns, P. et al., "Specificity and affinity of human Fcgamma receptors and their polymorphic variants for human IgG subclasses," Blood, vol. 113(16): 3716-3725 (2009).

Buckner , C. et al., "Priming B cell-mediated anti-HIV envelope responses by vaccination allows for the long-tem control of infection in macaques exposed to a R5-tropic SHIN," Virology, vol. 320, 167-180 (2004).

Chavez, J. et al., "CAR T cell therapy for B-cell lymphomas," Best Pract Res Clin Haematol., vol. 31(2):135-146 (2018).

Chiu, H. et al., "Combination lenalidomide-rituximab immunotherapy activates anti-tumour immunity and induces tumour cell death by complementary mechanisms of action in follicular lymphoma," British Journal of Haematology, vol. 185:240-253 (2019).

Chothia and Lesk J., "Canonical structures for the hypervariable regions of immunoglobulins," Mol. Biol., vol. 196(4): 901-917 (1987).

Coraro and Pearson, "Enhancing the efficiency of DNA-mediated gene transfer in mammalian cells," Somatic Cell Genetics, vol. 7(5):603-615 (1981).

Dall'Acqua, W. et al., "Properties of human IgG1s engineered for enhanced binding to the neonatal Fc receptor (FcRn)," J. Biol. Chem., vol. 281(33):23514-23524 (2006).

Deo YM, et al. "Bispecific molecules directed to the Fc receptor for IgA (Fc alpha RI, CD89) and tumor antigens efficiently promote cell-mediated cytotoxicity of tumor targets in whole blood," J Immunol., vol. 160(4):1677-86. PMID: 9469424 (1998).

Dick LW et al., "C-terminal lysine variants in fully human monoclonal antibodies: investigation of test methods and possible causes," Biotechnol Bioeng., vol. 100(6):1132-43 (2008).

Dimasi, N., et al., "The design and characterization of oligospecific antibodies for simultaneous targeting of multiple disease mediators," J Mol Biol., vol. 393(3): 672-92 (2009).

Doppalapudi VR, et al., "Chemically programmed antibodies: endothelin receptor targeting CovX-Bodies," Bioorg Med Chem Lett., vol. 17(2):501-6 (2007).

Edelman GM, et al., "The covalent structure of an entire gammaG immunoglobulin molecule," Proc Natl Acad Sci., vol. 63(1):78-85 (1969).

Evans MJ, et al., "Rapid expression of an anti-human C5 chimeric Fab utilizing a vector that replicates in COS and 293 cells," J Immunol Methods, vol. 84(1):123-38(1995).

Friend, P.J. et al., "Phase I study of an engineered aglycosylated humanized CD3 antibody in renal transplant rejection," Transplantation, vol. 68 (11): 13 pages (1999).

Genbank locus IGKC Human, P01834.2, Aug. 12, 2020, pp. 1-6 (2020).

Giavedoni, L.D. et al., "Phenotypic changes associated with advancing gestation in maternal and fetal baboon lymphocytes," Journal of Reproductive Immunology, vol. 64:121-132 (2004).

Grant, B. et al., "Expression and Secretion Vectors for Yeast," Methods in Enzymol., vol. 153: 516-544 (1987).

Hampel, P. et al., "Rapid disease progression following discontinuation of ibrutinib in patients with chronic lymphocytic leukemia treated in routine clinical practice," Leuk Lymphoma, vol. 60(11): 2712-2719 (2019).

Hinton, P. et al., "An Engineered Human IgG1 Antibody with Longer Serum; Half-Life," J. Immunol., vol. 176:346-356 (2006).

Hmila, I. et al., A bispecific nanobody to provide full protection against lethal scorpion envenoming. FASEB J., vol. 24(9):3479-3489 (2010).

Holt, L. et al., "Domain antibodies: proteins for therapy," Trends Biotechnol., vol. 21(11):484-490 (2003).

Huston, J. et al., "rotein engineering of antibody binding sites: recovery of specific activity in an anti-digoxin single-chain Fv analogue produced in *Escherichia coli*," PNAS, vol. 85(16): 5879? 5883 (1988).

Idusogie EE, et al., "Mapping of the C1q binding site on rituxan, a chimeric antibody with a human IgG1 Fc," J Immunol., vol. 164: 4178-4184 (2000).

Kabat et al., Sequences of Proteins of Immunological Interest, Fifth Edition. 1991 NIH Publication No. 91-3242.

Kohler and Milstein, "Continuous cultures of fused cells secreting antibody of predefined specificity," Nature, ol. 256 (5517) : 495-497 (1975).

LaFleur DW, et al., "Monoclonal antibody therapeutics with up to five specificities: functional enhancement through fusion of target-specific peptides," MAbs vol. 5(2):208-18 (2013).

Lawrence, L.J. "Orientation of antigen binding sites in dimeric and trimeric single chain Fv antibody fragments," FEBS Lett., vol. 425(3):479-484 (1988).

Le Gall, F. et al., "Effect of linker sequences between the antibody variable domains on the formation, stability and biological activity of a bispecific tandem diabody," Protein Eng Des Sel., vol. 17(4):357-366 (2004).

Leabman M.L. et al., "Effects of altered Fc?R binding on antibody pharmacokinetics in cynomolgus monkeys," Mabs, vol. 5(6):896-903 (2013).

Lefranc MP, et al., "IMGT, the international ImMunoGeneTics database.," Nucleic Acids Res., vol. 27(1):209-212 (1999).

Lewis SM, et al., "Generation of bispecific IgG antibodies by structure-based design of an orthogonal Fab interface," Nat Biotechnol., vol. 32(2):191-8 (2014).

Lightle S, et al., "Mutations within a human IgG2 antibody form distinct and homogeneous disulfide isomers but do not affect Fc gamma receptor or C1q binding" Protein Sci., vol. 19(4):753-62 (2010).

Lignon, J. et at, "Rituximab, Dexamethasone, Cytarabine, and Oxaliplatin (R-DHAX) Is an Effective and Safe Salvage Regimen in Relapsed/Refractory B-Cell Non-Hodgkin Lymphoma," Clinical Lymphoma, Myeloma & Leukemia, vol. 10 (4): 262-269 (2010).

Lindhofer H. et al., "Preferential species-restricted heavy/light chain pairing in rat/mouse quadromas. Implications for a single-step purification of bispecific antibodies.," J Immunol., vol. 155(1):219-25 (1995).

Maeshima, A. et al., "Follow-up Data of 10 Patients With B-cell Non-Hodgkin Lymphoma With a CD20-negative Phenotypic Change After Rituximab-containing Therapy," Am J Surg Pathol., vol. 37:563-570 (2013).

Mansfield, K. et al., "Marmoset Models Commonly Used in Biomedical Research," Comparative Med., vol. 53(4):383-92 (2003).

Marvin JS et al., "Recombinant approaches to IgG-like bispecific antibodies," Acta Pharmacol Sin., vol. 26(6):649-58 (2005).

McCafferty, J. et al., "Phage antibodies: filamentous phage displaying antibody variable domains," Nature, vol. 348:552-554 (1990).

Anderson, K.C., et al., "Expression of human B cell-associated antigens on leukemias and lymphomas: a model of human B cell differentiation," Blood, vol. 63(6):1424-1433 (1984).

Anonymous: "Definition of dose-escalation study—NCI Dictionary of Cancer Terms—National Cancer Institute," pp. 1-1,(2021) XP55828675, Retrieved from the Internet: URL:https://www.cancer.gov/publications/dictionaries/cancer-terms/def/dose-escalation-study [retrieved on Jul. 29, 2021].

Anonymous: "loading dose" SpringerLink, Jun. 27, 2021 (Jun. 27, 2021), pp. 1-2, XP055828729, Retrieved from the Internet: URL:https://link.springer.com/chapter/10.1007/978-3-211-89836-9796 [retrieved on Jul. 29, 2021].

Canfield, R. et al., "The Binding Affinity of Human IgG for its High Affinity Fc Receptor Is Determined by Multiple Amino Acids in the CH2 Domain and Is Modulated by the Hinge Region," J. Exp. Med., vol. 173: 1483-1491 (1991).

Chen, X. et al., "A Modeling Framework to Characterize Cytokine Release upon T-Cell-Engaging Bispecific Antibody Treatment: Methodology and Opportunities", CTS—Clinical and Translational Science, vol. 12(6): 600-608 (2019) XP055769696.

Collett ED—Aulton M E (Ed) 2, "Dosage Regimens", Jan. 1, 2001 (Jan. 1, 2001), Pharmaceutics. The Science of Dosage Form Design Ed. 2, Churchill Livingstone, pp. 275-288, XP003030862.

(56)         References Cited

OTHER PUBLICATIONS

Dall'Acqua, W.F., et al., "Modulation of the effector functions of a human IgG1 through engineering of its hinge region," J Immunol., vol. 177(2):1129-1138. (2006).
Duncan, A.R. et al., "The binding site for C1q on IgG," Nature, vol. 332 (6166): 738-740 (1988).
Einfeld, DA, et al., "Molecular cloning of the human B cell CD20 receptor predicts a hydrophobic protein with multiple transmembrane domains," EMBO Journ, vol. 7(3): 711-717 (1988).
Engelberts, P. et al., "DuoBody-CD3xCD20 induces potent T-cell-mediated killing of malignant B cells in preclinical models and provides opportunities for subcutaneous dosing," EBioMedicine, vol. 52: 102625 (2020).
Gall, J. et al., "T cells armed with anti-CD3 x anti-CD20 bispecific antibody enhance killing of CD20 malignant B cells and bypass complement-mediated rituximab resistance in vitro," Experimental Hematology, vol. 33: 452-459 (2005).
Gramer, M. et al., "Production of stable bispecific IgG1 by controlled Fab-arm exchange: scalability from bench to large-scale manufacturing by application of standard approaches," MAbs, vol. 5:962-973 (2013).
Herold, KC et al., "A single course of anti-CD3 monoclonal antibody hOKT3gamma1(Ala-Ala) results in improvement in C-peptide responses and clinical parameters for at least 2 years after onset of type 1 diabetes," Diabetes, vol. 54(6): 1763-1799 (2005).
Hezareh M. et al.,"Effector function activities of a panel of mutants of a broadly neutralizing antibody against human immunodeficiency virus type I," Journal of Virology, The American Society for Microbiology, US, vol. 75(24):12161-12168 (2001).
Hutchings M. et al., Epcoritamab (GEN3013; DuoBody-CD3xCD20) to induce complete response in patients with relapsed/refractory B-cell non-Hodgkin lymphoma (B-NHL): Complete dose escalation data and efficacy results from a phase I/II trial., Journal of Clinical Oncology, p. 1-3 (2020).
International Search Report, PCT/EP2021/062231, dated Aug. 9, 2021, 6 pages.
Le Toureau et al., "Dose escalation methods in phase I cancer clinical trials," Clinical Trials, J Natl Cancer Inst, vol. 101(10):708-720 (2009).
Li T. et al., "Novel Semi-Mechanistic Model Leveraging Preclinical and Clinical Data to Inform the Recommended Phase 2 Dose (RP2D) Selection for Epcoritamab (DuoBody CD3xCD20)", Nov. 5, 2020 (Nov. 5, 2020), p. 1-3, Retrieved from the Internet: URL:https://ashpublications.org/blood/article/136/Supplement%201/35/472423/Novel-Semi-Mechanistic-Model-Leveraging XP055828844 [retrieved on Jul. 29, 2021].
Patel et al., "Preliminary Safety and Anti-Tumor activity of XmAbl 3676, an Anti-CD20 x Anti-CD3 Bispecific Antibody, in Patients with Relapsed/Refractory Non-Hodgkin's Lymphoma and Chronic Lymphocytic Leukemia," Blood, Abstract only, 1 page (2019).
Sun, L. et al., "Anti-CD20/CD3 T cell-dependent bispecific antibody for the treatment of B cell malignancies," Science Translational Medicine, vol. 7(287): 287ra70, 11 pages (2015).
U.S. Appl. No. 17/939,736, filed Sep. 7, 2022, Michael Gramer.
Adriamycin (DOXOrubicin HCl) for Injection, retrieved on Feb. 9, 2022 www.accessdata.fda.gov/drugsatfda_docs/label/2012/062921s022lbl.pdf, 1 page.
Anonymous: "loading dose SpringerLink",Jun. 27, 2021 (Jun. 27, 2021), p. 1 XP055828729, Retrieved from the Internet: URL:https://link.springer.com/chapter/10.1007/978-3-211-89836-9796 [retrieved on Jul. 29, 2021].
Bacac, M. et al., "CD20-TCB with obinutuzumab pretreatment as next generation treatment of hematologic malignancies," Clin Cancer Res., vol. 24(19):4785-4797 (2018).
Cytarabine—cytarabine injection, solution Hospira, Inc., labeling, retrieved on Feb. 9, 2022, labeling.pfizer.com/ShowLabeling.aspx?id=4397.
Fischer K. et al., "Venetoclax and Obinutuzumab in Patients with CLL and Coexisting Conditions," N Engl J Med., vol. 380 (23):2225-2236 (2019).

Gall, J. M et al., "T cells armed with anti-CD3 x anti-CD20 bispecific antibody enhance killing of CD20+ malignant B cells and bypass complement-mediated rituximab resistance in vitro," Exp Hematol., vol. 33(4):452-9 (2005).
Herold, KC et al., "A single course of anti-CD3 monoclonal antibody hOKT3gamma1(Ala-Ala) results in improvement in C-peptide responses and clinical parameters for at least 2 years after onset of type 1 diabetes," Diabetes, vol. 54(6): 1763-1769 (2005).
Hutchings M. et al., Epcoritamab (GEN3013; DuoBody-CD3xCD20) to induce complete response in patients with relapsed/refractory B-cell non-Hodgkin lymphoma (B-NHL): Complete dose escalation data and efficacy results from a phase I/II trial., Journal of Clinical Oncology, 1 page (2020).
U.S. Appl. No. 17/923,317, filed Nov. 4, 2022, Tahamtan Ahmadi.
Schade, J. et al., "Retrospective Analysis of Gemcitabine and Oxaliplatin (GemOx)-Based Treatment in Patients with Relapsed/Refractory Aggressive B-Cell Non-Hodgkin Lymphoma," Blood, vol. 134 (Supplement_1) : 2904: 6 pages (2004).
Allan, J. N., et al., "Current trends in the management of Richter's syndrome," Int. J. Hematol. Oncol., vol. 7(4), IJH09, 14 pages (2018).
Anonymous—XP93036613, Understanding Lymphoma Diffuse Large B-Cell Lymphoma, pp. 1-4—URL : https : //lymphoma. org/wp-content/uploads/2 022 /10/LRF_Diffuse_Large_B_Cell_Lymphoma_Fact_Sheet .pdf, Lymphoma.org, Jan. 1, 2022, Lymphoma.org.
Anonymous, XP93037454, Pola-R-CHP Drug Combination Outperforms Standard R-CHOP Regimen for Diffuse Large B-cell Lymphoma for Progression-free Survival at Two Years, pp. 1-2, Dec. 14, 2021, Hematology.
Anonymous, XP93037628, A Study to Evaluate Adv Events and Change in Disease Activity of Subcut (SC) Epco in Comb w. Oral and Intravenous Anti-Neoplastic Agents in Adult Participants w. Non-Hodgkin Lymph, pp. 1-13, Mar. 17, 2022, ClinicalTrials.
Bagherani, N. et al., "An overview of cutaneous T cell lymphomas," F1000Research, vol. 5, 12 pages (2016).
Bitter, G.A., et al., "Expression and secretion vectors for yeast," Methods in Enzymol., vol. 153: 516-544 (1987).
Bock, A.M., et al., "Bispecific Antibodies for Non-Hodgkin Lymphoma Treatment," Current Treatment Options in Oncology, vol. 23(2):155-170 (2022).
Celgene, Beginning your R2 treatment journey, 11 pages (2019).
Chen, N., "Pharmacokinetics, metabolism and excretion of [14 C]-lenalidomide following oral administration in healthy male subjects," Cancer Chemother Pharmacol., vol. 69:789-797 (2012).
Chigrinova, E. et al., "Two main genetic pathways lead to the transformation of chronic lymphocytic leukemia to Richter syndrome," Elsevier, vol. 122(15): 2673-2682 (2013).
Coiffier et al., "Diffuse large 8-cell lymphoma: R-CHOP failure-what to do?," American Society of Hematology, vol. 1: 366-378 (2016).
Condoluci, A., et al., "Richter Syndrome," Current Oncology Reports, vol. 23(26), pp. 1-10 (2021).
Ding, L. et al., "Pembrolizumab in patients with CLL and Richter transformation or with relapsed CLL," Elsevier, vol. 129(26): 3419-3427 (2017).
Du Y. et al., "Chromatographic analysis of the acidic and basic species of recombinant monoclonal antibodies," mAbs, vol. 4(5):578-585 (2012).
Eyre, T. et al., "NCRI phase II study of CHOP in combination with ofatumumab in induction and maintenance in newly diagnosed Richter syndrome," John Wiley & Sons, Inc, vol. 175(1): 43-54 (2016).
Fabbri, G. et al., "Genetic lesions associated with chronic lymphocytic leukemia transformation to Richter syndrome," Rockefeller University Press , vol. 210(11): 2273-2288 (2013).
Falchi, L. et al, "Subcutaneous Epcoritamab with Rituximab + Lenalidomide in Patients with Relapsed or Refractory Follicular Lymphoma: Phase 1/2 Trial Update," Blood, vol. 140 (Supplement 1): 1464-1466 (2022).
Falchi, L. et al., "Correlation between FDG/PET, histology, characteristics, and survival in 332 patients with chronic lymphoid leukemia," vol. 123(18): 2783-2790 (2014).

(56)　　　　　　References Cited

OTHER PUBLICATIONS

Freedman, A. et al., "Follicular lymphoma: 2020 update on diagnosis and management," John Wiley & Sons, Inc., vol. 95(3): 316-327 (2000).

He F. et al., "Effect of sugar molecules on the viscosity of high concentration monoclonal antibody solutions," Pharm Res., vol. 28(7):1552-60. doi: 10.1007/s11095-011-0388-7. Epub May 15, 2011. PMID: 21573867. (2011).

Henricks, L.J. et al., "The use of combinations of monoclonal antibodies in clinical oncology," Cancer Treatment Reviews, vol. 41 (10):859-867 (2015).

Hiemstra, I. et al., "Duobody-CD3xCD20 Shows Unique and Potent Preclinical Anti-Tumor Activity in Vitro and In Vivo, and Is Being Evaluated Clinically in Patients with B-Cell Malignancies," Blood, vol. 132 (Suppl): 3 pages (2018).

Hillmen, P. et al., Acalabrutinib Monotherapy in Patients with Richter Transformation from the Phase 1/2 ACE-CL-001 Clinical Study, 128(22), 6 pages, Dec. 2, 2016, Elsevier.

Hirsch et al., "Anti-Cd3-Mediated Immunotherapy: A Murine Model," pp. 1-15 of Chapter 1 from William J. Burlingham "A Critical A Critical Analysis of Monoclonal Antibody Therapy in Transplantation," 1992.

Hutchings, M. et al., "Subcutaneous (SC) Epcoritamab (GEN3013; DuoBody-CDSxCDZO) in Patients with Relapsed/Refractory (R/R) B-Cell Non-Hodgkin Lymphoma (B-NHL): Dose-Escalation Data from a Phase I/II Trial," Clinical Lymphoma, Myeloma & Leukemia, S274: 1 page (2020).

Hutchings, M. et al., "Dose escalation of subcutaneous epcoritamab in patients with relapsed or refractory B-cell non-Hodgkin lymphoma: an open-label, phase 1/2 study," Lancet, vol. 398: 1157-1169 (2021).

Izutsu, K. et al., O13-3 Subcutaneous epcoritamab in Japanese patients with relapsed/refractory diffuse large B-cell lymphoma: EPCORE NHL-3 data, pp. S1389-S1389, Nov. 1, 2023, Elsevier.

Jain, N. et al., "Nivolumab Combined with Ibrutinib for CLL and Richter Transformation: A Phase II Trial," American Society of Hematology, vol. 182(22), 4 pages (2016).

Johnson et al., "Diffuse large B-cell lymphoma: reduced CD20 expression is associated with an inferior survival," Blood,vol. 113 (16): 3773-3780 (2009).

Jorgensen, L. et al., "Recent trends in stabilising peptides and proteins in pharmaceutical formulation—considerations in the choice of excipients," Expert Opinion on Drug Delivery vol. 6(11): 1219-1230 (2009).

Kamerzell TJ, "Protein-excipient interactions: mechanisms and biophysical characterization applied to protein formulation development," Adv Drug Deliv Rev., vol. 63(13):1118-59. doi: 10.1016/j.addr.2011.07.006. Epub Jul. 29, 2011. PM ID: 21855584. (2011).

Khawli, L. et al., "Charge variants in IgG1: Isolation, characterization, in vitro binding properties and pharmacokinetics in rats," mAbs, vol. 2(6):613-624 (2010).

Komori, M. et al., "Insufficient disease inhibition by intrathecal rituximab in progressive multiple sclerosis," Annals of Clinical and Translational Neurology, vol. 3(3): 166-179. (2016).

Langerbeins, P. et al., "Poor efficacy and tolerability of R?CHOP in relapsed/refractory chronic lymphocytic leukemia and Richter transformation, 89(12), pp. E239-E243, Nov. 19, 2014.

Li, T. et al., "Simplifying Selection and Optimization of Step-Up Dosing of Subcutaneous Epcoritamab to Mitigate CRS Risk Using Repeated Time-to-Event Modeling," Abstract 2798, Apr. 17, 2023, AACR, Orlando, FL, 3 pages.

Linton, K.M. et al., "EPCORE FL-2: Phase 3 trial of epcoritamab with rituximab and lenalidomide (R2) vs chemoimmunotherapy or R2 in previously untreated follicular lymphoma,"J. Clin. Oncol., vol. 42(16): 1 page (2024).

Lugtenburg, P., et al., "Efficacy and safety of SC and IV rituxi plus cyclophosph, doxorub, vincris, and pred in first-line diffuse large B-cell lymph-the randomized MabEase study,"Haematologica, vol. 102(11):1913-1922 (2017).

Machover, D. et al., "Dexamethasone, high-dose cytarabine, and oxaliplatin (DHAOx) as salvage treatment for patients with initially refractory or relapsed non-Hodgkin's lymphoma," Annals of Oncology, vol. 12: 1439-1443 (2001).

Martelli et al., "Diffuse large B-cell lymphoma," Critical Reviews in Oncology/Hematology, vol. 87(2):146-171 (2013).

Matsushita, T. et al., "Regulatory B cells inhibit EAE initiation in mice while other B cells promote disease progression," J Clin Invest., vol. 118(10):3420-3430 (2008).

Maurer et al., "Immunotargeting of tumor subpopulations in melanoma patients," OncoImmunology, vol. 1(8):1454-1456 (2012).

Merrill, J. et al., "Efficacy and safety of rituximab in moderately-to-severely active systemic lupus erythematosus: the randomized, double-blind, phase II/III systemic lupus erythematosus evaluation of rituximab trial," Arthritis & Rheumatism, vol. 62 (1):222-233 (2010).

Middelburg, J. et al., "Overcoming Challenges for CD3-Bispecific Antibody Therapy in Solid Tumors," Cancers, vol. 13(287): 25 pages (2021).

Parikh, S. et al., "Diffuse large B-cell lymphoma (Richter syndrome) in patients with chronic lymphocytic leukaemia (CLL): a cohort study of newly diagnosed patients," John Wiley & Sons, Inc., vol. 162 (6): 774-782 (2013).

Parikh, S. et al., "How we treat Richter syndrome," Elsevier, vol. 123(11): 1647-1657 (2014).

Paul, W. Fundamental Immunology Ch. 9 (3rd ed. Raven Press, N.Y. 6 pages (1993).

Paul, W., Fundamental Immunology, Chap. 8, 1993, Raven Press, NY, 6 pages.

Pham NB et al., "Protein aggregation and immunogenicity of biotherapeutics," Int J Pharm., vol. 585:119523, 19 pages. doi:10.1016/j.ijpharm.2020.119523. Epub Jun. 9, 2020. PMID: 32531452; PMCID: PMC7362938. (2020).

Rogers, K. et al., "A single-institution retrospective cohort study of first-line R-EPOCH chemoimmunotherapy for Richter syndrome demonstrating complex chronic lymphocytic leukaemia karyotype as an adverse prognostic factor," John Wiley & Sons, Inc., vol. 180(2): 259-266 (2018).

Rossi, D. et al., "Biological and clinical risk factors of chronic lymphocytic leukaemia transformation to Richter syndrome," Br J Haematol., vol. 142(2):202-15 (2008).

Yoshizawa, T. et al., "Anti-tumour efficacy study of the Bruton's tyrosine kinase (Btk) inhibitor, ONO-4059, in combination with the glycoengineered type II anti-CD20 monoclonal antibody, obinutuzumab(GA101) demonstrates superior in vivo efficacy compared to ONO-4059 in combination with rituximab] Bruton's tyrosine kinase (Btk) inhibitor, ONO-4059 no tokuchou to anti-CD20 antibody Obinutuzumab tono heiyou niyoru koushuyou kouka zoukyou," Hematology, vol. 69(1): 95-101 (2014).

Rossi, D. et al., "Biology and treatment of Richter syndrome," Elsevier, vol. 131(25): 2761-2772 (2018).

Rossi, et al., "Stereotyped B-Cell Receptor Is an Independent Risk Factor of Chronic Lymphocytic Leukemia Transformation to Richter Syndrome," American Association for Cancer Research , vol. 15(13): 4415-4422 (2009).

Rovin, B. et al., "Efficacy and safety of rituximab in patients with active proliferative lupus nephritis: the Lupus Nephritis Assessment with Rituximab study," Arthritis & Rheumatism, vol. 64(4):1215-1226 (2012).

Rummel, M., et al., "Bendamustine Plus Rituximab Is Superior in Respect of Progress ionFree Survival and CR Rate When Compared to CHOP Plus Rituximab as First-Line Treatment of Patients with Advanced Follicular, Indolent, and Mantle Cell Lymphomas: Final Results of a Randomized Phase III Study of the Stil (Study Group Indolent Lymphomas, Germany).," Blood, vol. 114(22): 405, 8 pages (2009).

Salles, G., "How do I sequence therapy for follicular lymphoma?," Hematology Am Soc Hematol Educ Program, vol. 1:287-294 (2020).

Sela-Culang I, et al., "The structural basis of antibody-antigen recognition," Front Immunol., vol. 4(302):13 pages (2013).

(56) References Cited

OTHER PUBLICATIONS

Shen, Q. et al., "Gemcitabine-oxaliplatin plus rituximab (R-GemOx) as first-line treatment in elderly patients with diffuse large B-cell lymphoma: a single-arm, open-label, phase 2 trial," Elsevier, vol. 5(6):261-269 (2018).

Singh, S. M., et al., "Effect of Polysorbate 20 and Polysorb 80 on the Higher-Order Structure of a Monocl Antibody and Its Fab and Fc Fragments Probed Using 2D Nuclear Magnetic Reson Spectro," Journ of Pharmaceu. Sciences, vol. 106(12): 3486-3498 (2017).

Singh, V. et al., "Development of Novel Anti-Cd20 Monoclonal Antibodies and Modulation in Cd20 Levels on Cell Surface: Looking to Improve Immunotherapy Response," J Cancer Sci Ther., vol. 7(11):347-358 (2015).

Smith, E., et al., Anti-CD20/CD3 T cell-dependent bispecific antibody for the treatment of B cell malignancies, 5 (17943), 12 pages, 2015.

Stuve, O. et al., "CD19 as a molecular target in CNS autoimmunity," Acta Neuropathol., vol. 128:177-190 (2014).

Swerdlow, et al., "WHO Classification of Tumours of Haematopoietic and Lymphoid Tissues," International Agency for Research on Cancer, pp. 10-12 (2017).

Tsimberidou, A. et al., "Phase I-II Clinical Trial of Oxaliplatin, Fludarabine, Cytarabine, and Rituximab Therapy in Aggressive Relapsed/Refractory Chronic Lymphocytic Leukemia or Richter Syndrome," Elsevier, vol. 13(5): 568-574 (2013).

Van Der Horst, H., et al., "Epco induces potent anti-tumor activity against malignant B-cells from patients with DLBCL, FL and MCL, irrespect of prior CD20 monoclo antibody treatment," Blood Cancer Journ., vol. 11(2) 8 pages (2021).

Wang, W., et al., "Instability, stabilization, and formulation of liquid protein pharmaceuticals," International Journal of Pharmaceutics vol. 185(2):129-188 (1999).

Wang, Y. et al., "Clinical characteristics and outcomes of Richter transformation: experience of 204 patients from a single center," Ferrata Storti Foundation, vol. 105(3): 765-773 (2020).

Wu et al., Generation and Characterization of a Dual Variable Domain Immunoglobulin (DVD-Ig™) Molecule, In: Antibody Engineering, Springer Berlin Heidelberg, 12 pages (2010).

Younes, B. et al., "Safety and Efficacy of the Combination of Ibrutinib and Nivolumab in Patients with Relapsed Non-Hodgkin Lymphoma or Chronic Lymphocytic Leukemia," American Society of Hematology , vol. 130, 4 pages (2017).

Aukema, S. et al., "Double-hit B-cell lymphomas" Blood, vol. 117 (8):2319-2331 (2011).

Caimi et al, "Safety and Efficacy of Venetoclax Combined with Rituximab, Ifosfamide, Carboplatin and Etoposide Chemoimmunotherapy (VICER) for Treatment of Relapsed Diffuse Large B Cell Lymphoma: Results from the Phase 1 Study," Blood, vol. 132 (Supp 1) 397: 5 pages (2018).

ClinicalTrials.gov ID NCT05578976 (pp. 1-11; Oct. 13, 2022).

Drug Bank Epcoritamab, accessed online Oct. 21, 2025, 12 pages (2021).

Engelberts, P. et al., "DuoBody-CD3xCD20 induces potent T-cell-mediated killing of malignant B cells in preclinical-node's and provides opportunities for subcutaneous dosing," EBioMedicine, vol. 52: 102625: 13 pages (2020).

Falchi, L. et al., "Subcutaneous Epcoritamab with Rituximab + Lenalidomide (R2) in Patients with Relapsed or Refractory Follicular Lymphoma: Phase 1/2 Trial Update," American Soc. of Clinical Oncology, Abstract 7524, 1 page (2022).

FDA grants accelerated approval to epcoritamabbysp for relapsed or refractory follicular lymphoma (retrieved from the intenet Nov. 5, 2025) 1 page https://www.fda.gov/drugs/resources-information-approved-drugs/.

Gnaoui et al, "Rituximab, gemcitabine and oxaliplatin: an effective salvage regimen for patients with relapsed or refractory B-cell lymphoma not candidates for high-dose therapy," Annals of Oncology, vol. 18 (8): 1363-1368 (2007).

Ilda, S., et al., "Safety and efficacy of daratumumab in combination with bortezomib and dexamethasone in Japanese patients with relapsed or refractory multiple myeloma,"Intern Journ of Hema., vol. 107(4): 460-467 (2017).

Kramer, M.H.H; "Clinical Relevance of BCL2, BCL6, and MYC Rearrangements in Diffuse Large B-Cell Lymphoma". Blood, vol. 92 (9): 3152-3162. doi: https://doi.org/10.1182/blood.V92.9.3152 (1998).

Leiper, K. et al., "Randomised placebo-controlled trial of rituximab (anti-CD20) in active ulcerative colitis," Gut, vol. 60(11):1520-1526 (2011).

Locke, F et al., "Long-term safety and activity of axicabtagene ciloleucel in refractory large B-cell lymphoma (ZUMA-1): 3 single-arm, multicentre, phase 1-2 trial," Lancet Oncol., vol. 20(1):31-42 (2019).

Mok, M. et al., "New onset psoriasis after rituximab for treatment of idiopathic membranous nephropathy," Nephrology, vol. 19 (1):60-63 (2014).

Pearce E.J., et al., "Downregulation of Th1 Cytokin Production Accompanies Induction of Th2 Responses by a Parasitic Helminth, Schistosoma mansoni," The Journal of Medicine, vol. 173:159-166 (1991).

Sun, L. et al., "Anti-CD20/CD3 T cell-dependent bispecific antibody for the treatment of B cell malignancies," Sci Transl Med., vol. 7(287): 12 pages (2015).

The Epkinly website (epkinlyhcp.com/fl/dosing-administration) by Genmab , retrieved on Nov. 4, 2025, 2 pages.

Tilly, H. et al., "Polatuzumab Vedotin in Previously Untreated Diffuse Large B-Cell Lymphoma,"of Medicine, vol. 386(4): 351-363 (2022).

* cited by examiner

SEQUENCE LISTING

```
<160> NUMBER OF SEQ ID NOS: 27

<210> SEQ ID NO 1
<211> LENGTH: 8
<212> TYPE: PRT
<213> ORGANISM: Artificial sequence
<220> FEATURE:
<223> OTHER INFORMATION: Antibody CDR sequence

<400> SEQUENCE: 1

Gly Phe Thr Phe Asn Thr Tyr Ala
1               5

<210> SEQ ID NO 2
<211> LENGTH: 10
<212> TYPE: PRT
<213> ORGANISM: Artificial sequence
<220> FEATURE:
<223> OTHER INFORMATION: Antibody CDR sequence

<400> SEQUENCE: 2

Ile Arg Ser Lys Tyr Asn Asn Tyr Ala Thr
1               5                   10

<210> SEQ ID NO 3
<211> LENGTH: 16
```

-continued

```
<212> TYPE: PRT
<213> ORGANISM: Artificial sequence
<220> FEATURE:
<223> OTHER INFORMATION: Antibody CDR sequence

<400> SEQUENCE: 3

Val Arg His Gly Asn Phe Gly Asn Ser Tyr Val Ser Trp Phe Ala Tyr
1               5                   10                  15

<210> SEQ ID NO 4
<211> LENGTH: 9
<212> TYPE: PRT
<213> ORGANISM: Artificial sequence
<220> FEATURE:
<223> OTHER INFORMATION: Antibody CDR sequence

<400> SEQUENCE: 4

Thr Gly Ala Val Thr Thr Ser Asn Tyr
1               5

<210> SEQ ID NO 5
<211> LENGTH: 9
<212> TYPE: PRT
<213> ORGANISM: Artificial sequence
<220> FEATURE:
<223> OTHER INFORMATION: Antibody CDR sequence

<400> SEQUENCE: 5

Ala Leu Trp Tyr Ser Asn Leu Trp Val
1               5

<210> SEQ ID NO 6
<211> LENGTH: 125
<212> TYPE: PRT
<213> ORGANISM: Artificial sequence
<220> FEATURE:
<223> OTHER INFORMATION: Antibody variable domain sequence

<400> SEQUENCE: 6

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 7
<211> LENGTH: 109
<212> TYPE: PRT
<213> ORGANISM: Artificial sequence
<220> FEATURE:
<223> OTHER INFORMATION: Antibody variable domain sequence

<400> SEQUENCE: 7
```

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 8
<211> LENGTH: 8
<212> TYPE: PRT
<213> ORGANISM: Artificial sequence
<220> FEATURE:
<223> OTHER INFORMATION: Antibody CDR sequence

<400> SEQUENCE: 8

```
Gly Phe Thr Phe His Asp Tyr Ala
1               5
```

<210> SEQ ID NO 9
<211> LENGTH: 8
<212> TYPE: PRT
<213> ORGANISM: Artificial sequence
<220> FEATURE:
<223> OTHER INFORMATION: Antibody CDR sequence

<400> SEQUENCE: 9

```
Ile Ser Trp Asn Ser Gly Thr Ile
1               5
```

<210> SEQ ID NO 10
<211> LENGTH: 15
<212> TYPE: PRT
<213> ORGANISM: Artificial sequence
<220> FEATURE:
<223> OTHER INFORMATION: Antibody CDR sequence

<400> SEQUENCE: 10

```
Ala Lys Asp Ile Gln Tyr Gly Asn Tyr Tyr Tyr Gly Met Asp Val
1               5                   10                  15
```

<210> SEQ ID NO 11
<211> LENGTH: 6
<212> TYPE: PRT
<213> ORGANISM: Artificial sequence
<220> FEATURE:
<223> OTHER INFORMATION: Antibody CDR sequence

<400> SEQUENCE: 11

```
Gln Ser Val Ser Ser Tyr
1               5
```

<210> SEQ ID NO 12
<211> LENGTH: 9
<212> TYPE: PRT
<213> ORGANISM: Artificial sequence
<220> FEATURE:
<223> OTHER INFORMATION: Antibody CDR sequence

<400> SEQUENCE: 12

Gln Gln Arg Ser Asn Trp Pro Ile Thr
1               5

<210> SEQ ID NO 13
<211> LENGTH: 122
<212> TYPE: PRT
<213> ORGANISM: Artificial sequence
<220> FEATURE:
<223> OTHER INFORMATION: Antibody variable domain sequence

<400> SEQUENCE: 13

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Thr Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 14
<211> LENGTH: 107
<212> TYPE: PRT
<213> ORGANISM: Artificial sequence
<220> FEATURE:
<223> OTHER INFORMATION: Antibody variable domain sequence

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 15
<211> LENGTH: 329
<212> TYPE: PRT
<213> ORGANISM: Homo Sapiens -continued

```
<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 16
<211> LENGTH: 329
<212> TYPE: PRT
<213> ORGANISM: Artificial sequence
<220> FEATURE:
<223> OTHER INFORMATION: Antibody constant region

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

-continued

```
                  20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 17
<211> LENGTH: 329
<212> TYPE: PRT
<213> ORGANISM: Artificial sequence
<220> FEATURE:
<223> OTHER INFORMATION: Antibody constant region

<400> SEQUENCE: 17

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

-continued

```
              50                  55                  60
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 18
<211> LENGTH: 329
<212> TYPE: PRT
<213> ORGANISM: Artificial sequence
<220> FEATURE:
<223> OTHER INFORMATION: Antibody constant region

<400> SEQUENCE: 18
```

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
```

```
                    85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Arg Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 19
<211> LENGTH: 329
<212> TYPE: PRT
<213> ORGANISM: Artificial sequence
<220> FEATURE:
<223> OTHER INFORMATION: Antibody constant region

<400> SEQUENCE: 19

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
```

-continued

```
              115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 20
<211> LENGTH: 329
<212> TYPE: PRT
<213> ORGANISM: Artificial sequence
<220> FEATURE:
<223> OTHER INFORMATION: Antibody constant region

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
```

-continued
_____

```
145              150              155              160

Tyr Val Asp Gly Val Glu Val His Asn Ala Lys Thr Lys Pro Arg Glu
                165              170              175

Glu Gln Tyr Asn Ser Thr Tyr Arg Val Val Ser Val Leu Thr Val Leu
                180              185              190

His Gln Asp Trp Leu Asn Gly Lys Glu Tyr Lys Cys Lys Val Ser Asn
                195              200              205

Lys Ala Leu Pro Ala Pro Ile Glu Lys Thr Ile Ser Lys Ala Lys Gly
                210              215              220

Gln Pro Arg Glu Pro Gln Val Tyr Thr Leu Pro Pro Ser Arg Glu Glu
225              230              235              240

Met Thr Lys Asn Gln Val Ser Leu Thr Cys Leu Val Lys Gly Phe Tyr
                245              250              255

Pro Ser Asp Ile Ala Val Glu Trp Glu Ser Asn Gly Gln Pro Glu Asn
                260              265              270

Asn Tyr Lys Thr Thr Pro Pro Val Leu Asp Ser Asp Gly Ser Phe Phe
                275              280              285

Leu Tyr Ser Arg Leu Thr Val Asp Lys Ser Arg Trp Gln Gln Gly Asn
                290              295              300

Val Phe Ser Cys Ser Val Met His Glu Ala Leu His Asn His Tyr Thr
305              310              315              320

Gln Lys Ser Leu Ser Leu Ser Pro Gly
                325

<210> SEQ ID NO 21
<211> LENGTH: 106
<212> TYPE: PRT
<213> ORGANISM: Homo Sapiens

<400> SEQUENCE: 21

Gly Gln Pro Arg Glu Pro Gln Val Tyr Thr Leu Pro Pro Ser Arg Glu
1               5               10              15

Glu Met Thr Lys Asn Gln Val Ser Leu Thr Cys Leu Val Lys Gly Phe
                20              25              30

Tyr Pro Ser Asp Ile Ala Val Glu Trp Glu Ser Asn Gly Gln Pro Glu
                35              40              45

Asn Asn Tyr Lys Thr Thr Pro Pro Val Leu Asp Ser Asp Gly Ser Phe
                50              55              60

Phe Leu Tyr Ser Lys Leu Thr Val Asp Lys Ser Arg Trp Gln Gln Gly
65              70              75              80

Asn Val Phe Ser Cys Ser Val Met His Glu Ala Leu His Asn His Tyr
                85              90              95

Thr Gln Lys Ser Leu Ser Leu Ser Pro Gly
                100             105

<210> SEQ ID NO 22
<211> LENGTH: 106
<212> TYPE: PRT
<213> ORGANISM: Homo Sapiens

<400> SEQUENCE: 22

Gly Gln Pro Lys Ala Ala Pro Ser Val Thr Leu Phe Pro Pro Ser Ser
1               5               10              15

Glu Glu Leu Gln Ala Asn Lys Ala Thr Leu Val Cys Leu Ile Ser Asp
                20              25              30

Phe Tyr Pro Gly Ala Val Thr Val Ala Trp Lys Ala Asp Ser Ser Pro
```

-continued

```
        35                    40                    45
Val Lys Ala Gly Val Glu Thr Thr Thr Pro Ser Lys Gln Ser Asn Asn
    50                    55                    60

Lys Tyr Ala Ala Ser Ser Tyr Leu Ser Leu Thr Pro Glu Gln Trp Lys
65                    70                    75                    80

Ser His Arg Ser Tyr Ser Cys Gln Val Thr His Glu Gly Ser Thr Val
                85                    90                    95

Glu Lys Thr Val Ala Pro Thr Glu Cys Ser
            100                    105
```

```
<210> SEQ ID NO 23
<211> LENGTH: 107
<212> TYPE: PRT
<213> ORGANISM: Homo Sapiens

<400> SEQUENCE: 23
```

```
Arg Thr Val Ala Ala Pro Ser Val Phe Ile Phe Pro Pro Ser Asp Glu
1                    5                    10                    15

Gln Leu Lys Ser Gly Thr Ala Ser Val Val Cys Leu Leu Asn Asn Phe
                20                    25                    30

Tyr Pro Arg Glu Ala Lys Val Gln Trp Lys Val Asp Asn Ala Leu Gln
            35                    40                    45

Ser Gly Asn Ser Gln Glu Ser Val Thr Glu Gln Asp Ser Lys Asp Ser
    50                    55                    60

Thr Tyr Ser Leu Ser Ser Thr Leu Thr Leu Ser Lys Ala Asp Tyr Glu
65                    70                    75                    80

Lys His Lys Val Tyr Ala Cys Glu Val Thr His Gln Gly Leu Ser Ser
                85                    90                    95

Pro Val Thr Lys Ser Phe Asn Arg Gly Glu Cys
            100                    105
```

```
<210> SEQ ID NO 24
<211> LENGTH: 454
<212> TYPE: PRT
<213> ORGANISM: Artificial sequence
<220> FEATURE:
<223> OTHER INFORMATION: Antibody heavy chain sequence

<400> SEQUENCE: 24
```

```
Glu Val Lys Leu Val Glu Ser Gly Gly Gly Leu Val Gln Pro Gly Gly
1                    5                    10                    15

Ser Leu Arg Leu Ser Cys Ala Ala Ser Gly Phe Thr Phe Asn Thr Tyr
                20                    25                    30

Ala Met Asn Trp Val Arg Gln Ala Pro Gly Lys Gly Leu Glu Trp Val
            35                    40                    45

Ala Arg Ile Arg Ser Lys Tyr Asn Asn Tyr Ala Thr Tyr Tyr Ala Asp
    50                    55                    60

Ser Val Lys Asp Arg Phe Thr Ile Ser Arg Asp Asp Ser Lys Ser Ser
65                    70                    75                    80

Leu Tyr Leu Gln Met Asn Asn Leu Lys Thr Glu Asp Thr Ala Met Tyr
                85                    90                    95

Tyr Cys Val Arg His Gly Asn Phe Gly Asn Ser Tyr Val Ser Trp Phe
            100                    105                    110

Ala Tyr Trp Gly Gln Gly Thr Leu Val Thr Val Ser Ser Ala Ser Thr
        115                    120                    125

Lys Gly Pro Ser Val Phe Pro Leu Ala Pro Ser Ser Lys Ser Thr Ser
    130                    135                    140
```

-continued

```
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
        210                 215                 220

Pro Lys Ser Cys Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Ala Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly
    450
```

```
<210> SEQ ID NO 25
<211> LENGTH: 215
<212> TYPE: PRT
<213> ORGANISM: Artificial sequence
<220> FEATURE:
<223> OTHER INFORMATION: Antibody light chain sequence

<400> SEQUENCE: 25

Gln Ala Val Val Thr Gln Glu Pro Ser Phe Ser Val Ser Pro Gly Gly
1                   5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
            35                  40                  45
```

```
Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Thr Glu Cys Ser
    210                 215
```

<210> SEQ ID NO 26
<211> LENGTH: 451
<212> TYPE: PRT
<213> ORGANISM: Artificial sequence
<220> FEATURE:
<223> OTHER INFORMATION: Antibody heavy chain sequence

<400> SEQUENCE: 26

```
Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
            35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190
```

```
Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

```
<210> SEQ ID NO 27
<211> LENGTH: 214
<212> TYPE: PRT
<213> ORGANISM: Artificial sequence
<220> FEATURE:
<223> OTHER INFORMATION: Antibody light chain sequence

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95
```

-continued

```
Thr Phe Gly Gln Gly Thr Arg Leu Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
        210
```

BISPECIFIC ANTIBODIES AGAINST CD3 AND CD20

CROSS-REFERENCE TO RELATED APPLICATIONS

This application is a 35 U.S.C. 371 national stage filing of International Application No. PCT/EP2021/062231, filed May 7, 2021, which claims priority to U.S. Provisional Application Nos. 63/022,212 filed May 8, 2020, 63/078,667 filed Sep. 15, 2020, and 63/121,690 filed Dec. 4, 2020. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Nov. 4, 2022, is named GMI-192US_SequenceListing_2022-11-04.txt and is 39144 bytes in size.

FIELD

The present invention relates to bispecific antibodies (bsAbs) targeting both CD3 and CD20 and the use of such antibodies in the treatment of disease in subjects. Moreover, advantageous treatment regimens are provided.

INTRODUCTION

Monoclonal antibodies (mAbs) have been shown to be highly successful for the treatment of cancer. A further promising approach to improve antibody therapy is by recruiting T cells specifically to the antigen-expressing cancer cells. This can be achieved by utilizing bsAbs targeting both T cells and antigen-expressing cells. However, initial clinical studies were rather disappointing mainly due to low efficacy, severe adverse effects (cytokine storm) and immunogenicity of the bispecific antibodies. Advances in the design and application of bispecific antibodies have partially overcome the initial barrier of cytokine release syndrome and improved clinical effectiveness without dose-limiting toxicities (Garber, 2014, Nat. Rev. Drug Discov. 13: 799-801).

The CD20 molecule, also called human B-lymphocyte-restricted differentiation antigen or Bp35, is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin lymphomas (B-NHL), but is not found on hematopoietic stem cells, pro-B cells, normal plasma cells, or other normal tissues. Methods for treating cancer as well as autoimmune and immune diseases by targeting CD20 are known in the art.

For example, the chimeric CD20 antibody rituximab has been used for or suggested for use in treating cancers such as B-NHL and chronic lymphocytic leukemia (CLL). The human monoclonal anti-CD20 antibody ofatumumab has been used for or suggested for use in treating among others various CLL indications, follicular lymphoma (FL), neuromyelitis optica (NMO), diffuse and relapsing-remitting multiple sclerosis (RRMS).

Currently, bispecific antibodies are under development that target both CD20 and CD3. For example, WO2011028952 describes amongst others the generation of CD3×CD20 bispecific molecules using Xencor's XmAb bispecific Fc domain technology, WO2014047231 describes REGN1979 and other CD3×CD20 bispecific antibodies generated using the FcΔAdp technology from Regeneron Pharmaceuticals, and Sun et al. (2015, Science Translational Medicine 7, 287ra70) describe a B cell-targeting anti-CD20/CD3 T cell-dependent bispecific antibody constructed using "knobs-into-holes" technology. Such bispecific antibodies are currently being tested in clinical trials for specific indications in humans.

A bispecific antibody of particular interest that is under development is epcoritamab (Duobody CD3×CD20; GEN3013) (Engelberts et al., 2020, EBioMedicine, Vol. 52, 102625, WO2016110576, and WO2019155008, incorporated herein by reference).

Although there are currently treatment regimens available for the treatment of CD20+ cancers, such as B-NHL, there is still a need for further therapeutic options, as there still remain patients that relapse or are refractory to currently available treatments. Epcoritamab is a candidate that can add to the repertoire of treatments options that may benefit patients suffering from cancers such as B-NHL.

Hence, one object of the present invention is to provide for means and methods for treating a cancer by using a bispecific antibody targeting CD3×CD20 as described herein, such as epcoritamab, as well as providing a bispecific antibody targeting CD3×CD20 as described herein, such as epcoritamab, for use in the treatment of a cancer.

Specific dose ranges and/or dosage regimens are provided that are advantageous with regard to such methods or uses, such as for a cancer known or identified as being positive for CD20, such as a B-NHL. More in particular, specific dose ranges and/or dosage regimens are provided herein that are advantageous with regard to the treatment of patients suffering from diffuse large B-cell lymphoma (DLBCL), High Grade B-cell lymphoma, FL. The dose ranges and/or dosage regimens provided herein were assessed to be safe for human use and/or shown to be highly effective in the treatment of B-NHL.

FIGURES

FIG. 1. Population PK model predicted target-mediated drug disposition (TMDD) saturation. For each dose, 100 virtual patients were simulated and model predicted TMDD saturation were summarized with box and whisker plot, representing median (middle horizontal bar), $25^{th}$ and $75^{th}$ percentile (lower and upper hinges), 1.5*inter-quartile range (whisker), and outliers (points).

Figure 2:
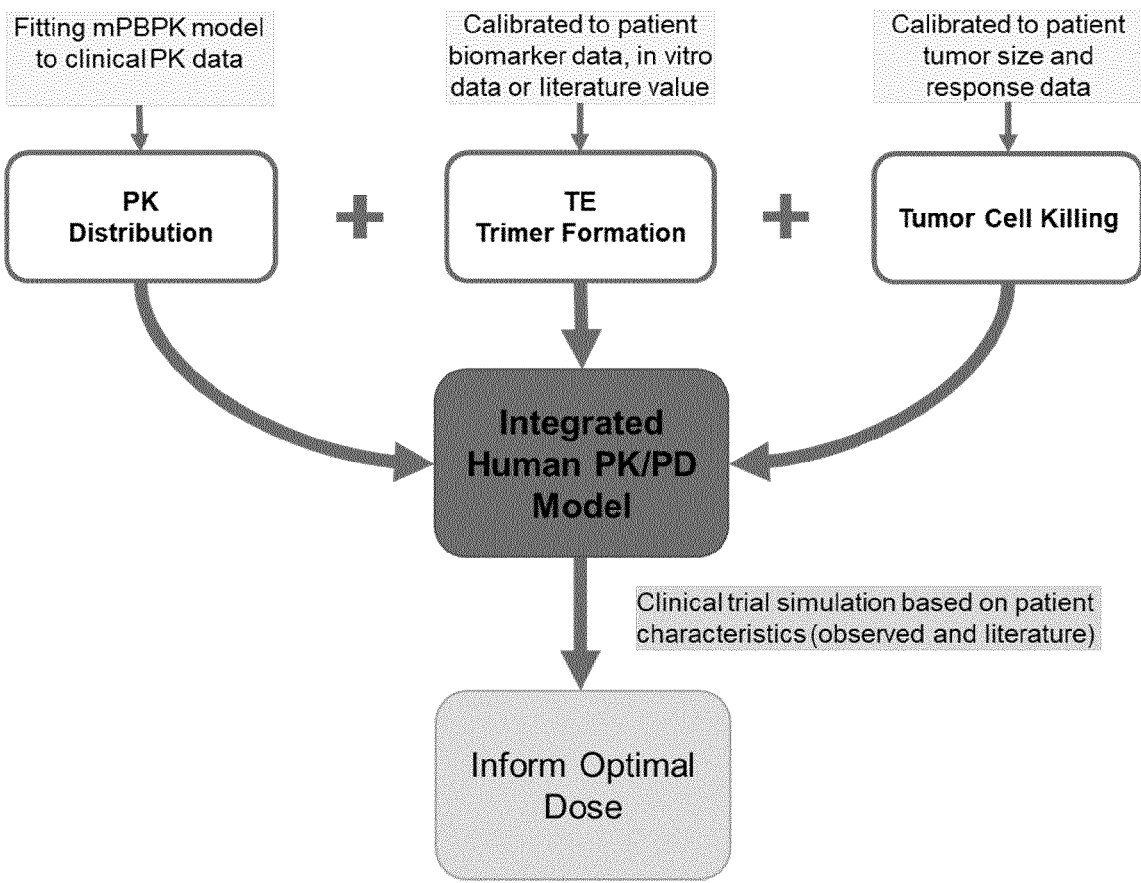

FIG. 2: Human PK/PD modeling analysis overview.

Figure 3:
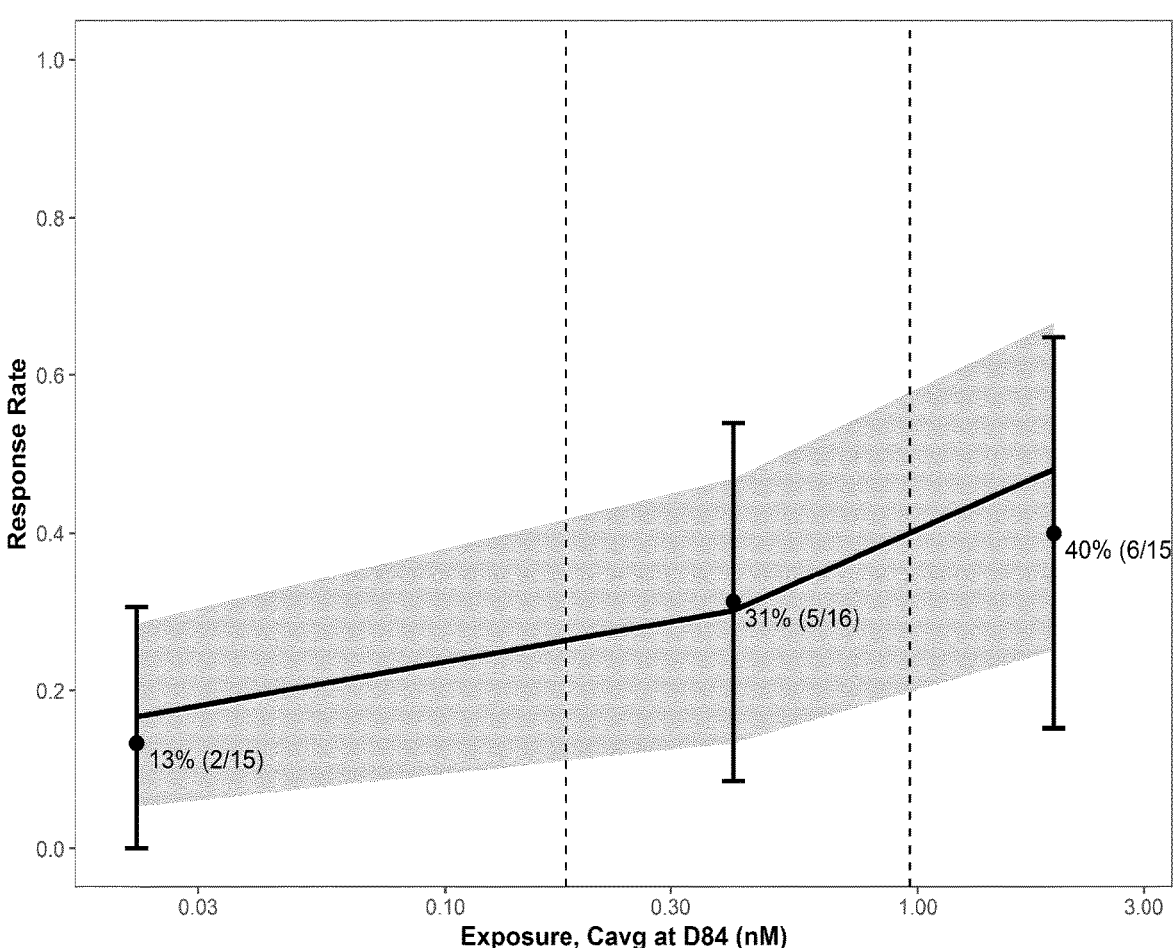

FIG. 3: Comparison of observed and calibrated model predicted epcoritamab dose escalation trial response rate. Observed epcoritamab dose escalation trial response rate and 90% CI as function of epcoritamab exposure tertile is shown by close circle and error bar respectively. Model predicted trial response rate and 90% prediction interval is show by solid line and shaded region.

Figure 4:
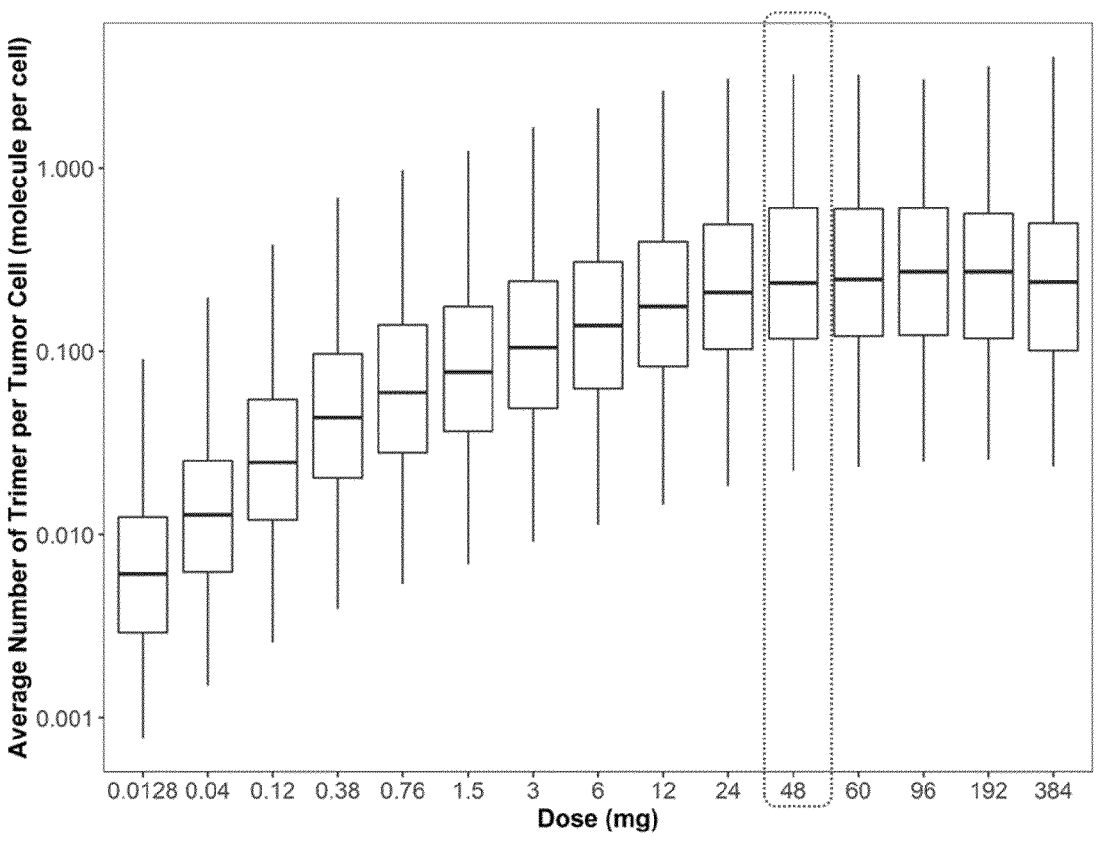

FIG. 4: Integrated PK/PD Model Predicted Trimer Formation for FL. For each dose, 100 virtual patients for simulations and the model predicted average number of trimer formed over the first 84 days, normalized by number of tumor cells, were summarized with box and whisker plot, representing median (middle horizontal bar), $25^{th}$ and $75^{th}$ percentile (lower and upper hinges), 1.5*inter-quartile range (whisker), and outliers (points).

Figure 5:
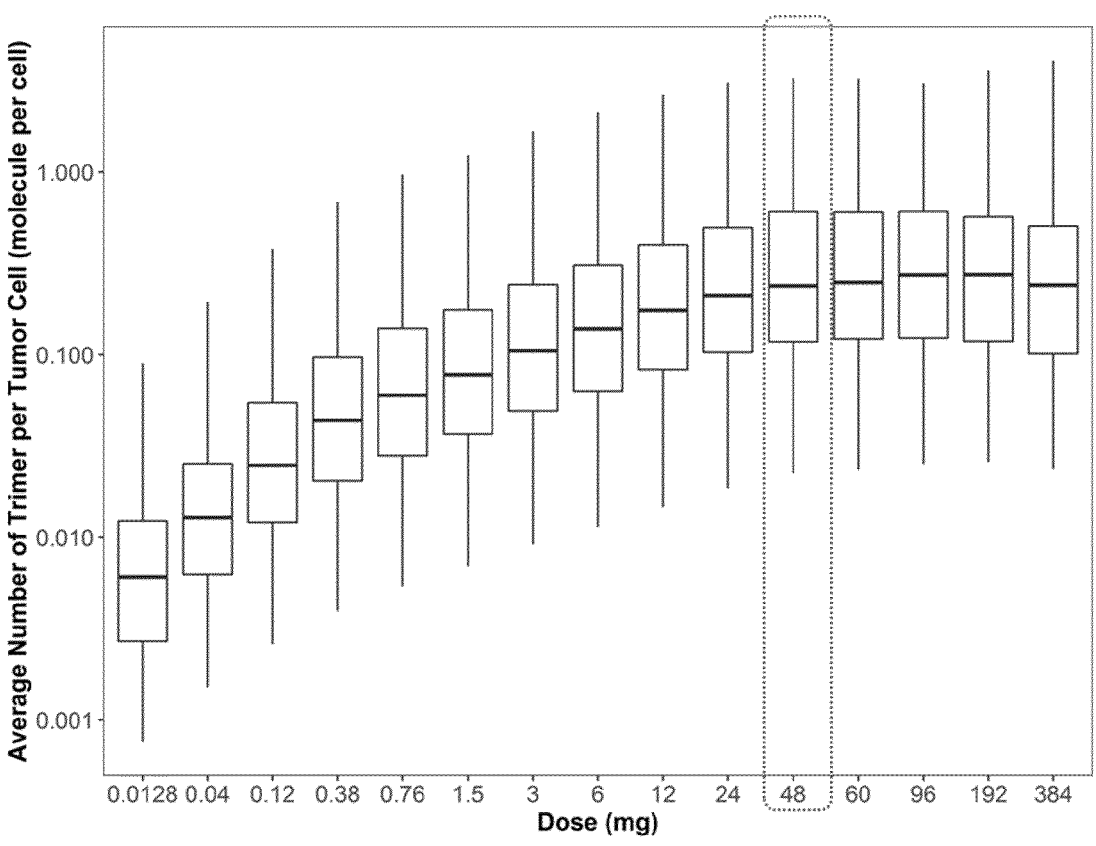

FIG. 5: Integrated Pharmacokinetic/Pharmacodynamic Model Predicted Trimer Formation for DLBCL/HGBCL. For each dose, 100 virtual patients in an epcoritamab expansion trial were simulated and the model predicted average number of trimer formed over the first 84 days, normalized by number of tumor cells, were summarized with box and whisker plot.

Figure 6:
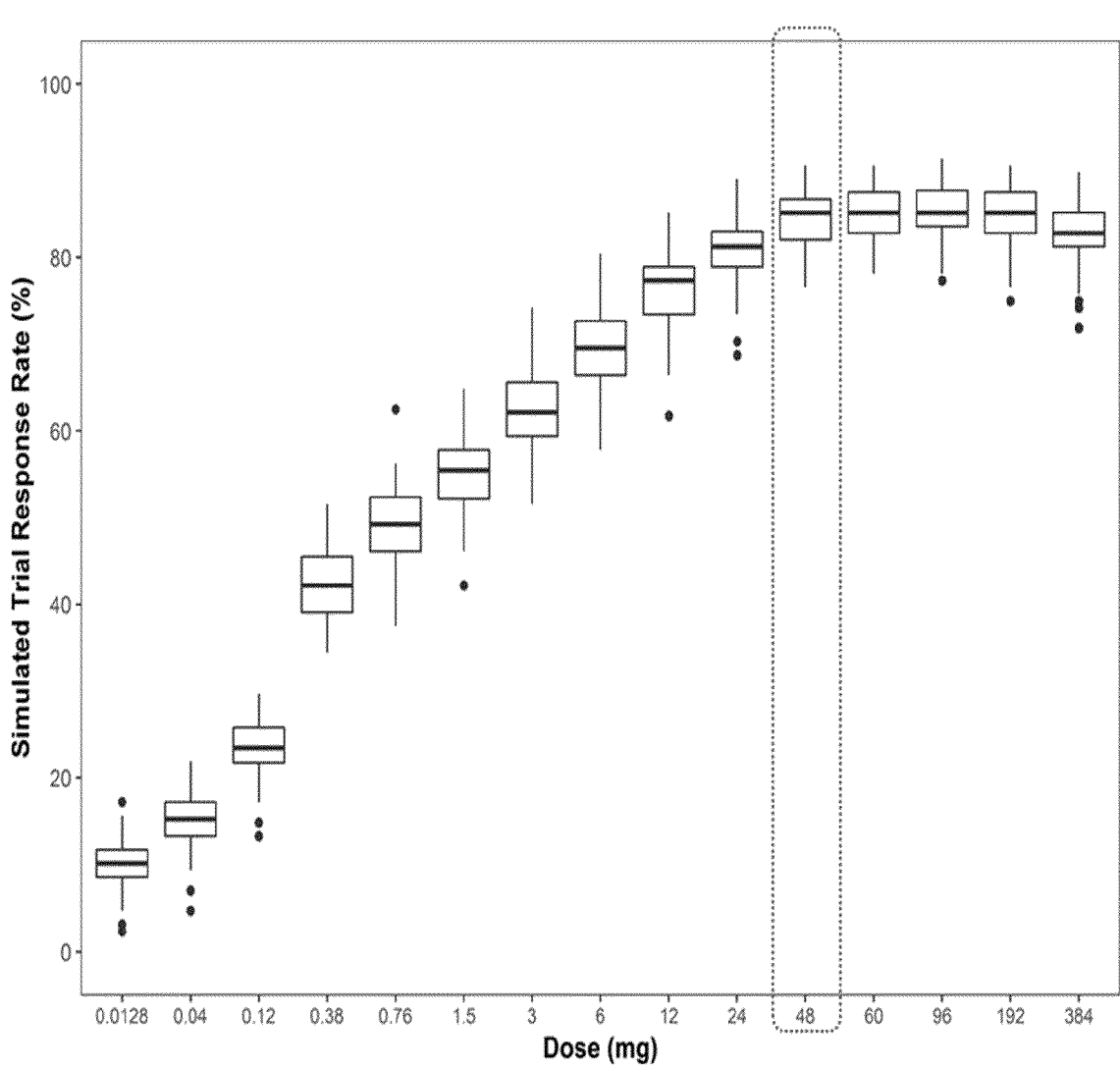

FIG. 6: Integrated PK/PD model predicted epcoritamab expansion trial response rate for FL patients. For each dose, 100 virtual patients in an epcoritamab expansion trial were simulated and the model predicted trial response rate were summarized with box and whisker plot, representing median (middle horizontal bar), $25^{th}$ and $75^{th}$ percentile (lower and upper hinges), 1.5*inter-quartile range (whisker), and outliers (points).

Figure 7:
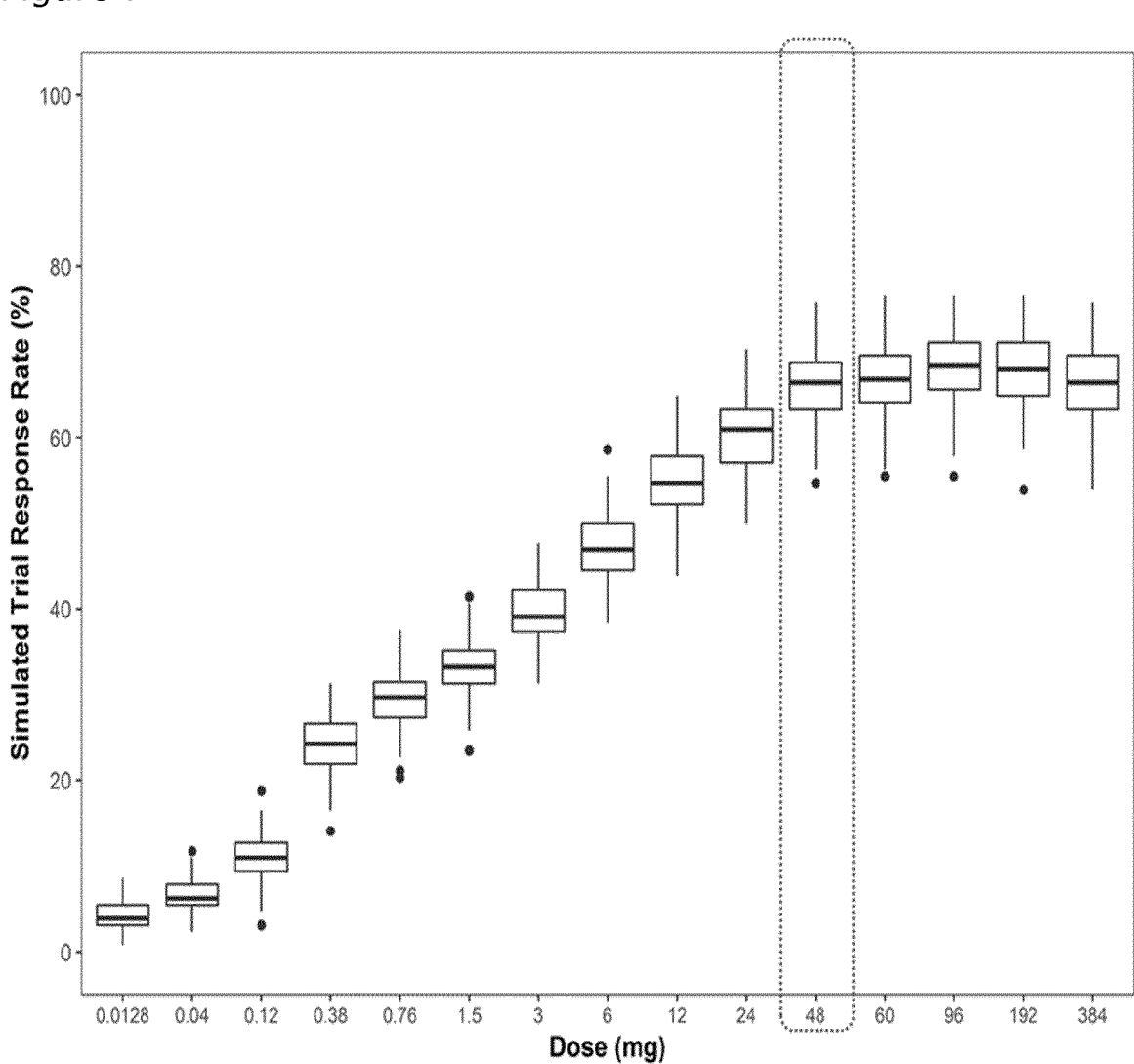

FIG. 7: Integrated PK/PD model predicted epcoritamab expansion trial response rate for DLBCL/HGBCL patients. For each dose, 100 virtual patients in an epcoritamab expansion trial were simulated and the model predicted trial response rate were summarized with box and whisker plot, representing median (middle horizontal bar), $25^{th}$ and $75^{th}$ percentile (lower and upper hinges), 1.5*inter-quartile range (whisker), and outliers (points).

DETAILED DESCRIPTION

The term "immunoglobulin" herein refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH or $V_H$) and a heavy chain constant region (abbreviated herein as CH or $C_H$). The heavy chain constant region typically is comprised of three domains, CH1, CH2, and CH3. The hinge region is the region between the CH1 and CH2 domains of the heavy chain and is highly flexible. Disulphide bonds in the hinge region are part of the interactions between two heavy chains in an IgG molecule. Each light chain typically is comprised of a light chain variable region (abbreviated herein as VL or $V_L$) and a light chain constant region (abbreviated herein as CL or $C_L$). The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules (Brochet X., Nucl Acids Res. 2008; 36: W503-508 and Lefranc M P., Nucleic Acids Research 1999; 27:209-212; see also internet http address http://www.imgt.org/). Unless otherwise stated or contradicted by context, reference to amino acid positions in the constant regions in the present invention is according to the EU-numbering (Edelman et al., Proc Natl Acad Sci USA. 1969 May; 63(1):78-85; Kabat et al., Sequences of Proteins of Immunological Interest, Fifth Edition. 1991 NIH Publication No.

91-3242). For example, SEQ ID NO: 15 herein sets forth amino acids positions 118-447 according to EU numbering, of the IgG1 heavy chain constant region.

The term "amino acid corresponding to position . . . " as used herein refers to an amino acid position number in a human IgG1 heavy chain. Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The term "antibody-binding region", as used herein, refers to the region which interacts with the antigen and comprises both the VH and the VL regions. The term antibody when used herein comprises not only monospecific antibodies, but also multispecific antibodies which comprise multiple, such as two or more, e.g. three or more, different antigen-binding regions. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the VL, VH, CL and CH1 domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., Nature 341, 544-546 (1989)), which consists essentially of a VH domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. As used herein, the term "isotype" refers to the immunoglobulin class (for instance IgG1, IgG2, IgG3, IgG4, IgD, IgA, IgE, or IgM) that is encoded by heavy chain constant region genes. When a particular isotype, e.g. IgG1, is mentioned herein, the term is not limited to a specific isotype sequence, e.g. a particular IgG1 sequence, but is used to indicate that the antibody is closer in sequence to that isotype, e.g. IgG1, than to other isotypes. Thus, e.g. an IgG1 antibody of the invention may be a sequence variant of a naturally-occurring IgG1 antibody, including variations in the constant regions.

The term "monoclonal antibody" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

The term "bispecific antibody" or "bs" or "bsAb" in the context of the present invention refers to an antibody having two different antigen-binding regions defined by different antibody sequences. A bispecific antibody can be of any format.

When used herein, the terms "half molecule", "Fab-arm" and "arm" refer to one heavy chain-light chain pair.

When a bispecific antibody is described to comprise a half-molecule antibody "derived from" a first parental antibody, and a half-molecule antibody "derived from" a second parental antibody, the term "derived from" indicates that the bispecific antibody was generated by recombining, by any known method, said half-molecules from each of said first and second parental antibodies into the resulting bispecific antibody. In this context, "recombining" is not intended to be limited by any particular method of recombining and thus includes all of the methods for producing bispecific antibodies described herein below, including for example recombining by half-molecule exchange (also known as "controlled Fab-arm exchange"), as well as recombining at nucleic acid level and/or through co-expression of two half-molecules in the same cells.

The term "full-length" when used in the context of an antibody indicates that the antibody is not a fragment but contains all of the domains of the particular isotype normally found for that isotype in nature, e.g. the VH, CH1, CH2, CH3, hinge, VL and CL domains for an IgG1 antibody. A full-length antibody may be engineered. An example of a "full-length" antibody is epcoritamab.

When used herein, unless contradicted by context, the term "Fc region" refers to an antibody region consisting of the Fc sequences of the two heavy chains of an immunoglobulin, wherein said Fc sequences comprise at least a hinge region, a CH2 domain, and a CH3 domain.

When used herein the term "heterodimeric interaction between the first and second CH3 regions" refers to the interaction between the first CH3 region and the second CH3 region in a first-CH3/second-CH3 heterodimeric protein.

When used herein the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific).

The term "$K_D$" (M), as used herein, refers to the dissociation equilibrium constant of a particular antibody-antigen interaction. Affinity, as used herein, and $K_D$ are inversely related, that is that higher affinity is intended to refer to lower $K_D$, and lower affinity is intended to refer to higher $K_D$.

In a preferred embodiment, the antibody of the invention is isolated. An "isolated antibody" as used herein, is intended to refer to an antibody which is substantially free of other antibodies having different antigenic specificities. In a preferred embodiment, an isolated bispecific antibody that specifically binds to CD20 and CD3 is in addition substantially free of monospecific antibodies that specifically bind to CD20 or CD3.

The term "CD3" as used herein, refers to the human Cluster of Differentiation 3 protein which is part of the T-cell co-receptor protein complex and is composed of four distinct chains. CD3 is also found in other species, and thus, the term "CD3" is not limited to human CD3 unless contradicted by context. In mammals, the complex contains a CD3γ (gamma) chain (human CD3γ chain UniProtKB/Swiss-Prot No P09693, or cynomolgus monkey CD3γ UniProtKB/Swiss-Prot No Q95LI7), a CD3δ (delta) chain (human CD36 UniProtKB/Swiss-Prot No P04234, or cynomolgus monkey CD3δ UniProtKB/Swiss-Prot No Q95LI8), two CD3ε (epsilon) chains (human CD3ε UniProtKB/Swiss-Prot No P07766; cynomolgus CD3ε UniProtKB/Swiss-Prot No Q95LI5; or rhesus CD3ε UniProtKB/Swiss-Prot No G7NCB9), and a CD3ζ-chain (zeta) chain (human CD3ζ UniProtKB/Swiss-Prot No P20963, cynomolgus monkey CD3ζ UniProtKB/Swiss-Prot No Q09TK0). These chains associate with a molecule known as the T-cell receptor (TCR) and generate an activation signal in T lymphocytes. The TCR and CD3 molecules together comprise the TCR complex.

A "CD3 antibody" or "anti-CD3 antibody" is an antibody which binds specifically to the antigen CD3, in particular human CD3ε (epsilon).

The term "human CD20" or "CD20" refers to human CD20 (UniProtKB/Swiss-Prot No P11836) and includes any variants, isoforms and species homologs of CD20 which are naturally expressed by cells, including tumor cells, or are expressed on cells transfected with the CD20 gene or cDNA. Species homologs include rhesus monkey CD20 (*Macaca mulatta*; UniProtKB/Swiss-Prot No H9YXP1) and cynomolgus monkey CD20 (*Macaca fascicularis*; UniProtKB No G7PQ03).

A "CD20 antibody" or "anti-CD20 antibody" is an antibody which binds specifically to the antigen CD20, in particular to human CD20.

A "CD3×CD20 antibody", "anti-CD3×CD20 antibody", "CD20×CD3 antibody" or "anti-CD20×CD3 antibody" is a bispecific antibody, which comprises two different antigen-binding regions, one of which binds specifically to the antigen CD20 and one of which binds specifically to CD3.

"DuoBody-CD3×CD20" herein refers to an IgG1 bispecific CD3×CD20 antibody comprising a first heavy and light chain pair as defined in SEQ ID NO:24 and SEQ ID NO:25, respectively, and comprising a second heavy and light chain pair as defined in SEQ ID NO:26 and SEQ ID NO:27. The first heavy and light chain pair comprises a binding region binding to human CD3ε (epsilon), the second heavy and light chain pair comprises a binding region binding to human CD20. The first binding region comprising the VH and VL sequences as defined by SEQ ID NO. 6 and 7, and the second binding region comprising the VH and VL sequences as defined by SEQ ID NO. 13 and 14. This bispecific antibody can be prepared as described in WO 2016/110576.

The present invention also provides antibodies comprising functional variants of the heavy chain, light chains, VL regions, VH regions, or one or more CDRs of the antibodies of the examples. A functional variant of a heavy chain, a light chain, VL, VH, or CDRs used in the context of an antibody still allows the antibody to retain at least a substantial proportion (at least about 90%, 95% or more) of functional features of the "reference" and/or "parent" antibody, including affinity and/or the specificity/selectivity for particular epitopes of CD20 and/or CD3, Fc inertness and PK parameters such as half-life, Tmax, Cmax.

Such functional variants typically retain significant sequence identity to the parent antibody and/or have substantially similar length of heavy and light chains. The percent identity between two sequences is a function of the number of identical positions shared by the sequences (i.e., % homology=# of identical positions/total # of positions× 100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

Exemplary variants include those which differ from heavy and/or light chains, VH and/or VL and/or CDR regions of the parent antibody sequences mainly by conservative substitutions; for instance, 10, such as 9, 8, 7, 6, 5, 4, 3, 2 or 1 of the substitutions in the variant may be conservative amino acid residue replacements.

In the context of the present invention, conservative substitutions may be defined by substitutions within the classes of amino acids reflected in the following table:

Amino Acid Residue Classes for Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Lysine with Arginine in position 409 is designated as: K409R, and the substitution of Lysine with any amino acid residue in position 409 is designated as K409X. In case of deletion of Lysine in position 409 it is indicated by K409*.

The term "epitope" means a protein determinant capable of specific binding to an antibody. Epitopes usually consist of surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen binding peptide (in other words, the amino acid residue is within the footprint of the specifically antigen binding peptide).

The term "chimeric antibody" as used herein, refers to an antibody wherein the variable region is derived from a non-human species (e.g. derived from rodents) and the constant region is derived from a different species, such as human. Chimeric monoclonal antibodies for therapeutic applications are developed to reduce antibody immunogenicity. The terms "variable region" or "variable domain" as used in the context of chimeric antibodies, refer to a region which comprises the CDRs and framework regions of both the heavy and light chains of the immunoglobulin. Chimeric antibodies may be generated by using standard DNA techniques as described in Sambrook et al., 1989, Molecular Cloning: A laboratory Manual, New York: Cold Spring Harbor Laboratory Press, Ch. 15. The chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. The VH and VL of the CD3 arm that is used herein in Duobody-CD3×CD20 represents a humanized antigen-binding region. Optionally, additional amino acid modifications, which are not necessarily back-mutations, may be applied to obtain a humanized antibody with preferred characteristics, such as affinity and biochemical properties.

The term "human antibody" as used herein, refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The VH and VL of the CD20 arm that is used herein in Duobody-CD3×CD20 represents a human antigen-binding region. Human monoclonal antibodies of the invention can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes. A suitable animal system for preparing hybridomas that secrete human monoclonal antibodies is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known. Human monoclonal antibodies can thus e.g. be generated using transgenic or transchromosomal mice or rats carrying parts of the human immune system rather than the mouse or rat system. Accordingly, in one embodiment, a human antibody is obtained from a transgenic animal, such as a mouse or a rat, carrying human germline immunoglobulin sequences instead of animal immunoglobulin sequences. In such embodiments, the antibody originates from human germline immunoglobulin sequences introduced in the animal, but the final antibody sequence is the result of said human germline immunoglobulin sequences being further modified by somatic hypermutations and affinity maturation by the endogenous animal antibody machinery, see e.g. Mendez et al. 1997 Nat Genet. 15(2):146-56. The VH and VL of the CD20 arm that is used herein in Duobody-CD3×CD20 represents a human antigen-binding region.

The term "reducing conditions" or "reducing environment" refers to a condition or an environment in which a substrate, here a cysteine residue in the hinge region of an antibody, is more likely to become reduced than oxidized.

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO, CHO—S, HEK, HEK293, HEK-293F, Expi293F, PER.C6 or NS0 cells, and lymphocytic cells.

The term "treatment" refers to the administration of an effective amount of a therapeutically active antibody of the present invention with the purpose of easing, ameliorating, arresting or eradicating (curing) symptoms or disease states.

The term "effective amount" or "therapeutically effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

The term "buffer" as used herein denotes a pharmaceutically acceptable buffer. The term "buffer" encompasses those agents which maintain the pH value of a solution, e.g., in an acceptable range and includes, but is not limited to, acetate, histidine, TRIS® (tris (hydroxymethyl)aminomethane), citrate, succinate, glycolate and the like. Generally, the "buffer" as used herein has a pKa and buffering capacity suitable for the pH range of about 5 to about 6, preferably of about 5.5.

A "surfactant" as used herein is a compound that is typically used in pharmaceutical formulations to prevent drug adsorption to surfaces and or aggregation. Furthermore, surfactants lower the surface tension (or interfacial tension) between two liquids or between a liquid and a solid. For example, an exemplary surfactant can significantly lower the surface tension when present at very low concentrations (e.g., 5% w/v or less, such as 3% w/v or less, such as 1% w/v or less such as 0.4% w/v or less, such as below 0.1% w/v or less, such as 0.04% w/v). Surfactants are amphiphilic, which means they are usually composed of both hydrophilic and hydrophobic or lipophilic groups, thus being capable of forming micelles or similar self-assembled structures in aqueous solutions. Known surfactants for pharmaceutical use include glycerol monooleate, benzethonium chloride, sodium docusate, phospholipids, polyethylene alkyl ethers, sodium lauryl sulfate and tricaprylin (anionic surfactants); benzalkonium chloride, citrimide, cetylpyridinium chloride and phospholipids (cationic surfactants); and alpha tocopherol, glycerol monooleate, myristyl alcohol, phospholipids, poloxamers, polyoxyethylene alkyl ethers, polyoxyethylene castor oil derivatives, polyoxyethylene sorbitan fatty acid esters, polyoxyethylene stearates, polyoxyl hydroxystearate, polyoxylglycerides, polysorbates such as polysorbate 20 or polysorbate 80, propylene glycol dilaurate, propylene glycol monolaurate, sorbitan esters sucrose palmitate, sucrose stearate, tricaprylin and TPGS (Nonionic and zwitterionic surfactants).

A "diluent" of interest herein is one which is pharmaceutically acceptable (safe and non-toxic for administration to a human) and is useful for the preparation of dilutions of the pharmaceutical composition. Preferably such dilutions of the composition of the invention dilute only the antibody concentration but not the buffer and stabilizer. Accordingly, in a preferred embodiment the diluent contains the same concentrations of the buffer and stabilizer as is present in the pharmaceutical composition of the invention. Further exemplary diluents include sterile water, bacteriostatic water for injection (BWFI), a pH buffered solution which is preferably an acetate buffer, sterile saline solution, Ringer's solution or dextrose solution. In a preferred embodiment the diluent comprises or consists essentially of acetate buffer and sorbitol.

The terms "pharmaceutical composition" and "pharmaceutical formulation" is used interchangeably herein.

Embodiments

In one aspect, the current invention provides for a method of treating a B-cell non-Hodgkin lymphoma (B-NHL) in a human subject, the method comprising administering subcutaneously (sc) to a subject in need thereof, a bispecific antibody comprising (i) a first binding arm comprising a first antigen-binding region binding to human CD3ε (epsilon), comprising a variable heavy chain region and a variable light chain region wherein the variable heavy chain region comprises the CDR1, CDR2 and CDR3 sequences of SEQ ID NO:6; and wherein the variable light chain region comprises the CDR1, CDR2 and CDR3 sequences of SEQ ID NO: 7; and (ii) a second binding arm comprising a second antigen-binding region binding to human CD20, comprising a variable heavy chain region and a variable light chain region wherein the variable heavy chain region comprises the CDR1, CDR2 and CDR3 sequences of SEQ ID No: 13; and wherein the variable light chain region comprises the CDR1, CDR2 and CDR3 sequences of SEQ ID No: 14;

wherein said bispecific antibody is administered at a dose of at least 24 mg.

In another aspect, the current invention provides for a method of treating an B-cell non-Hodgkin lymphoma (B-NHL) in a human subject, the method comprising administering subcutaneously to a subject in need thereof, a bispecific antibody, which is a full length antibody with an inert Fc region, comprising (i) a first binding arm comprising a first antigen-binding region binding to human CD3ε (epsilon), comprising a variable heavy chain region and a variable light chain region wherein the variable heavy chain region comprises the CDR1, CDR2 and CDR3 sequences of SEQ ID NO:6; and wherein the variable light chain region comprises the CDR1, CDR2 and CDR3 sequences of SEQ ID NO: 7; and (ii) a second binding arm comprising a second antigen-binding region binding to human CD20, comprising a variable heavy chain region and a variable light chain region wherein the variable heavy chain region comprises the CDR1, CDR2 and CDR3 sequences of SEQ ID No: 13; and wherein the variable light chain region comprises the CDR1, CDR2 and CDR3 sequences of SEQ ID No: 14;

wherein said bispecific antibody is administered at a dose of at least 24 mg.

In yet another aspect, the current invention provides for a method of treating an B-cell non-Hodgkin lymphoma (B-NHL) in a human subject, the method comprising administering subcutaneously to a subject in need thereof, a bispecific antibody, which is a full length antibody, comprising (i) a first binding arm comprising a first antigen-binding region binding to human CD3ε (epsilon), comprising a variable heavy chain region and a variable light chain region wherein the variable heavy chain region comprises the CDR1, CDR2 and CDR3 sequences of SEQ ID NO:6; and wherein the variable light chain region comprises the CDR1, CDR2 and CDR3 sequences of SEQ ID NO: 7; and (ii) a second binding arm comprising a second antigen-binding region binding to human CD20, comprising a variable heavy chain region and a variable light chain region wherein the variable heavy chain region comprises the CDR1, CDR2 and CDR3 sequences of SEQ ID No: 13; and wherein the variable light chain region comprises the CDR1, CDR2 and CDR3 sequences of SEQ ID No: 14;

wherein said bispecific antibody is administered at a dose of at least 24 mg.

In another aspect, the current invention provides for a method of treating an B-cell non-Hodgkin lymphoma (B-NHL) in a human subject, the method comprising administering subcutaneously to a subject in need thereof, a bispecific antibody, which comprises an inert Fc region, comprising (i) a first binding arm comprising a first antigen-binding region binding to human CD3ε (epsilon), comprising a variable heavy chain region and a variable light chain region wherein the variable heavy chain region comprises the CDR1, CDR2 and CDR3 sequences of SEQ ID NO:6; and wherein the variable light chain region comprises the CDR1, CDR2 and CDR3 sequences of SEQ ID NO: 7; and (ii) a second binding arm comprising a second antigen-binding region binding to human CD20, comprising a variable heavy chain region and a variable light chain region wherein the variable heavy chain region comprises the CDR1, CDR2 and CDR3 sequences of SEQ ID No: 13; and wherein the variable light chain region comprises the CDR1, CDR2 and CDR3 sequences of SEQ ID No: 14;

wherein said bispecific antibody is administered at a dose of at least 24 mg.

It is understood that when herein reference is made to methods of treatments, i.e. a method of treating a B-cell non-Hodgkin lymphoma (B-NHL) in a human subject, which method comprises administering subcutaneously to a human subject in need thereof, a bispecific antibody in accordance with the invention, which preferably is a full length antibody and/or comprises an inert Fc region, phrased differently, reference is made as well to bispecific antibodies in accordance with the invention, for use in the treatment of a B-cell non-Hodgkin lymphoma (B-NHL) in a human subject, which use comprises administering subcutaneously to a human subject in need thereof, a bispecific antibody in accordance with the invention, which preferably is a full length antibody and/or comprises an inert Fc region. Hence, wherein reference is made herein to methods for treatment of B-NHL with a bispecific antibody targeting CD3 and CD20 as defined herein, reference is also made to said bispecific antibody targeting CD3 and CD20 for use in the treatment of B-NHL in a human subject.

In a further aspect, the current invention provides for a method of treating a B-NHL, wherein said bispecific antibody comprises:

(i) a first binding arm comprising a first antigen-binding region binding to human CD3ε (epsilon), wherein said first antigen-binding region comprises a heavy chain variable (VH) region CDR1, CDR2, and CDR3 having the sequences as set forth in SEQ ID NOs. 1, 2, and 3, respectively, and a light chain variable (VL) region CDR1, CDR2, and CDR3 having the sequences as set forth in SEQ ID NO. 4, the sequence GTN, and the sequence as set forth in SEQ ID NO. 5, respectively, and (ii) a second binding arm comprising a second antigen-binding region binding to human CD20, wherein said second antigen-binding region comprises a heavy chain variable (VH) region CDR1, CDR2, and CDR3 having the sequences as set forth in SEQ ID NOs. 8, 9, and 10, respectively, and a light chain variable (VL) region CDR1, CDR2, and CDR3 having the sequences as set forth in SEQ ID NO. 11, the sequence DAS, and the sequence as set forth in SEQ ID NO. 12, respectively.

In still a further aspect, the current invention provides for a method of treating a B-NHL, wherein said bispecific antibody comprises:

(i) a first binding arm comprising a first antigen-binding region binding to human CD3ε (epsilon), comprising a variable heavy chain region and a variable light chain region wherein the variable heavy chain region comprises SEQ ID NO:6; and wherein the variable light chain region comprises SEQ ID NO:7; and (ii) a second binding arm comprising a second antigen-binding region binding to human CD20, comprising a variable heavy chain region and a variable light chain region wherein the variable heavy chain region comprises SEQ ID No: 13; and wherein the variable light chain region comprises SEQ ID No:14.

Non-Hodgkin Lymphoma's (NHLs) represent a disease entity characterized by malignant transformation of the cells from lymphoid tissue. NHLs of B-cell origin ("B-NHL" or "B-cell NHL") as defined herein constitute a diverse set of neoplasms within the larger context of NHL. These are diagnosed, and distinction of B-NHL subtypes determined, using standard classification criteria by a pathologist (based on tissue biopsy), including morphologic features by histology, surface markers (immunohistochemistry/flow cytometry), chromosomal abnormalities/translocations (karyotyping, fluorescence in situ hybridization (FISH)), and molecular (gene mutation) findings. B-NHLs are diagnosed and classified based on WHO classification, which is included herein by reference (Swerdlow S H, Campo E, Harris N L, et al. WHO Classification of Tumours of Haematopoietic and Lymphoid Tissues (Revised ed. 4th). Lyon, France: IARC Press (2017); Swerdlow S H, Campo E, Harris N L, et al. WHO Classification of Tumours of Haematopoietic and Lymphoid Tissues (ed. 4th). Lyon, France: IARC Press (2008)).

Briefly, B-NHLs are typically divided into indolent (slow-growing) and aggressive subtypes. Aggressive B-NHLs have high Ki67 expression, whereas indolent B-NHLs have relatively low Ki67 expression. As a generalization, indolent lymphomas respond to treatment and are kept under control (in remission) with long-term survival of many years but are not cured. Aggressive lymphomas usually require intensive treatments, with some having a good prospect for a permanent cure. Aggressive B-NHL includes: Diffuse large B-cell lymphoma (DLBCL), high-grade B-cell lymphoma (HGBCL), primary mediastinal large B-cell lymphoma (PMBCL), mantle cell lymphoma (MCL). Indolent B-NHL includes follicular lymphoma (FL), marginal-zone lymphoma (MZL) and small lymphocytic lymphoma (SLL). Diffuse large B-cell lymphoma (DLBCL) is the most common type of NHL accounting for approximately 30% to 40% of all NHL diagnoses, followed by FL (20% to 25% of all NHL diagnoses). The majority of the B-cell lymphomas express B-cell markers, such as CD19, CD20, CD22, and CD79b. The biologic heterogeneity of B-cell malignancies is reflected in the clinical course and outcome of individual diseases. Indolent diseases such as FL, MZL, and SLL evolve slowly, with a median survival of 8 to 10 years. In contrast, more aggressive diseases such as DLBCL/HGBCL, if left untreated, have a median survival of 6 months. The median age at diagnosis for most patients with lymphoma is approximately 60 to 65 years (WHO, 2008).

Hence, the method in accordance with the invention further comprises the treatment of B-NHL, wherein said B-NHL is selected from the group consisting of diffuse large B-cell lymphoma (DLBCL), high-grade B-cell lymphoma (HGBCL), primary mediastinal large B-cell lymphoma (PMBCL), mantle cell lymphoma (MCL), follicular lymphoma (FL), marginal-zone lymphoma (MZL) and small lymphocytic lymphoma (SLL).

In another aspect, the method in accordance with the invention as provided herein comprises the treatment of FL, HGBCL, or DLBCL. In yet another aspect, the method in accordance with the invention as provided herein comprises the treatment of FL. In another aspect, the method in accordance with the invention as provided herein comprises the treatment of HGBCL. In still another aspect, the method in accordance with the invention as provided herein comprises the treatment of DLBCL. In another further aspect, the method in accordance with the invention as provided herein comprises the treatment of HGBCL and/or DLBCL. In yet another aspect, the method in accordance with the invention as provided herein comprises the treatment of FL, MCL, HGBCL, or DLBCL. In another aspect, the method in accordance with the invention as described herein comprises the treatment of MCL.

"DLBCL/HGBCL" or "DLBCL and HGBCL" or, "DLBCL or HGBCL" as defined herein refers to B-NHL classified as either diffuse large B-cell lymphoma or high-grade B-cell lymphoma, in accordance with the WHO classification as defined in Swerdlow S H, Campo E, Harris N L, et al. WHO Classification of Tumours of Haematopoietic and Lymphoid Tissues (ed. 4th). Lyon, France: IARC Press (2008) and Swerdlow S H, Campo E, Harris N L, et al. WHO Classification of Tumours of Haematopoietic and Lymphoid Tissues (Revised ed. 4th). Lyon, France: IARC Press (2017), which are incorporated herein by reference.

"FL", i.e. follicular lymphoma, as defined herein refers to B-NHL which originates from specific types of B-cells known as centrocytes and centroblasts that typically form follicular or follicle-like structures. FL typically has a slow disease course which persists essentially unchanged for years. FL can be classified in accordance with the WHO classification as defined in Swerdlow S H, Campo E, Harris N L, et al. WHO Classification of Tumours of Haematopoietic and Lymphoid Tissues (ed. 4th). Lyon, France: IARC Press (2008) and Swerdlow S H, Campo E, Harris N L, et al. WHO Classification of Tumours of Haematopoietic and Lymphoid Tissues (Revised ed. 4th). Lyon, France: IARC Press (2017), which are incorporated herein by reference.

"MCL", i.e. Mantle cell lymphoma, comprises B-cell lymphoma with chromosomal translocation t(11; 14) leading to expression of cyclin D1, also including CD5+. MCL as defined herein includes B-NHL classified as MCL in accordance with the WHO classification as defined in Swerdlow S H, Campo E, Harris N L, et al. WHO Classification of Tumours of Haematopoietic and Lymphoid Tissues (ed. 4th). Lyon, France: IARC Press (2008) and Swerdlow S H, Campo E, Harris N L, et al. WHO Classification of Tumours of Haematopoietic and Lymphoid Tissues (Revised ed. 4th). Lyon, France: IARC Press (2017), which are incorporated herein by reference.

With regard to the dose of at least 24 mg of the bispecific antibody that is to be administered, or any other specified dose, it is understood that this amount refers to the amount of a bispecific antibody representing a full-length antibody, such as epcoritamab as defined in the example section. Hence, phrased differently, one may refer to administering a dose of a bispecific antibody of at least 24 mg as administering a dose of a bispecific antibody in accordance with the invention, wherein said dose corresponds to a dose of at least 24 mg dose of epcoritamab. One can determine the amount of antibody to be administered when for example, antibodies would be used differing substantially in molecular weight from the molecular weight of a full-length antibody such as epcoritamab. The amount of antibody thus required as defined herein can be calculated by dividing the molecular weight of the antibody by the weight of a full-length antibody such as epcoritamab and multiplying the outcome thereof with the specified dose as described herein. As long as the bispecific antibody has highly similar features as Duobody CD3×CD20, with regard to plasma half-life, Fc inertness, and/or binding region features for CD3 and CD20, i.e. with regard to CDRs and epitope binding features, e.g. a functional variant of Duobody CD3×CD20, such antibodies may be contemplated in accordance with the invention and administered at a dose corresponding with the dose as defined herein for a full-length antibody such as epcoritamab.

As said, the bispecific antibody binding to CD3 and CD20 is to be administered subcutaneously. The bispecific antibody hence is formulated in a pharmaceutical composition such that it is compatible with subcutaneous (s.c.) administration, i.e. having a formulation and/or concentration that allows pharmaceutical acceptable s.c. administration at the selected doses as defined herein. Preferably subcutaneous administration is carried out by injection. For example, formulations for Duobody CD3×CD20 that are compatible with subcutaneous formulation that can be contemplated have been described (e.g. as described in WO2019155008, which is incorporated herein by reference). Preferred formulations for the bispecific antibody in accordance with the invention may be formulated using sodium acetate trihydrate, acetic acid, sodium hydroxide, sorbitol, polysorbate 80, water for injection, having a pH of 5.5.

A suitable pharmaceutical composition for the bispecific antibody in accordance with the invention can comprise the bispecific antibody, 20-40 mM acetate, 140-160 mM sorbitol, and a surfactant, such as polysorbate 80, and having a pH of 5.3-5.6. A suitable pharmaceutical formulation for the bispecific antibody in accordance with the invention may comprise an antibody concentration in the range of 5-100 mg/mL, e.g. 48 or 60 mg/mL of the bispecific antibody, 30 mM acetate, 150 mM sorbitol, 0.04% w/v polysorbate 80, and having a pH of 5.5. Such a formulation may be appropriately diluted with e.g. the formulation buffer to allow proper dosing and subcutaneous administration. In any case, the volume of the pharmaceutical composition is appropriately selected to allow for subcutaneous administration of the antibody. For example, the volume to be administered is in the range of about 0.3 mL to about 3 mL, such as from 0.3 mL to 3 mL. The volume to be administered can be 0.5 mL, 0.8 mL, 1 mL, 1.2 mL, 1.5 ml, 1.7 mL, 2 mL, or 2.5 mL. The volume to be administered can be 0.5 mL. The volume to be administered can be 0.8 mL. The volume to be administered can be 1.2 mL. The volume to be administered can be 1.5 mL. The volume to be administered can be 1.7 mL. The volume to be administered can be 2 mL. The volume to be administered can be 2.5 mL. In one embodiment the preferred volume for s.c. administration is about 1 mL. In another embodiment the preferred volume for s.c. administration is 1 mL.

As said, the methods (or uses of CD3×CD20 antibodies) in accordance with the invention are for the treatment of human patients suffering from B-NHL. It is understood that the method in accordance with the invention may be the first, or may be part of the first treatment provided to such patients. However, patients may have been subjected to prior treatments of B-NHL. Prior treatments may include, one or more of chemotherapy, radiation therapy, immunotherapy, and targeted therapy, or combination hereof, but not may not be restricted thereto. Most commonly the standard of care comprises treatments with CD20 monoclonal antibodies, alkylating agents, and anthracycline, either alone or in combination. It is understood that methods and uses in accordance with the invention may also be used in combination with other suitable treatments.

For example, the most common chemotherapy combination for the first treatment of aggressive NHL is called CHOP and contains 4 medications: cyclophosphamide, doxorubicin, vincristine, and prednisone. Adding an anti-CD20 monoclonal antibody, such as rituximab, has been shown to be an improvement over CHOP alone, also referred to as R—CHOP. Induction with R—CHOP is standard of care in $1^{st}$ line treatment of DLBCL, as well as being one of more available $1^{st}$ standard of care treatments in FL. In DLBCL, $2^{nd}$ line treatments include intensive salvage treatment (rituximab/dexamethasone/high-dose cytarabine/cisplatin [R-DHAP], rituximab/ifosfamide/carboplatin/etoposide [R-ICE], or rituximab/gemcitabine/dexamethasone/cisplatin [R-GDP]) followed by, if chemosensitive, high-dose chemotherapy with autologous hematopoietic stem cell transplantation (HDT-ASCT). For DLBCL patients not being eligible to intensive salvage treatment and HDT-ASCT due to age or comorbidities, $2^{nd}$ line treatments include rituximab/gemcitabine/oxaliplatin (R-GemOx) and rituximab/bendamustine (RB). There are no clear standard of care for DLBCL late-line relapse, but interventions include allogeneic hematopoietic stem cell transplantation, lenalidomide, ibrutinib, and chimeric antigen receptor T (CAR-T) cell therapy (Chavez et al., Best Pract Res Clin Haematol, 2018 June; 31(2):135-146).

Hence, in a further embodiment, in a method in accordance with the invention, a human subject having B-NHL has received at least one line of treatment prior to the treatment in accordance with the invention. In another embodiment, a human subject having B-NHL has received one line of treatment prior to the treatment in accordance with the invention. In another further embodiment, a human subject having B-NHL has received two lines of treatment prior to the treatment in accordance with the invention. In still another further embodiment, a human subject having B-NHL has received three lines of treatment prior to the treatment in accordance with the invention. In yet another further embodiment, a subject having B-NHL has received more than three lines of treatment prior to the treatment in accordance with the invention. In another further embodiment, a subject having B-NHL has received one, two, three, or more lines of treatment prior to the treatment in accordance with the invention. In a further embodiment, a prior line of treatment comprises R—CHOP. In yet another further embodiment, a prior line treatment comprises a CAR-T cell therapy.

Human subjects having B-NHL are classified as having a CD20 positive cancer. Hence, prior cancer treatments such human subjects may have received include anti-CD20 mAbs, and may also include engineered T cells targeting CD20, e.g. a CAR-T therapy (Schuster S J, Bishop M R, Tam C S, et al. Tisagenlecleucel in adult relapsed or refractory diffuse large B-cell lymphoma. N Engl J Med. 2019; 380(1):45-56). During such treatments, or any other treatments, the B-NHL may be refractory or have relapsed to said treatment. Hence, in one aspect of the invention, said human subject has received prior to the treatment with the bispecific antibody a treatment with a CD20 monospecific antibody, such as rituximab. Furthermore, during said prior treatment with the CD20 monospecific antibody, the B-NHL cancer relapsed, or, the B-NHL cancer was refractory to said treatment. Such prior treatment with a CD20 monospecific antibody may be a treatment wherein the CD20 monospecific antibody was used in a combinatorial approach.

In a further embodiment, said bispecific antibody is administered at a dose of at least 40 mg. In another further embodiment, said bispecific antibody is administered at a dose in the range of between 30 mg to 100 mg, or between 35 mg and 90 mg. More preferably, in another further embodiment, said bispecific antibody is administered at a dose in the range of between 40 mg and 70 mg. In another further embodiment, said bispecific antibody is administered at a dose of at least 48 mg. In another further embodiment, said bispecific antibody is administered at a dose of at least 60 mg. It may also be contemplated to administer said bispecific antibody at a dose of 60 mg. In another embodiment, said bispecific antibody is administered at a dose of 72 mg. In yet another further embodiment, said bispecific antibody is administered at a dose of 84 mg.

In still a further embodiment, said bispecific antibody is administered at a dose of 40, 41, 42, 43, 44, 45, 46, 47, 48, 49, 50, 51, 52, 53, 54, 55, 56, 57, 58, 59, 60, 61, 62, 63, 64, 65, 66, 67, or 69 mg. In a preferred embodiment, said bispecific antibody is administered at a dose of 48 mg.

Said dose preferably is administered weekly, and preferably said dose is administered (at least) 4 times. After said weekly administration, one may reduce the interval of administration to an administration once every two weeks, also referred to as biweekly administration. Such biweekly administration may be performed (at least) 6 times. After said biweekly administration, the interval may be reduced further to once every four weeks. Such administration every four weeks may be performed for an extended period.

It is understood that herein the said dose as referred herein above, may also be referred to as a full or a flat dose in the scenarios above wherein e.g. the said weekly dose, said dose every two weeks and/or said dose every four weeks, is administered is at the same level. Hence, when a dose of 48 mg is selected, preferably, at e.g. each weekly administration, each biweekly administration, and each administration every four weeks, the same dose of 48 mg is administered each time. Prior to administering said dose (to which can be referred as full dose, or flat dose) a priming or a priming and subsequent intermediate (second priming) dose may be administered. This may be advantageous as it may allow for effectively mitigating CRS risk and severity, which is a side-effect that can occur during treatment with the bispecific antibody binding both CD3 and CD20 in accordance with the invention. Such priming, or priming and intermediate doses, are at a lower dose as compared with the flat or full dose.

Hence, in the method or use in accordance with the invention, prior to administering said weekly dose, a priming dose of said bispecific antibody may be administered. Said priming dose preferably is administered one week prior to administering the first dose of said weekly dose. A priming dose may be selected which is in the range of 20-2000 μg, preferably in the range of 50-1000 μg, more preferably in the range of 70-350 μg. A priming dose that may be selected is 80, 100, 120, 140, 160, 180, 200, 220, 240, 260, 280, 300, 320, 350, 400, 450, 500, 600, 700, 800, 900, or 1000 μg. A preferred priming dose that may be selected is 160 μg of the full-length bispecific antibody.

Also, in the method or use in accordance with the invention, after administering said priming dose and prior to administering said weekly dose, an intermediate dose of said bispecific antibody may be administered. Preferably, said priming dose is administered two weeks, and said intermediate dose is administered one week, before administering the first dose of said weekly dose. Said intermediate dose typically is selected from a range in between the priming dose and the flat or full dose. Said intermediate dose may be selected in the range of 200-8000 μg, or preferably in the range of 400-4000, more preferably in the range of 600-2000 μg. An intermediate dose that may be selected is 200, 300, 400, 500, 600, 700, 800, 900, 1000, 1100, 1200, 1300, 1400, 1500, or 1600 μg. A preferred intermediate dose that may be selected is 800 μg of the full-length bispecific antibody.

Accordingly, in another embodiment, advantageous dosing regimens that may be contemplated in the methods and uses of the invention may include administering the bispecific antibody subcutaneously in 28-day cycles, wherein on a) Day 1, 8, 15 and 22 the first cycle, a priming dose is administered at day 1, an intermediate dose at day 8, and a dose of 48 mg at days 15, 22; for the first cycle; on b) Day 1, 8, 15 and 22 of cycles 2-3, a dose of 48 mg is administered; on c) Day 1, 15 of cycles 4-9, a dose of 48 mg is administered; and on d) Day 1, of further subsequent cycles, a dose of 48 mg is administered.

In yet a further embodiment, an advantageous dosing regimen that may be contemplated in the methods and uses of the invention may include administering the bispecific antibody subcutaneously in 28-day cycles, wherein on a) Day 1, 8, 15 and 22 the first cycle, a priming dose of 160 μg is administered at day 1, an intermediate dose of 800 μg at day 8, and a dose of 48 mg at days 15, 22; for the first cycle; on b) Day 1, 8, 15 and 22 of cycles 2-3, a dose of 48 mg is administered;

c) Day 1, 15 of cycles 4-9, a dose of 48 mg is administered; and on d) Day 1, of further subsequent cycles, a dose of 48 mg is administered.

In still another embodiment, an advantageous dosing regimen that may be contemplated in the methods and uses of the invention may include administering the bispecific antibody subcutaneously in 28-day cycles, wherein on a) Day 1, 8, 15 and 22 the first cycle, a priming dose is administered at day 1, an intermediate dose at day 8, and a dose of 60 mg at days 15, 22; for the first cycle; on b) Day 1, 8, 15 and 22 of cycles 2-3, a dose of 60 mg is administered; on c) Day 1, 15 of cycles 4-9, a dose of 60 mg is administered; and on d) Day 1, of further subsequent cycles, a dose of 60 mg is administered.

In yet another further embodiment, an advantageous dosing regimen that may be contemplated in the methods and uses of the invention comprises administering the bispecific antibody subcutaneously in 28-day cycles, wherein on a) Day 1, 8, 15 and 22 the first cycle, a priming dose of 160 μg is administered at day 1, an intermediate dose of 800 μg at day 8, and a dose of 60 mg at days 15, 22; for the first cycle; on b) Day 1, 8, 15 and 22 of cycles 2-3, a dose of 60 mg is administered;

c) Day 1, 15 of cycles 4-9, a dose of 60 mg is administered;

d) Day 1, of further subsequent cycles, a dose of 60 mg is administered.

In one embodiment, alternatively, on days 1 and 8 of the first cycle, a priming dose of 80 μg and an intermediate dose of 800 μg is selected. In one embodiment, alternatively, on days 1 and 8 of the first cycle, a priming dose of 80 μg and an intermediate dose of 1200 μg is selected. In one embodiment, alternatively, on days 1 and 8 of the first cycle, a priming dose of 80 μg and an intermediate dose of 1600 μg is selected. In another embodiment, on days 1 and 8 of the first cycle, a priming dose of 160 μg and an intermediate dose of 1200 μg is selected. In another embodiment, on days 1 and 8 of the first cycle, a priming dose of 160 μg and an intermediate dose of 1600 μg is selected.

As said, such uses and methods are advantageous for the treatment of B-NHL, more preferably in the treatment of FL, DLBCL and/or HGBCL. Said treatment in accordance with the current invention, is maintained continuously, using treatment regimens as outlined above. When progressive disease develops, unacceptable toxicity occurs, or by death of the patient, treatment may be terminated.

Cytokine release syndrome (CRS) can occur when means and methods are used in human subjects that utilize immune cell- and bi-specific antibody-based approaches that function by activation of immune effector cell, such as by engaging CD3 (Lee et al., Biol Blood Marrow Transplant. 2019 April; 25(4):625-638, which is incorporated herein by reference). Hence, CRS mitigation is preferred in the methods and uses in accordance with the invention. As part of CRS mitigation, the selection of a priming dose and/or intermediate dose is highly preferred prior to administering the at least 24 mg dose, i.e. a full dose or flat dose, in accordance with the invention. CRS can be classified in accordance with standard practice (e.g. as outlined in Lee et al., Biol Blood Marrow Transplant. 2019 April; 25(4):625-638, which is incorporated herein by reference). CRS may include excessive release of cytokines, for example of proinflammatory cytokines, e.g. IL-6, TNF-alpha or IL-8, that may result in adverse effects like fever, nausea, vomiting and chills. Thus, despite the unique anti-tumor activity of bispecific antibodies such as epcoritamab, their immunological mode of action may trigger unwanted "side" effects, i.e. in the induction of unwanted inflammatory reactions. Hence, patients may be further subjected to a concomitant treatment, prophylaxis and/or premedication with e.g. analgesics, antipyretics, and/or anti-inflammatory drugs to mitigate possible CRS symptoms.

In one embodiment, said human subjects in methods and uses in accordance with the invention are treated with prophylaxis for cytokine release syndrome. Preferably, such a prophylaxis includes the administration of a corticosteroid. Said prophylaxis in one embodiment is administered at the same day as the bispecific antibody. Said prophylaxis can be administered on the subsequent day as well, more preferably at subsequent days 2 and 3. Optionally, said prophylaxis may be further administered at day 4, It is understood that days 2, 3 and 4 when relating to further medication, such as prophylaxis, is relative to the administration of the bispecific antibody which is administered at day 1. Hence, when e.g. in a cycle on day 15 the antibody is administered, and prophylaxis is administered, said prophylaxis corresponding to days 2, 3 and 4 are days 16, 17, and 18 of the cycle. In a further embodiment, said prophylaxis is administered at the day when the bispecific antibody is administered and at subsequent days 2-3, and day 4 is optional. When said prophylaxis is administered at the same day as the bispecific antibody, said prophylaxis is preferably administered 30-120 minutes prior to said administration of the bispecific antibody. A corticosteroid that may be preferred is prednisolone, e.g. at an intravenous dose of 100 mg, or an equivalent thereof, including an oral dose.

Furthermore, in one embodiment, said human subjects in methods and uses in accordance with the invention are treated with premedication to reduce reactions to injections. In one embodiment, said premedication includes the administration of antihistamines. In another embodiment, said premedication includes the administration of antipyretics. In a further embodiment, said premedication includes systemic antihistamines and antipyretics. An antihistamine that may be selected is diphenhydramine, e.g. at an intravenous or oral dose 50 mg, or an equivalent thereof. An antipyretic that may be selected is acetaminophen, e.g. at an oral dose of 650-1000 mg, or equivalent thereof. More preferably, said premedication is administered at the same day as the bispecific antibody, most preferably prior to the injection with the bispecific antibody, such as 30-120 minutes prior to said administration of the bispecific antibody.

It is understood that said premedication and/or prophylaxis are to be administered at least in the initial phase of the treatment. More preferably, during the first four administrations of the bispecific antibody. For example, said prophylaxis can be administered as described hereinbefore, during the first 28 day cycle of the bispecific antibody administration. Said premedication is preferably administered as well during said first cycle.

Usually, risk of reactions during the initial treatment subside after a few administrations, e.g. after the first four administrations (first cycle). Hence, and when the human subject does not experience CRS, prophylaxis medication for CRS may be stopped. However, preferably, when the human subject would experience a CRS greater than grade 1, CRS prophylaxis may continue. Likewise, premedication may also optionally continue.

In a further embodiment, in methods and uses in accordance with the invention as described herein, said prophylaxis is administered during the second 28-day cycle when the human subject experiences CRS greater than grade 1 after the fourth administration of the bispecific antibody in cycle 1. Furthermore, said prophylaxis can be continued during a subsequent cycle, when in the last administration of the bispecific antibody of the previous cycle, the human subject experiences CRS greater than grade 1. Any premedication may be optionally administered during the second cycle. Further premedication may be optionally administered during subsequent cycles as well.

In one embodiment, premedication and prophylaxis for CRS is administered, including an antihistamine, said antihistamine may be diphenhydramine, e.g. at an intravenous or oral dose 50 mg, or an equivalent thereof, and an antipyretic, said antipyretic may be acetaminophen, e.g. at an oral dose of 650-1000 mg, or an equivalent thereof, and the administration of a corticosteroid, which corticosteroid may be prednisolone, e.g. at an intravenous dose of 100 mg, or an equivalent thereof, said premedication and prophylaxis is administered 30-120 minutes prior to administration of the bispecific antibody. On subsequent days 2, 3, and optionally day 4, further prophylaxis is administered comprising the systemic administration of a corticosteroid, which corticosteroid may be prednisolone, e.g. at an intravenous dose of 100 mg, or an equivalent thereof. Preferably, on subsequent days 2, 3, and 4, said further prophylaxis is administered comprising the systemic administration of a corticosteroid, which corticosteroid may be prednisolone, e.g. at an intravenous dose of 100 mg, or an equivalent thereof. Such premedication and prophylaxis schedule preferably is administered during the first four administrations of the bispecific antibody in accordance with the invention. For example, during the first 28-day cycle of bispecific antibody administration as described herein. Furthermore, subsequent cycles, in case of e.g. CRS greater than grade 1 occurring during the last administration of the prior cycle, can include the same administration schedule, wherein the premedication as part of the administration schedule is optional.

At the provided advantageous doses and/or treatment regimens as provided herein CRS can be well managed while at the same time allowing for effectively controlling and/or treating B-NHL. As shown in the example section, in the methods and uses as described herein, in said human subjects, manageable cytokine release syndrome CRS may occur. Human subjects receiving treatments in accordance with the invention may have CRS of grade 1 as defined in accordance with standard practice. Human subjects receiving treatments in accordance with the invention may have manageable CRS of grade 2 as defined in accordance with standard practice. Hence, human subjects receiving treatments in accordance with the invention may have manageable CRS of grade 1 or grade 2 during as defined in accordance with standard practice. In accordance with standard classification for CRS, a grade 1 CRS includes a fever to at least 38° C., no hypotension, no hypoxia, and a grade 2 CRS includes a fever to at least 38° C. plus hypotension, not requiring vasopressors and/or hypoxia requiring oxygen by low flow nasal cannula or blow by. Such manageable CRS can occur during cycle 1. Human subjects receiving treatments in accordance with the invention may also have CRS greater than grade 2 during said treatments as defined in accordance with standard practice. Hence, human subjects receiving treatments in accordance with the invention may also have CRS of grade 3 during said treatments as defined in accordance with standard practice. Such manageable CRS may further occur during cycle 1 and subsequent cycles.

Said human subjects may experience in methods and uses in accordance with the invention, pyrexia. Fatigue and injection site reactions may also occur. Human subjects may experience neurotoxicity, partial seizures, agraphia related to CRS, or confusional state related to CRS. Moreover, said human subjects may be observed not to experience tumor lysis syndrome.

Because of the safety profile of epcoritamab, it may not be required to hospitalize patients to administer epcoritamab. In a further embodiment, the methods and uses in accordance with the invention for the treatment of B-NHL involves the administration of epcoritamab in an outpatient setting. Administration in an outpatient setting does not involve hospitalization. In another embodiment, patients are hospitalized for administration only of the first full dose. Said first full dose is administered for example on day 15 of cycle 1, wherein days 1 and 8, respectively involve step up doses, as described herein. A preferred dose, in methods and uses as described herein, for outpatient use of epcoritamab includes the full dose, which may be up to 60 mg. More preferably, a dose for administration in outpatient use is 48 mg. In another embodiment, the methods and uses in accordance with the invention for the treatment of B-NHL involves the administration of epcoritamab exclusively in an outpatient setting.

As described herein, in the methods and uses in accordance with the invention, the bispecific antibody in accordance with the invention aimed at targeting CD3 and CD20 comprises:

(i) a first binding arm comprising a first antigen-binding region binding to human CD3ε (epsilon), comprising a variable heavy chain region and a variable light chain region wherein the variable heavy chain region comprises the CDR1, CDR2 and CDR3 sequences of SEQ ID NO:6; and wherein the variable light chain region comprises the CDR1, CDR2 and CDR3 sequences of SEQ ID NO: 7; and (ii) a second binding arm comprising a second antigen-binding region binding to human CD20, comprising a variable heavy chain region and a variable light chain region wherein the variable heavy chain region comprises the CDR1, CDR2 and CDR3 sequences of SEQ ID No: 13; and wherein the variable light chain region comprises the CDR1, CDR2 and CDR3 sequences of SEQ ID No: 14.

CDR1, CDR2 and CDR3 regions can be identified from variable heavy and light chain regions using methods known in the art. The CDR regions from said variable heavy and light chain regions can be annotated according to IMGT (see Lefranc M P. et al., Nucleic Acids Research, 27, 209-212, 1999] and Brochet X. Nucl. Acids Res. 36, W503-508 (2008)). Hence, also disclosed in the methods and uses in accordance with the invention, the bispecific antibody in accordance with the invention aimed at targeting CD3 and CD20 comprises:

(i) a first binding arm comprising a first antigen-binding region binding to human CD3ε (epsilon), wherein said first antigen-binding region comprises a heavy chain variable (VH) region CDR1, CDR2, and CDR3 having the sequences as set forth in SEQ ID NOs. 1, 2, and 3, respectively, and a light chain variable (VL) region CDR1, CDR2, and CDR3 having the sequences as set forth in SEQ ID NO. 4, the sequence GTN, and the sequence as set forth in SEQ ID NO. 5, respectively, and (ii) a second binding arm comprising a second antigen-binding region binding to human CD20, wherein said second antigen-binding region comprises a heavy chain variable (VH) region CDR1, CDR2, and CDR3 having the sequences as set forth in SEQ ID NOs. 8, 9, and 10, respectively, and a light chain variable (VL) region CDR1, CDR2, and CDR3 having the sequences as set forth in SEQ ID NO. 11, the sequence DAS, and the sequence as set forth in SEQ ID NO. 12, respectively.

In yet a further embodiment, in the methods and uses in accordance with the invention, the bispecific antibody comprises (i) a first binding arm comprising a first antigen-binding region binding to human CD3ε (epsilon), comprising a variable heavy chain region and a variable light chain region wherein the variable heavy chain region comprises SEQ ID NO:6; and wherein the variable light chain region comprises SEQ ID NO:7; and (ii) a second binding arm comprising a second antigen-binding region binding to human CD20, comprising a variable heavy chain region and a variable light chain region wherein the variable heavy chain region comprises SEQ ID No: 13; and wherein the variable light chain region comprises SEQ ID No:14.

As said, the bispecific antibody in accordance with the invention is most preferably a full-length antibody and may have an inert Fc region. More preferably, the first binding arm for CD3 is derived from a humanized antibody, preferably from a full-length IgG1,λ (lambda) antibody such as H1L1 described in WO2015001085, which is incorporated herein by reference) and/or the second binding arm for CD20 is derived from a human antibody, preferably from a full-length IgG1,κ (kappa) antibody such as clone 7D8 as described in WO2004035607, which is incorporated herein by reference. The bispecific antibody may be produced from two half molecule antibodies. Each of the two half molecule antibodies comprising e.g. the respective first and second binding arms as listed herein in SEQ ID NOs. 6 and 7, and SEQ ID NOs. 13 and 14. The half-antibodies may be produced in CHO cells and the bispecific antibodies generated by e.g. Fab-arm exchange. In one embodiment, said bispecific antibody in accordance with the invention is a functional variant of Duobody CD3×CD20.

Various constant regions or variants thereof may be contemplated in accordance with the invention. Nevertheless, most preferably, the bispecific antibody in accordance with the invention comprises a human IgG1 constant region, such as a human IgG1 constant region as defined in SEQ ID NO. 15, or any other suitable IgG1 allotype. As said, the first binding arm of the bispecific antibody preferably is derived from a humanized antibody, preferably from a full-length IgG1,λ (lambda) antibody, hence comprising a λ light chain constant region. More preferably, said first binding arm as defined herein comprises a λ light chain constant region as defined in SEQ ID NO. 22. Furthermore, said second binding arm of the bispecific antibody is derived from a human antibody, preferably from a full-length IgG1,κ (kappa) antibody, hence comprising a κ light chain constant region. More preferably, said second binding arm comprises a κ light chain constant region as defined in SEQ ID NO. 23.

It is understood that the constant region, as it is part of a bispecific antibody, said constant region may comprise modifications to allow for efficient formation/production of bispecific antibodies and/or provide for an inert Fc region. Such modifications are I known in the art. Different formats and uses of bispecific antibodies are known in the art (reviewed by Kontermann; Drug Discov Today, 2015 July; 20(7):838-47 and; MAbs, 2012 March-April; 4(2):182-97) and not necessarily be limited to any particular bispecific format or method of producing it. For example, bispecific antibodies may include but are not limited to (i) bispecific antibodies with complementary CH3 domains to force heterodimerization), the so-called Knobs-into-Holes molecules (Genentech, WO9850431), CrossMAbs (Roche, WO2011117329) or electrostatically-matched molecules (Amgen, EP1870459 and WO2009089004; Chugai, US201000155133; Oncomed, WO2010129304).

Preferably, the bispecific antibody of the invention comprises an Fc-region comprising a first heavy chain with a first Fc sequence comprising a first CH3 region, and a second heavy chain with a second Fc sequence comprising a second CH3 region, wherein the sequences of the first and second CH3 regions are different and are such that the heterodimeric interaction between said first and second CH3 regions is stronger than each of the homodimeric interactions of said first and second CH3 regions. More details on these interactions and how they can be achieved are provided in e.g. WO2011131746 and WO2013060867 (Genmab), which are hereby incorporated by reference. In a preferred embodiment, the bispecific antibody in the methods and uses in accordance with the invention comprises in said first heavy chain (i) the amino acid L in the position corresponding to F405 in a human IgG1 heavy chain of SEQ ID NO:15, and comprises in said second heavy chain the amino acid R in the position corresponding to K409 in a human IgG1 heavy chain of SEQ ID NO:15 is R, or vice versa.

Antibodies according to the present invention may comprise modifications in the Fc region to render the Fc region of the antibody inert, or non-activating. Hence, the bispecific antibodies disclosed herein, one or both heavy chains may be modified so that the antibody induces Fc-mediated effector function to a lesser extent relative to the bispecific antibody which does not have such modification. The Fc-mediated effector function may be measured by determining Fc-mediated CD69 expression on T cells (i.e. CD69 expression as a result of CD3 antibody-mediated, Fcγ receptor-dependent CD3 crosslinking), by binding to Fcγ receptors, by binding to C1q, or by induction of Fc-mediated crosslinking of FcγRs. In particular, the heavy chain constant sequences may be modified so that the Fc-mediated CD69 expression is reduced by at least 50%, at least 60%, at least 70%, at least 80%, at least 90%, at least 99% or 100% when compared to a wild-type (unmodified) antibody, wherein said Fc-mediated CD69 expression is determined in a PBMC-based functional assay, e.g. as described in Example 3 of WO2015001085. Modifications of the heavy and light chain constant sequences may also result in reduced binding of C1q to said antibody. As compared to an unmodified antibody the reduction may be by at least 70%, at least 80%, at least 90%, at least 95%, at least 97%, or 100% and the C1q binding may be determined by ELISA. Further, the Fc region which may be modified so that said antibody mediates reduced Fc-mediated T-cell proliferation compared to an unmodified antibody by at least 50%, at least 60%, at least 70%, at least 80%, at least 90%, at least 99% or 100%, wherein said T-cell proliferation is measured in a PBMC-based functional assay. Examples of amino acid positions that may be modified, e.g. in an IgG1 isotype antibody, include positions L234 and L235. Hence, the antibody according to the invention may comprises a first and a second heavy chain, and wherein in both the first and the second heavy chain, the amino acid residues at the positions corresponding to positions L234 and L235 in a human IgG1 heavy chain according to Eu numbering are F and E, respectively. In addition, a D265A amino acid substitution can decrease binding to all Fcγ receptors and prevent ADCC (Shields et al., 2001, J. Biol. Chem. (276):6591-604). Therefore, the antibody according to the invention may comprise a first and a second heavy chain, wherein in both the first and the second heavy chain, the amino acid residue at the position corresponding to position D265 in a human IgG1 heavy chain according to Eu numbering is A.

Most preferred, in the methods and uses in accordance with the invention, bispecific antibodies are provided wherein said first and second heavy chains, the amino acids in the positions corresponding to positions L234, L235, and D265 in a human IgG1 heavy chain, are F, E, and A, respectively. An antibody having these amino acids at these positions, is an example of an antibody having an inert Fc region, or a non-activating Fc region.

In the present application antibodies, which have the combination of three amino acid substitutions L234F, L235E and D265A and in addition the K409R or the F405L mutation disclosed herein above may be termed with the suffix "FEAR" or "FEAL", respectively.

As said, an amino acid sequence of a wild type IgG1 heavy chain constant region is identified herein as SEQ ID NO: 15. Consistent with the embodiments disclosed above, the antibody of the invention may comprise an IgG1 heavy chain constant region carrying the F405L substitution and may have the amino acid sequence set forth in SEQ ID NO: 17 and/or an IgG1 heavy chain constant region carrying the K409R substitution and may have the amino acid sequence set forth in SEQ ID NO: 18, and have further substitutions that render the Fc region inert or non-activating. Hence, most and highly preferred, a combination of IgG1 heavy chain constant regions that are comprised in a bispecific antibody in accordance with the invention are an amino acid sequence of an IgG1 heavy chain constant region carrying the L234F, L235E, D265A and F405L substitutions such as identified herein as SEQ ID NO: 19 and an amino acid sequence of an IgG1 heavy chain constant region carrying the L234F, L235E, D265A and K409R substitutions such as identified herein as SEQ ID NO: 20.

In one further highly preferred embodiment, the bispecific antibody in the methods and uses as described herein comprises a first binding arm having a heavy chain and a light chain as defined in SEQ ID NOs. 24 and 25, respectively, and a second binding arm having a heavy chain and a light chain as defined in SEQ ID NOs. 26 and 27. Such an antibody may be referred to herein as Duobody CD3×CD20. Also, variants of such antibodies can be contemplated for the methods and uses as described herein. In still a further embodiment, the bispecific antibody in accordance with the invention is epcoritamab (CAS 2134641-34-0), or a biosimilar thereof.

Further Embodiments

1. A bispecific antibody, comprising
(i) a first binding arm comprising a first antigen-binding region binding to human CD3ε (epsilon), comprising a variable heavy chain region and a variable light chain region wherein the variable heavy chain region comprises the CDR1, CDR2 and CDR3 sequences of SEQ ID NO:6; and wherein the variable light chain region comprises the CDR1, CDR2 and CDR3 sequences of SEQ ID NO: 7; and
(ii) a second binding arm comprising a second antigen-binding region binding to human CD20, comprising a variable heavy chain region and a variable light chain region wherein the variable heavy chain region comprises the CDR1, CDR2 and CDR3 sequences of SEQ ID No: 13; and wherein the variable light chain region comprises the CDR1, CDR2 and CDR3 sequences of SEQ ID No: 14;
for use in the treatment of a B-cell Non-Hodgkin Lymphoma (B-NHL) in a human subject, wherein said treatment comprising administering said bispecific antibody subcutaneously to the human subject in need thereof at a dose of at least 24 mg.

2. A bispecific antibody, which is a full-length antibody, comprising
(i) a first binding arm comprising a first antigen-binding region binding to human CD3ε (epsilon), comprising a variable heavy chain region and a variable light chain region wherein the variable heavy chain region comprises the CDR1, CDR2 and CDR3 sequences of SEQ ID NO:6; and wherein the variable light chain region comprises the CDR1, CDR2 and CDR3 sequences of SEQ ID NO: 7; and
(ii) a second binding arm comprising a second antigen-binding region binding to human CD20, comprising a variable heavy chain region and a variable light chain region wherein the variable heavy chain region comprises the CDR1, CDR2 and CDR3 sequences of SEQ ID No: 13; and wherein the variable light chain region comprises the CDR1, CDR2 and CDR3 sequences of SEQ ID No: 14;
for use in the treatment of a B-cell Non-Hodgkin Lymphoma (B-NHL) in a human subject, wherein said treatment comprising administering said bispecific antibody subcutaneously to the human subject in need thereof at a dose of at least 24 mg.

3. The bispecific antibody for use in accordance with embodiment 1 or 2, wherein said B-NHL is selected from the group consisting of diffuse large B-cell lymphoma (DLBCL), high-grade B-cell lymphoma (HGBCL), primary mediastinal large B-cell lymphoma (PMBCL), mantle cell lymphoma, follicular lymphoma (FL), marginal-zone lymphoma and small lymphocytic lymphoma.

4. The bispecific antibody for use in accordance with embodiment 1 or 2, wherein said B-NHL is FL, HGBCL, or DLBCL.

5. The bispecific antibody for use in accordance with any one of embodiments 1-4, wherein said subject has received prior to the treatment with the bispecific antibody a treatment with a CD20 monospecific antibody, such as rituximab.

6. The bispecific antibody for use in accordance with embodiment 5, wherein during said treatment with the CD20 monospecific antibody, the cancer relapsed.

7. The bispecific antibody for use in accordance with embodiment 5, wherein during said treatment with the CD20 monospecific antibody, the cancer was refractory to said treatment.

8. The bispecific antibody for use in accordance with any one of embodiments 5-7, wherein said CD20 monospecific antibody was used in a combination treatment.

9. The bispecific antibody for use in accordance with any one of embodiments 1-8, wherein the patient received further prior lines of treatment for said B-cell NHL.

10. The bispecific antibody for use in accordance with any one of embodiments 1-9, wherein said bispecific antibody is administered at a dose of at least 40 mg.

11. The bispecific antibody for use in accordance with any one of embodiments 1-9, wherein said bispecific antibody is administered at a dose in the range of between 40 mg to 100 mg.

12. The bispecific antibody for use in accordance with any one of embodiments 1-9, wherein said bispecific antibody is administered at a dose of at least 48 mg.

13. The bispecific antibody for use in accordance with any one of embodiments 1-9, wherein said bispecific antibody is administered at a dose of at least 60 mg.

14. The bispecific antibody for use in accordance with any one of embodiments 1-9, wherein said bispecific antibody is administered at a dose of 48 mg.

15. The bispecific antibody for use in accordance with any one of embodiments 1-9, wherein said bispecific antibody is administered at a dose of 60 mg.

16. The bispecific antibody for use in accordance with any one of embodiments 1-15, wherein said dose is administered weekly.

17. The bispecific antibody for use in accordance with embodiment 16, wherein said weekly administration is performed at least 4 times.

18. The bispecific antibody for use in accordance with embodiment 16 or 17, wherein after said weekly administration, said antibody is administered once every two weeks.

19. The bispecific antibody for use in accordance with embodiment 18, wherein said biweekly administration is performed (at least) 6 times.

20. The bispecific antibody for use in accordance with embodiment 18 or 19, wherein after said administration once every two weeks, said antibody is administered once every four weeks.

21. The bispecific antibody for use in accordance with any one of embodiments 16-20, wherein prior to administering said weekly dose, a priming dose of said bispecific antibody is administered.

22. The bispecific antibody for use in accordance with embodiment 21, wherein said priming dose is administered one week prior to administering the first dose of said weekly dose.

23. The bispecific antibody for use in accordance with embodiment 21 or 22, wherein said priming dose is in the range of 50-300 µg.

24. The bispecific antibody for use in accordance with any one of embodiments 21-23, wherein said priming dose is 160 µg.

25. The bispecific antibody for use in accordance with embodiment 21-24 wherein after administering said priming dose and prior to administering said weekly dose, an intermediate dose of said bispecific antibody is administered.

26. The bispecific antibody for use in accordance with embodiment 25, wherein said priming dose is administered two weeks, and said intermediate dose is administered one week, before administering the first dose of said weekly dose.

27. The bispecific antibody for use in accordance with any one of embodiments 25 or 26, wherein said intermediate dose is in the range of 600-1200 µg.

28. The bispecific antibody for use in accordance with any one of embodiments 25-27, wherein said intermediate dose is 800 µg.

29. The bispecific antibody for use in accordance with any one of embodiments 25-28, said use comprises administering the bispecific antibody subcutaneously in 28-day cycles, wherein on:
   a) Day 1, 8, 15 and 22 of the first cycle, a priming dose is administered at day 1, an intermediate dose at day 8, and a dose of 48 mg at days 15, 22; for the first cycle; on
   b) Day 1, 8, 15 and 22 of cycles 2-3, a dose of 48 mg is administered; on
   c) Day 1, 15 of cycles 4-9, a dose of 48 mg is administered; and on
   d) Day 1, of further subsequent cycles, a dose of 48 mg is administered.

30. The bispecific antibody for use in accordance with any one of embodiments 25-28, wherein said use comprises administering the bispecific antibody subcutaneously in 28-day cycles, wherein on:
   a) Day 1, 8, 15 and 22 the first cycle, a priming dose of 160 µg is administered at day 1, an intermediate dose of 800 µg at day 8, and a dose of 48 mg at days 15, 22; for the first cycle; on
   b) Day 1, 8, 15 and 22 of cycles 2-3, a dose of 48 mg is administered;
   c) Day 1, 15 of cycles 4-9, a dose of 48 mg is administered; and on
   d) Day 1, of further subsequent cycles, a dose of 48 mg is administered.

31. The bispecific antibody for use in accordance with any one of embodiments 25-28, wherein said use comprises administering the bispecific antibody subcutaneously in 28-day cycles, wherein on:
   a) Day 1, 8, 15 and 22 the first cycle, a priming dose is administered at day 1, an intermediate dose at day 8, and a dose of 60 mg at days 15, 22; for the first cycle; on
   b) Day 1, 8, 15 and 22 of cycles 2-3, a dose of 60 mg is administered; on
   c) Day 1, 15 of cycles 4-9, a dose of 60 mg is administered; and on
   d) Day 1, of further subsequent cycles, a dose of 60 mg is administered 32. The bispecific antibody for use in accordance with any one of embodiments 25-28, wherein the method of treatment comprises administering the bispecific antibody subcutaneously in 28-day cycles, wherein on:
   a) Day 1, 8, 15 and 22 the first cycle, a priming dose of 160 µg is administered at day 1, an intermediate dose of 800 µg at day 8, and a dose of 60 mg at days 15, 22; for the first cycle; on
   b) Day 1, 8, 15 and 22 of cycles 2-3, a dose of 60 mg is administered;
   c) Day 1, 15 of cycles 4-9, a dose of 60 mg is administered;
   d) Day 1, of further subsequent cycles, a dose of 60 mg is administered.

33. The bispecific antibody for use in accordance with any one of embodiments 29-32, wherein said B-NHL is FL, DLBCL and/or HGBCL.

34. The bispecific antibody for use in accordance with any one of embodiments 1-33, wherein said subject has manageable cytokine release syndrome (CRS) of grade 1 or grade 2 during said use.

35. The bispecific antibody for use in accordance with any one of embodiments 1-34, wherein said subject does not experience tumor lysis syndrome.

36. The bispecific antibody for use in accordance with any one of embodiments 1-35, wherein said subjects are treated with prophylaxis for cytokine release syndrome (CRS).

37. The bispecific antibody for use in accordance with embodiment 36, wherein said prophylaxis includes the administration of a corticosteroid.

38. The bispecific antibody for use in accordance with any one embodiment 36-37 wherein said prophylaxis is administered at the same day as the bispecific antibody.

39. The bispecific antibody for use in accordance with any one of embodiment 38, wherein said prophylaxis is administered at subsequent days 2-3, and optionally day 4, or at subsequent days 2-4.

40. The bispecific antibody for use in accordance with any one of embodiments 38-39 wherein when said prophylaxis is administered at the same day as the bispecific antibody, said prophylaxis is administered 30-120 minutes prior to said administration of the bispecific antibody.

41. The bispecific antibody for use in accordance with any one of embodiments 37-40, wherein said corticosteroid is prednisolone, e.g. at an intravenous dose of 100 mg, or equivalent thereof, including oral dose.

42. The bispecific antibody for use in accordance with any one of embodiments 1-41, wherein said human subjects are treated with premedication to reduce reactions to injections.

43. The bispecific antibody for use in accordance with embodiment 42, wherein said premedication includes the administration of antihistamines.

44. The bispecific antibody for use in accordance with any one of embodiments 42-43, wherein said premedication includes the administration of antipyretics.

45. The bispecific antibody for use in accordance with any one of embodiments 42-44, wherein said antihistamine is diphenhydramine, e.g. at an intravenous or oral dose 50 mg, or equivalent thereof.

46. The bispecific antibody for use in accordance with any one of embodiments 43-45, wherein said antipyretic is acetaminophen, e.g. at an oral dose of 650-1000 mg, or equivalent thereof.

47. The bispecific antibody for use in accordance with any one of embodiment 42-45, wherein said premedication is administered at the same day as the bispecific antibody.

48. The bispecific antibody for use in accordance with embodiment 47, wherein said premedication administered 30-120 minutes prior to said administration of the bispecific antibody.

49. The bispecific antibody for use in accordance with any one of embodiments 29-48, wherein said prophylaxis as defined in embodiments 35-41 is administered during the first cycle.

50. The bispecific antibody for use in accordance with any one of embodiments 29-49, wherein said premedication as defined in embodiments 42-48, is administered during the first cycle.

51. The bispecific antibody for use in accordance with embodiment 49 and 50, wherein said prophylaxis is administered during the second cycle when the human subject experiences CRS greater than grade 1 after the fourth administration of the bispecific antibody in cycle 1.

52. The bispecific antibody for use in accordance with embodiment 51, wherein said prophylaxis is continued during a subsequent cycle, when in the last administration of the bispecific antibody of the previous cycle, the human subject experiences CRS greater than grade 1.

53. The bispecific antibody for use in accordance with embodiment 51 or 52, wherein said premedication is optionally administered during the second cycle.

54. The bispecific antibody for use in accordance with embodiment 53, wherein said premedication is optionally administered during subsequent cycles.

55. The bispecific antibody for use in accordance with any one of the preceding embodiments, wherein the bispecific antibody comprises:
(i) a first binding arm comprising a first antigen-binding region binding to human CD3ε (epsilon), wherein said first antigen-binding region comprises a heavy chain variable (VH) region CDR1, CDR2, and CDR3 having the sequences as set forth in SEQ ID NOs. 1, 2, and 3, respectively, and a light chain variable (VL) region CDR1, CDR2, and CDR3 having the sequences as set forth in SEQ ID NO. 4, the sequence GTN, and the sequence as set forth in SEQ ID NO. 5, respectively, and
(ii) a second binding arm comprising a second antigen-binding region binding to human CD20, wherein said second antigen-binding region comprises a heavy chain variable (VH) region CDR1, CDR2, and CDR3 having the sequences as set forth in SEQ ID NOs. 8, 9, and 10, respectively, and a light chain variable (VL) region CDR1, CDR2, and CDR3 having the sequences as set forth in SEQ ID NO. 11, the sequence DAS, and the sequence as set forth in SEQ ID NO. 12, respectively.

56. The bispecific antibody for use in accordance with any one of the preceding embodiments, wherein the bispecific antibody comprises:
(i) a first binding arm comprising a first antigen-binding region binding to human CD3ε (epsilon), comprising a variable heavy chain region as defined by SEQ ID NO:6; and a variable light chain region as defined by SEQ ID NO:7; and
(ii) a second binding arm comprising a second antigen-binding region binding to human CD20, comprising a variable heavy chain region as defined by SEQ ID No: 13; and a variable light chain region as defined by SEQ ID No: 14.

57. The bispecific antibody for use in accordance with any one of the preceding embodiments, wherein the first binding arm of the bispecific antibody is derived from a humanized antibody, preferably from a full-length IgG1,λ (lambda) antibody.

58. The bispecific antibody for use in accordance with embodiment 57, wherein said bispecific antibody comprises a λ light chain constant region as defined in SEQ ID NO. 22.

59. The bispecific antibody for use in accordance with any one of the preceding embodiments, wherein the second binding arm of the bispecific antibody is derived from a human antibody, preferably from a full-length IgG1,κ (kappa) antibody.

60. The bispecific antibody for use in accordance with embodiment 59, wherein said bispecific antibody comprises a κ light chain constant region as defined in SEQ ID NO. 23.

61. The bispecific antibody for use in accordance with any one of the preceding embodiments, wherein the bispecific antibody is a full-length antibody with a human IgG1 constant region.

62. The bispecific antibody for use in accordance with any one of the preceding embodiments, in which the bispecific antibody comprises an inert Fc region.

63. The bispecific antibody for use in accordance with embodiment 62, wherein the bispecific antibody comprises in the first and second heavy chain at the positions corresponding to positions L234, L235, and D265 in the human IgG1 heavy chain of SEQ ID NO:15 of both the first heavy chain and the second heavy chain, the amino acids F, E, and A, respectively.

64. The bispecific antibody for use in accordance with any one of the preceding embodiments, wherein the bispecific antibody comprises in said first heavy chain the amino acid L in the position corresponding to F405 in a human IgG1 heavy chain of SEQ ID NO:15, and wherein said second heavy chain comprises the amino acid R in the position corresponding to K409 in a human IgG1 heavy chain of SEQ ID NO:15 is R, or vice versa.

65. The method in accordance with any one of the preceding embodiments, wherein the bispecific antibody comprises in the first and second heavy chain at the positions corresponding to positions L234, L235, and D265 in the human IgG1 heavy chain of SEQ ID NO:15 of both the first heavy chain and the second heavy chain, the amino acids F, E, and A, respectively, and wherein in said first heavy chain the amino acid L in the position corresponding to F405 in a human IgG1 heavy chain of SEQ ID NO:15, and wherein said second heavy chain comprises the amino acid R in the position corresponding to K409 in a human IgG1 heavy chain of SEQ ID NO:15 is R, or vice versa.

66. The bispecific antibody for use in accordance with embodiment 65, wherein the bispecific antibody comprises constant regions as defined in SEQ ID NO. 19 and 20.

67. The bispecific antibody for use in accordance with any one of the preceding embodiments, wherein the bispecific antibody comprises a heavy chain and a light chain as defined in SEQ ID NOs. 24 and 25, respectively, and a heavy chain and a light chain as defined in SEQ ID NOs. 26 and 27.

68. The bispecific antibody for use in accordance with any one of the preceding embodiments, the bispecific antibody consists of a heavy chain and a light chain as defined in SEQ ID NOs. 24 and 25, respectively, and a heavy chain and a light chain as defined in SEQ ID NOs. 26 and 27.

69. The bispecific antibody for use in accordance with any one of the preceding embodiments, wherein the bispecific antibody is epcoritamab, or a biosimilar thereof.

Sequences

TABLE 1

Bold and underlined are FE; A; L and R, corresponding with positions 234 and 235; 265; 405 and 409, respectively, said positions being in accordance with EU-numbering. In variable regions, said CDR regions that were annotated in accordance with IMGT definitions are underlined.

| SEQ ID NO: | Clone name | Sequence |
|---|---|---|
| SEQ ID NO: 1 | huCD3 VH CDR1 | GFTFNTYA |
| SEQ ID NO: 2 | huCD3 VH CDR2 | IRSKYNNYAT |
| SEQ ID NO: 3 | huCD3 VH CDR3 | VRHGNFGNSYVSWFAY |
| SEQ ID NO: 4 | huCD3 VL CDR1 | TGAVTTSNY |
| | huCD3 VL CDR2 | GTN |
| SEQ ID NO: 5 | huCD3 VL CDR3 | ALWYSNLWV |
| SEQ ID NO: 6 | huCD3 VH1 | EVKLVESGGGLVQPGGSLRLSCAASGFTFNTYAMNWVRQAPGKGLEWVAR IRSKYNNYATYYADSVKDRFTISRDDSKSSLYLQMNNLKTEDTAMYYCVR HGNFGNSYVSWFAYWGQGTLVTVSS |
| SEQ ID NO: 7 | huCD3 VL1 | QAVVTQEPSFSVSPGGTVTLTCRSSTGAVTTSNYANWVQQTPGQAFRGLI GGTNKRAPGVPARFSGSLIGDKAALTITGAQADDESIYFCALWYSNLWVF GGGTKLTVL |
| SEQ ID NO: 8 | VH CD20-7D8 CDR1 | GFTFHDYA |
| SEQ ID NO: 9 | VH CD20-7D8 CDR2 | ISWNSGTI |
| SEQ ID NO: 10 | VH CD20-7D8 CDR3 | AKDIQYGNYYYGMDV |
| SEQ ID NO: 11 | VL CD20-7D8 CDR1 | QSVSSY |
| | VL CD20-7D8 CDR2 | DAS |
| SEQ ID NO: 12 | VL CD20-7D8 CDR3 | QQRSNWPIT |
| SEQ ID NO: 13 | VH CD20-7D8 | EVQLVESGGGLVQPDRSLRLSCAASGFTFHDYAMHWVRQAPGKGLEWVST ISWNSGTIGYADSVKGRFTISRDNAKNSLYLQMNSLRAEDTALYYCAKDI QYGNYYYGMDVWGQGTTVTVSS |
| SEQ ID NO: 14 | VL CD20-7D8 | EIVLTQSPATLSLSPGERATLSCRASQSVSSYLAWYQQKPGQAPRLLIYD ASNRATGIPARFSGSGSGTDFTLTISSLEPEDFAVYYCQQRSNWPITFGQ GTRLEIK |

TABLE 1-continued

Bold and underlined are FE; A; L and R, corresponding with positions 234 and 235;
265; 405 and 409, respectively, said positions being in accordance with
EU-numbering. In variable regions, said CDR regions that were annotated
in accordance with IMGT definitions are underlined.

| SEQ ID NO: | Clone name | Sequence |
|---|---|---|
| SEQ ID NO: 15 | IgG1 heavy chain constant region-WT (amino acids positions 118-447 according to EU numbering). CH3 region italics | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAK*GQPREPQVYTLPPSREEMTKNQVSLTC LVKGFYPSDIAVEWESNGQPENNYKTTPPVLDSDGSFFLYSKLTVDKSRW QQGNVFSCSVMHEALHNHYTQKSLSLSPG* |
| SEQ ID NO: 16 | IgG1-LFLEDA heavy chain constant region (amino acids positions 118-447 according to EU numbering). | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEP KSCDKTHTCPPCPAPEFEGGPSVFLFPPKPKDTLMISRTPEVTCVVVAVS HEDPEVKFNWYVDGVE̲V̲H̲NAKTKPREEQYNSTYRVVSVLTVLHQDWL̲NGK EYKCKVSNKALPAPIEKTISKAKGQPREPQVYTLPPSREEMTKNQVSLTC LVKGFYPSDIAVEWESNGQPENNYKTTPPVLDSDGSFFLYSKLTVDKSRW QQGNVFSCSVMHEALHNHYTQKSLSLSPG |
| SEQ ID NO: 17 | IgG1 F405L (amino acids positions 118-447 according to EU numbering) | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTC LVKGFYPSDIAVEWESNGQPENNYKTTPPVLDSDGSFLLYSKLTVDKSRW QQGNVFSCSVMHEALHNHYTQKSLSLSPG |
| SEQ ID NO: 18 | IgG1-K409R (amino acids positions 118-447 according to EU numbering) | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTC LVKGFYPSDIAVEWESNGQPENNYKTTPPVLDSDGSFFLRLTVDKSRW QQGNVFSCSVMHEALHNHYTQKSLSLSPG |
| SEQ ID NO: 19 | IgG1-LFLEDA-F405L (FEAL) (amino acids positions 118-447 according to EU numbering) | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEP KSCDKTHTCPPCPAPEFEGGPSVFLFPPKPKDTLMISRTPEVTCVVVAVS HEDPEVKFNWYVDGVE̲V̲H̲NAKTKPREEQYNSTYRVVSVLTVLHQDWL̲NGK EYKCKVSNKALPAPIEKTISKAKGQPREPQVYTLPPSREEMTKNQVSLTC LVKGFYPSDIAVEWESNGQPENNYKTTPPVLDSDGSFLLYSKLTVDKSRW QQGNVFSCSVMHEALHNHYTQKSLSLSPG |
| SEQ ID NO: 20 | IgG1-LFLEDA-K409R (FEAR) (amino acids positions 118-447 according to EU numbering) | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEP KSCDKTHTCPPCPAPEFEGGPSVFLFPPKPKDTLMISRTPEVTCVVVAVS HEDPEVKFNWYVDGVE̲V̲H̲NAKTKPREEQYNSTYRVVSVLTVLHQDWL̲NGK EYKCKVSNKALPAPIEKTISKAKGQPREPQVYTLPPSREEMTKNQVSLTC LVKGFYPSDIAVEWESNGQPENNYKTTPPVLDSDGSFFLYSRLTVDKSRW QQGNVFSCSVMHEALHNHYTQKSLSLSPG |
| SEQ ID NO: 21 | IgG1 CH3 region | GQPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQKS LSLSPG |
| SEQ ID NO: 22 | Constant region human lambda LC | GQPKAAPSVTLFPPSSEELQANKATLVCLISDFYPGAVTVAWKADSSPVK AGVETTTPSKQSNNKYAASSYLSLTPEQWKSHRSYSCQVTHEGSTVEKTV APTECS |
| SEQ ID NO: 23 | Constant region human kappa LC | RTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTK SFNRGEC |
| SEQ ID NO: 24 | huCD3-LFLEDA-F405L (FEAL) heavy chain | EVKLVESGGGLVQPGGSLRLSCAASGFTFNTYAMNWVRQAPGKGLEWVAR IRSKYNNYATYYADSVKDRFTISRDDSKSSLYLQMNNLKTEDTAMYYCVR HGNFGNSYVSWFAYWGQGTLVTVSSASTKGPSVFPLAPSSKSTSGGTAAL GCLVKDYFPEPVTVSWNSGALTSGVHTFPAVLQSSGLYSLSSVVTVPSSS LGTQTYICNVNHKPSNTKVDKRVEPKSCDKTHTCPPCPAPEFEGGPSVFL FPPKPKDTLMISRTPEVTCVVVAVSHEDPEVKFNWYVDGVE̲V̲H̲NAKTKPR EEQYNSTYRVVSVLTVLHQDWL̲NGKEYKCKVSNKALPAPIEKTISKAKGQ PREPQVYTLPPSREEMTKNQVSLTCLVKGFYPSDIAVEWESNGQPENNYK TTPPVLDSDGSFLLYSKLTVDKSRWQQGNVFSCSVMHEALHNHYTQKSLS LSPG |

TABLE 1-continued

Bold and underlined are FE; A; L and R, corresponding with positions 234 and 235;
265; 405 and 409, respectively, said positions being in accordance with
EU-numbering. In variable regions, said CDR regions that were annotated
in accordance with IMGT definitions are underlined.

| SEQ ID NO: | Clone name | Sequence |
|---|---|---|
| SEQ ID NO: 25 | huCD3 VL + CL light chain | QAVVTQEPSFSVSPGGTVTLTCRSSTGAVTTSNYANWVQQTPGQAFRGLI GGTNKRAPGVPARFSGSLIGDKAALTITGAQADDESIYFCALWYSNLWVF GGGTKLTVLGQPKAAPSVTLFPPSSEELQANKATLVCLISDFYPGAVTVA WKADSSPVKAGVETTTPSKQSNNKYAASSYLSLTPEQWKSHRSYSCQVTH EGSTVEKTVAPTECS |
| SEQ ID NO: 26 | CD20-7D8- LFLEDA-K409R (FEAR) heavy chain | EVQLVESGGGLVQPDRSLRLSCAASGFTFHDYAMHWVRQAPGKGLEWVST ISWNSGTIGYADSVKGRFTISRDNAKNSLYLQMNSLRAEDTALYYCAKDI QYGNYYYGMDVWGQGTTVTVSSASTKGPSVFPLAPSSKSTSGGTAALGCL VKDYFPEPVTVSWNSGALTSGVHTFPAVLQSSGLYSLSSVVTVPSSSLGT QTYICNVNHKPSNTKVDKRVEPKSCDKTHTCPPCPAPEFEGGPSVFLFPP KPKDTLMISRTPEVTCVVVAVSHEDPEVKFNWYVDGVEVHNAKTKPREEQ YNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTP PVLDSDGSFFLYSRLTVDKSRWQQGNVFSCSVMHEALHNHYTQKSLSLSP G |
| SEQ ID NO: 27 | CD20-7D8 VL + CL light chain | EIVLTQSPATLSLSPGERATLSCRASQSVSSYLAWYQQKPGQAPRLLIYD ASNRATGIPARFSGSGSGTDFTLTISSLEPEDFAVYYCQQRSNWPITFGQ GTRLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |

EXAMPLES

DuoBody-CD3×CD20

DuoBody-CD3×CD20 is a bsAb recognizing the T-cell antigen CD3 and the B-cell antigen CD20. DuoBody-CD3×CD20 triggers potent T-cell-mediated killing of CD20-expressing cells. DuoBody-CD3×CD20 has a regular IgG1 structure.

Two parental antibodies, IgG1-CD3-FEAL, a humanized IgG1λ, CD3ε-specific antibody having heavy and light chain sequences as listed in SEQ ID NOs. 24 and 25, respectively, and IgG1-CD20-FEAR, derived from human IgG1K CD20-specific antibody 7D8 having heavy and light chain sequences as listed in SEQ ID NOs. 26 and 27, respectively, were manufactured as separate biological intermediates. Each parental antibody contains one of the complementary mutations in the CH3 domain required for the generation of DuoBody molecules (F405L and K409R, respectively). The parental antibodies comprised three additional mutations in the Fc region (L234F, L235E and D265A; FEA). The parental antibodies were produced in mammalian Chinese hamster ovary (CHO) cell lines using standard suspension cell cultivation and purification technologies. DuoBody-CD3×CD20 was subsequently manufactured by a controlled Fab-arm exchange (cFAE) process (Labrijn et al. 2013, Labrijn et al. 2014, Gramer et al. 2013). The parental antibodies are mixed and subjected to controlled reducing conditions. This leads to separation of the parental antibodies that, under re-oxidation, re-assemble. This way, highly pure preparations of DuoBody-CD3×CD20 (~93-95%) were obtained. After further polishing/purification, final product was obtained, close to 100% pure. The DuoBody-CD3×CD20 concentration was measured by absorbance at 280 nm, using the theoretical extinction coefficient $\varepsilon=1.597$ mL·mg$^{-1}$ cm$^{-1}$. The final product was stored at 4° C. The glycosylation profile of DuoBody-CD3×CD20 indicated that it predominantly contains core-fucosylated N linked bi-antennary glycans with varying degrees of terminal galactose. For the product produced, an international proprietary name was obtained, i.e. epcoritamab.

DuoBody-CD3×CD20 was prepared (5 mg/mL or 60 mg/mL) as a sterile clear colorless to slightly yellow solution supplied as concentrate for solution for subcutaneous (SC) injection. DuoBody-CD3×CD20 contains buffering and tonicifying agents. All excipients (Sodium acetate trihydrate, Acetic acid, Sodium hydroxide, Sorbitol, Polysorbate 80, Water for injection) and amounts thereof in the formulated product were pharmaceutically acceptable for subcutaneous injection products. Appropriate doses were reconstituted to a volume of about 1 mL for subcutaneous injection.

Clinical Trial: Dose Escalation

GCT3013-01 (NCT03625037) is an open-label, 2-part (dose escalation and expansion) trial in patients, human subjects, 18 years or older with a documented CD20+ mature B-cell neoplasm, and relapsed and/or refractory B-cell NHL.

A fixed dose administration approach was selected to simplify dose administration because the number of T-cells, i.e. the effector cells for the function of GEN3013, were not expected to be correlated to weight and/or body surface area of the patients. The EMA Guideline on the Evaluation of Anti-cancer Medicinal Products in Man (EMA, 2012; EMA, 2017) acknowledges that the scientific support for body size-based dosing is weak and recommends modelling and simulation approaches using i.a. PK data to define a dosing strategy. Hence, herein the purpose of the dose escalation part was to establish the maximum tolerated dose (MTD) and/or arrive at a dosing strategy for epcoritamab.

The dose escalation part includes accelerated and standard titration. The initial dose-levels were single-subject cohorts (accelerated titration), with the option to expand the cohort with up to 2 additional subjects for the purpose of obtaining additional pharmacokinetic (PK)/pharmacodynamic and biomarker data. The standard titration part includes standard 3 subject cohorts for dose limiting toxicity (DLT) evaluation, with a minimum of 2 evaluable subjects enrolled if neither experienced Grade ≥2 toxicity during the DLT evaluation period (i.e., the first cycle, 28 days). Dose escalation is based on all available data and with increments not exceeding a half log 10 (3.2-fold) increase in the accelerated titration part and not exceeding 100% (2-fold) increase in the standard titration part.

In the dose escalation part, 61 subjects have currently been treated (Table 2). In the initial cohorts 1-5, subjects were exposed to the full (flat) dose of epcoritamab, preceded by a lower priming dose. In addition to a priming dose, an intermediate dose was introduced with Cohort 6 (1.5 mg) to minimize the widening gap between the priming dose and the continuously escalating full dose, and to reduce the risk and incidence of cytokine release syndrome (CRS). No DLTs have occurred, and doses from 0.004 (priming dose for cohort 1) to 48 mg (full dose for cohorts 11 and 11A) have been reviewed as safe to continue enrollment. The MTD has not been reached.

Planned Cycle 1 doses administered to cohorts of subjects are listed in table 2. For example, in cohort 8 a priming dose of 0.04 mg was administered at day 1, an intermediate dose of 0.5 mg at day 8, followed by full (flat) doses of 6 mg at days 15 and 22, of the first 28 day cycle. Subsequent 28-day cycles, when administered, included in cycle 2, administration of the flat dose at days 1, 8, 15 and 22 of the 28 day cycle, from cycles 3-6, administration of the flat dose at days 1 and 15 of the 28 day cycle and from cycles 7+, administration of the flat dose at day 1 of the 28 day cycle.

TABLE 2

Planned Dosing by Cohort in GCT3013-01

| Cohort | Planned Cycle 1 Doses (Days 1, 8, 15 and 22)[1] (mg) | Number of subjects treated (N = 61) |
|---|---|---|
| 1 | 0.004 mg, 0.0128 mg, 0.0128 mg, 0.0128 mg | 1 |
| 2[2] | 0.0128 mg, 0.04 mg, 0.04 mg, 0.04 mg | 2 |
| 3 | 0.04 mg, 0.12 mg, 0.12 mg, 0.12 mg | 4 |
| 3a | 0.04 mg, 0.38 mg, 0.38 mg, 0.38 mg | 1 |
| 4 | 0.12 mg, 0.38 mg, 0.38 mg, 0.38 mg | 1 |
| 5 | 0.04 mg, 0.76 mg, 0.76 mg, 0.76 mg | 7 |
| 6 | 0.04 mg, 0.250 mg, 1.5 mg, 1.5 mg | 5 |
| 7 | 0.04 mg, 0.5 mg, 3 mg, 3 mg | 6 |
| 8 | 0.04 mg, 0.5 mg, 6 mg, 6 mg | 7 |
| 8a[3] | 0.08 mg, 0.5 mg, 6 mg, 6 mg | 2 |
| 9 | 0.04 mg, 0.8 mg, 12 mg, 12 mg | 3 |
| 9a[3] | 0.08 mg, 1.6 mg, 12 mg, 12 mg | 4 |
| 10 | 0.04 mg, 0.8 mg, 24 mg, 24 mg | 6 |
| 10a[3] | 0.16 mg, 0.8 mg, 24 mg, 24 mg | 4 |
| 11 | 0.08 mg, 0.8 mg, 48 mg, 48 mg | 3 |
| 11a[3] | 0.16 mg, 0.8 mg, 48 mg, 48 mg | 2 |
| 12 | 0.16 mg, 0.8 mg, 60 mg, 60 mg | 3 |

Note:
To bridge the gap between priming and continuously escalating full doses, an intermediate dose of epcoritamab was added prior to dosing at the 1.5 mg full dose level (i.e. from cohort 6 onwards)
[1]The last dose in Cycle 1 is continued in Cycle 2 and onwards
[2]One subject received only the priming dose but is included in the 0.04 mg dose level based on the planned full dose for this subject. The subject was on treatment for 8 days.
[3]Parallel evaluation cohort (i.e., another priming dose was investigated followed by a previously declared safe full dose)

Pre-medication to prevent acute injection reactions consisted of diphenhydramine 50 mg IV or oral (PO) (or equivalent), and paracetamol (acetaminophen) 650 to 1000 mg PO (or equivalent) administered 30-120 minutes prior to epcoritamab administrations during cycle 1. CRS mitigation drug prophylaxis consisted of prednisolone 100 mg IV (or equivalent oral or IV dose of corticosteroid) administered 30-120 minutes prior to epcoritamab administration, followed by additional prednisolone 100 mg IV (or equivalent including oral dose) on the second and third day following epcoritamab administration (i.e. corticosteroid for a total of three consecutive days), for the 1st four doses of epcoritamab in cycle 1. If CRS higher than grade 1 occurs after the 4th epcoritamab administration then prophylaxis administration, with optional premedication continues in Cycle 2 (Day 1, 2, and 3) and beyond.

Neurological symptoms ranging from confusion to fatal cerebral edema have been reported with other compounds or drugs targeting CD3. Hence, in the studies, close monitoring of neurologic symptoms was performed, utilizing the relevant assessment tools initially developed for chimeric antigen receptor T-cell (CAR-T) therapies, the CAR-T-cell-associated toxicity 10-point neurological assessment (CAR-TOX-10) and the American Society for Transplantation and Cellular Therapy (ASCTC) Immune Effector Cell-Associated Neurotoxicity Syndrome (ICANS) Assessment with each dose, at the end of treatment, and when clinically indicated. The drug scheme administered to reduce risk and severity cytokine release-associated ICANS was covered by the CRS prophylaxis scheme, i.e. prednisolone 100 mg IV (or equivalent including oral dose), diphenhydramine 50 mg IV or oral (PO) (or equivalent), and paracetamol (acetaminophen) 650 to 1000 mg PO (or equivalent) on the day of epcoritamab administration, followed by additional prednisolone 100 mg IV (or equivalent including oral dose) on the second and third day following epcoritamab administration (i.e. prednisolone for a total of three consecutive days).

Demographics

Of the various B-cell NHL subtypes enrolled, patients were classified according to WHO 2008 or WHO 2016 guidelines (Swerdlow S H, Campo E, Harris N L, et al. WHO Classification of Tumours of Haematopoietic and Lymphoid Tissues (ed 4th). Lyon, France: IARC Press; 2008; Swerdlow S H, Campo E, Harris N L, et al. WHO Classification of Tumours of Haematopoietic and Lymphoid Tissues (Revised ed 4th). Lyon, France: IARC Press; 2017). Because there is overlap between DLBCL and HGBCL classification between the WHO 2016 and WHO 2008 guidelines, patients diagnosed as DLBCL or HGBCL are defined as one group classified as DLBCL/HGBCL.

Of the 61 patients treated with various B-cell NHL subtypes, 45 (73.8%) had disease classified as DLBCL/HGBCL, and 11 (18.0%) subjects as FL. Other B-cell NHL included were MCL (3 patients), MZL (1 patient) and SLL (1 patient).

Baseline disease characteristics data from 58 patients were available in the clinical database, the majority of patients were Ann Arbor stage III (25.9%) or IV (51.7%) at screening and most had presence of extranodal disease (58.6%). The median time since lymphoma diagnosis was 26.7 mo (range 6-330), and median time since last relapse or progression was 1.6 mo (range 0-88). Most patients were refractory to last line of therapy (67.2%) and/or most recent anti-CD20 therapy (63.8%), and 6.9% had prior CAR T therapy. The median number of prior therapy lines was 3 (range 1-18), most commonly rituximab (100%), alkylating agents (98.3%) and anthracyclines (89.7%); 23 subjects (39.7%) had >3 prior lines of prior therapy.

Clinical Efficacy

The response to treatment was assessed by radiologic imaging at specified timepoints and, when necessary, tissue biopsy, according to both the Lugano criteria (Cheson, et al. (2014). J Clin Oncol 32, 3059-3068), which incorporate metabolic activity on FDG-PET, assessment of size of a limited number of target lesions by CT/MRI, and presence of any new lesions. Patients with FDG-avid tumors at Screening had subsequent disease assessments performed with e.g. FDG-PET-CT using the Deauville 5-point scale (DS) (Barrington, et al. (2014) J Clin Oncol 32, 3048-3058). For patients with non-avid or variably FDG-avid tumors, CT scan with IV contrast of neck/chest/abdomen/pelvis/additional known lesions or in some cases MRI, was performed to evaluate response. Response criteria involved calculating the sum of the product of the perpendicular diameters (SPD) for up to six measurable, dominant lesions and comparing change in this SPD at each subsequent scans, as well as factoring in the appearance of any new lesions. When FDG-PET was implemented, the overall DS was applied according to the target lesion demonstrating the highest uptake. In some cases, tissue biopsy was needed to clarify or confirm the response.

Table 3 presents the best overall response (BOR) for the response-evaluable population (n=53), which includes subjects across all histologies and all doses who have received at least 1 dose of trial drug, and at least 1 post-baseline response assessment or have died as of May 5, 2020. One subject who had coronary artery bypass grafting (CABG) surgery during the study and one subject who had COVID-19 and subsequently died were excluded. The overall response rate (ORR) was 34.0%, and the disease control rate (DCR) was 52.8%.

TABLE 3

Trial GCT3013-01 Best Overall Response, Lugano
Classification by Investigator Assessment.

| Number of Subjects | Response-Evaluable Population | | |
| --- | --- | --- | --- |
| | DLBCL/HGBCL Full dose ≥ 6 mg (N = 19) | FL Full dose ≥ 0.76 mg (N = 8) | Total All dose levels (N = 53)[a] |
| Complete Response (CR), n (%) | 4 (21.1%) | 0 | 7 (13.2%) |
| Partial Response (PR), n (%) | 4 (21.1%) | 7 (87.5%) | 11 (20.8%) |
| Stable Disease (SD), n (%) | 4 (21.1%) | 1 (12.5%) | 10 (18.9%) |
| Progressive Disease (PD), n (%) | 7 (36.8%) | 0 | 25 (47.2%) |
| ORR (CR + PR), n (%) | 8 (42.1%) | 7 (87.5%) | 18 (34.0%) |
| Disease control (CR + PR + SD), n (%): | 12 (63.2%) | 8 (100%) | 28 (52.8%) |

[a]Total number of subjects treated (n = 61). Total number of subjects evaluable (n = 53), as 6 subjects did not have their follow-up assessment as of May 05, 2020, 1 subject had coronary artery bypass grafting (CABG) surgery during the study, and 1 subject had COVID-19 and subsequently died.

Among response-evaluable subjects with R/R DLBCL/HGBCL who received full doses of at least 6.0 mg, 8/19 (42.1%) responded, with 4 (21.1%) achieving CR, 4 (21.1%) achieving PR, and 4 (21.1%) additional subjects achieving SD. Among response-evaluable subjects with FL who received full doses of at least 0.76 mg at the time of data cutoff, 7/8 (87.5%) achieved a PR and 1/8 (12.5%) had SD.

A table listing the maximum reduction in target lesions (i.e, best percent change in SPD of all target lesions) and BOR by investigator for subjects with DLBCL/HGBCL (full dose 6 mg) and FL (full dose 0.76 mg) are listed below.

TABLE 4

Efficacy Results from Dose Escalation Part in GCT3013-01

| Subject ID | B-Cell NHL subtype | Full Dose Level | Last Dosing Visit | Still on Treatment | Best % Change in SPD from Baseline | Best Overall Response | PET Score |
| --- | --- | --- | --- | --- | --- | --- | --- |
| 01 | HGBCL | 6 mg | Cycle 4 Day 15 | No | −40.909 | PR | 4 |
| 02 | DLBCL | 12 mg | Cycle 8 Day 1 | Yes | −100.000 | CR | 1 |
| 03 | DLBCL | 6 mg | Cycle 2 Day 1 | No | 39.175 | PD | 5 |
| 04 | HGBCL | 6 mg | Cycle 3 Day 15 | No | −11.935 | SD | 5 |
| 05 | DLBCL | 48 mg | Cycle 2 Day 8 | Yes | −16.053 | SD | 5 |
| 06 | DLBCL | 24 mg | Cycle 2 Day 1 | No | 127.876 | PD | 5 |
| 07 | DLBCL | 12 mg | Cycle 7 Day 1 | No | −73.898 | CR | 2 |
| 08 | DLBCL | 12 mg | Cycle 1 Day 15 | No | 102.905 | PD | |
| 09 | DLBCL | 12 mg | Cycle 7 Day 1 | Yes | −95.141 | CR | 2 |
| 10 | DLBCL | 6 mg | Cycle 2 Day 1 | No | 101.342 | PD | |
| 11 | DLBCL | 6 mg | Cycle 1 Day 22 | No | −12.039 | SD | 5 |

TABLE 4-continued

| | | | | | | Best % Change in | Best | |
| Subject ID | B-Cell NHL subtype | Full Dose Level | Last Dosing Visit | Still on Treatment | | SPD from Baseline | Overall Response | PET Score |
|---|---|---|---|---|---|---|---|---|
| 12 | DLBCL | 24 mg | Cycle 2 Day 8 | No | | 3.048 | PD | 5 |
| 13 | DLBCL | 48 mg | Cycle 2 Day 15 | Yes | | −57.565 | PR | 5 |
| 14 | DLBCL | 6 mg | Cycle 7 Day 1 | Yes | | −100.000 | CR | 1 |
| 15 | DLBCL | 24 mg | Cycle 2 Day 1 | No | | 69.212 | PD | |
| 16 | DLBCL | 12 mg | Cycle 3 Day 15 | Yes | | −44.007 | SD | |
| 17 | DLBCL | 24 mg | Cycle 2 Day 15 | Yes | | −46.535 | PR | 3 |
| 18 | DLBCL | 24 mg | Cycle 1 Day 22 | Yes | | 122.222 | PD | |
| 19 | DLBCL | 48 mg | Cycle 2 Day 22 | Yes | | −64.86 | PR | 5 |
| 20 | FL | 6 mg | Cycle 6 Day 15 | No | | −78.562 | PR | |
| 21 | FL | 24 mg | Cycle 2 Day 22 | Yes | | −60.772 | PR | 4 |
| 22 | FL | 0.76 mg | Cycle 6 Day 15 | No | | −81.057 | PR | 5 |
| 23 | FL | 12 mg | Cycle 3 Day 15 | Yes | | −7.843 | SD | 5 |
| 24 | FL | 3 mg | Cycle 9 Day 1 | Yes | | −79.093 | PR | |
| 25 | FL | 3 mg | Cycle 8 Day 1 | Yes | | −79.910 | PR | |
| 26 | FL | 3 mg | Cycle 8 Day 1 | No | | −85.478 | PR | |
| 27 | FL | 24 mg | Cycle 6 Day 1 | Yes | | −74.341 | PR | 4 |

Subject ID lists the anonymous patient identifier number.
B-cell NHL subtype includes DLBCL/HGBCL and FL.
Response categories include complete response (CR), partial response (PR), stable disease (SD), and progressive disease (PD), where response was assessed based on comparison of radiologic imaging to baseline scans, including measurement of the SPD of a defined set of representative lesions and appearance of any new lesions, according to the widely-accepted Lugano criteria as described above.
When available, the 5-point PET score from the visit with the best % change in SPD is reported; if there are multiple visits with the same best % change in SPD, the minimum 5-point PET score among these visits is reported.

With regard to patients not classified as DLBCL/HGBCL and FL, the patient with MZL, treated with full dose of 0.76 mg, demonstrated SD on week 8 imaging scan. For MCL, one patient achieved CR, and another patient achieved SD.

In summary, epcoritamab administered subcutaneously demonstrated anti-tumor activity in B-NHL, particularly in DLBCL/HGBCL and FL, during dose escalation, including several responses at very low doses in some patients. The majority of responses (CR, PR) in the DLBCL/HGBCL group were seen at full doses of at least 6 mg, and all responses in the FL group were seen at full doses of at least 0.76 mg.

Clinical Safety

An overview of all treatment-emergent adverse event of all subjects is listed in tables 5A and 5B.

TABLE 5A

Treatment Emergent Adverse Event Summary

| | Full dose Number of Subjects (%) | | | | | |
| | 0.0128 mg (N = 1) | 0.04 mg (N = 2) | 0.12 mg (N = 4) | 0.38 mg (N = 2) | 0.76 mg (N = 7) | 1.5 mg (N = 5) |
|---|---|---|---|---|---|---|
| Number of subjects with at least one TEAE | 1 (100%) | 2 (100%) | 4 (100%) | 2 (100%) | 7 (100%) | 5 (100%) |
| AESI | 0 | 0 | 3 (75.0%) | 0 | 5 (71.4%) | 3 (60.0%) |
| Cytokine Release Syndrome | 0 | 0 | 3 (75.0%) | 0 | 4 (57.1%) | 3 (60.0%) |
| Grade 1 | 0 | 0 | 1 (25.0%) | 0 | 2 (28.6%) | 3 (60.0%) |
| Grade 2 | 0 | 0 | 2 (50.0%) | 0 | 2 (28.6%) | 0 |
| Clinical Tumor Lysis Syndrome | 0 | 0 | 0 | 0 | 0 | 0 |
| Neurological Symptoms | 0 | 0 | 0 | 0 | 1 (14.3%) | 0 |
| AE during DLT period | 1 (100%) | 2 (100%) | 4 (100%) | 2 (100%) | 7 (100%) | 5 (100%) |
| Related* AE | 1 (100%) | 1 (50.0%) | 4 (100%) | 1 (50.0%) | 7 (100%) | 4 (80.0%) |
| AE leading to dose interruption | 1 (100%) | 1 (50.0%) | 0 | 0 | 3 (42.9%) | 1 (20.0%) |
| AE leading to permanent discontinuation of treatment | 0 | 0 | 1 (25.0%) | 1 (50.0%) | 2 (28.6%) | 0 |

TABLE 5A-continued

| | Treatment Emergent Adverse Event Summary | | | | | |
|---|---|---|---|---|---|---|
| | Full dose Number of Subjects (%) | | | | | |
| | 0.0128 mg (N = 1) | 0.04 mg (N = 2) | 0.12 mg (N = 4) | 0.38 mg (N = 2) | 0.76 mg (N = 7) | 1.5 mg (N = 5) |
| Serious AE | 0 | 1 (50.0%) | 3 (75.0%) | 2 (100%) | 5 (71.4%) | 4 (80.0%) |
| Serious related* AE | 0 | 0 | 1 (25.0%) | 0 | 1 (14.3%) | 1 (20.0%) |
| Grade 3/4 AE | 1 (100%) | 1 (50.0%) | 4 (100%) | 1 (50.0%) | 4 (57.1%) | 5 (100%) |
| Fatal AE[a] | 0 | 0 | 1 (25.0%) | 2 (100%) | 2 (28.6%) | 0 |

TABLE 5B

| | Full Dose Number of Subjects (%) | | | | | |
|---|---|---|---|---|---|---|
| | 3 mg (N = 6) | 6 mg (N = 9) | 12 mg (N = 7) | 24 mg (N = 10) | 48 mg (N = 5) | Total (N = 58)[1] |
| Number of subjects with at least one TEAE | 6 (100%) | 9 (100%) | 7 (100%) | 10 (100%) | 5 (100%) | 58 (100%) |
| AESI | 2 (33.3%) | 6 (77.8%) | 6 (85.7%) | 7 (58.3%) | 3 (60.0%) | 35 (60.3%) |
| Cytokine Release Syndrome | 2 (33.3%) | 6 (77.8%) | 5 (71.4%) | 7 (58.3%) | 3 (60.0%) | 33 (56.9%) |
| Grade 1 | 0 | 4 (%) | 2 (28.6%) | 4 (33.3%) | 1 (20.0%) | 17 (29.3%) |
| Grade 2 | 2 (33.3%) | 2 (22.2%) | 3 (42.9%) | 3 (25.0%) | 2 (40.0%) | 16 (27.6%) |
| Clinical Tumor Lysis Syndrome | 0 | 0 | 0 | 0 | 0 | 0 |
| Neurological Symptoms | 0 | 0 | 2 (28.6) | 1 (33.3%) | 0 | 4 (6.9%) |
| AE during DLT period | 6 (100%) | 9 (100%) | 7 (100%) | 10 (100%) | 5 (100%) | 58 (100%) |
| Related* AE | 6 (100%) | 9 (100%) | 7 (100%) | 9 (90.0%) | 5 (100%) | 54 (93.1%) |
| AE leading to dose interruption | 4 (66.7%) | 3 (33.3%) | 0 | 2 (20.0%) | 2 (40.0%) | 19 (32.8%) |
| AE leading to permanent discontinuation of treatment | 1 (16.7%) | 1 (11.1%) | 0 | 0 | 0 | 7 (12.1%) |
| Serious AE | 4 (66.7%) | 7 (77.8%) | 1 (14.3%) | 6 (60.0%) | 4 (80.0%) | 39 (67.2%) |
| Serious related* AE | 1 (16.7%) | 4 (44.4%) | 0 | 5 (50.0%) | 3 (60.0%) | 18 (31.0%) |
| Grade 3/4 AE | 3 (50.0%) | 7 (77.8%) | 3 (42.9%) | 4 (40.0%) | 4 (80.0%) | 40 (69.0%) |
| Fatal AE[2] | 2 (33.3%) | 1 (11.1%) | 0 | 1 (10.0%) | 1 (20.0%) | 11 (19.0%) |

Safety dataset from GCT3013-01 dose escalation, listing TEAE observed.

Note:

Multiple adverse events with same AE are only counted once for each subject.

Percentages are based on N, the number of subjects, per cohort or total.

Related* = (possibly) related including AEs with missing relationship.

[1]Data for the 3 patients in cohort 12 (full dose 60 mg) were not included in the above safety analysis. All 3 patients in cohort 12 have received 1-2 doses at 60 mg, and no adverse events were reported following the 60 mg doses.

[2]Fatal AEs were due to disease progression/euthanasia and were not treatment-related.

Of the 58 subjects evaluated in the safety analysis, 58 (100%) subjects experienced at least 1 treatment-emergent adverse event (TEAE); 69.0% of the subjects had grade 3 or grade 4 TEAEs (tables 5A and 5B). The 4 most common TEAEs were pyrexia (69.0%), CRS (56.9%), fatigue (41.4%), and injection site reaction (41.4%). Eleven (19.0%) subjects had TEAEs leading to death, 9 (15.5%) subjects with malignant neoplasm progression (progression of lymphoma) and 1 (1.7%) due to "euthanasia," (also in the context of progressive disease). One (1.7%) patient died from Coronavirus infection (COVID-19) None of these events were considered related to epcoritamab.

Serious adverse events (SAEs) were reported in 39 (67.2%) subjects. The most frequently reported SAEs were pyrexia (25.9%), malignant neoplasm progression (15.5%), and lung infection (6.9%).

The occurrence of TEAEs leading to permanent treatment discontinuation was limited to 7 subjects (12.1%), and all of these involved disease progression. Five (8.6%) subjects had reported events of malignant neoplasm progression, 1 (1.7%) subject experienced partial seizures (in the context of possible CNS involvement with lymphoma), and 1 (1.7%) subject experienced dyspnea due to underlying disease.

Adverse events of special interest (AESIs) occurred in 35 (60.3%) of the subjects; of these, 33 (56.9%) subjects experienced grade 1 or grade 2 CRS; no patients discontinued treatment due to CRS. Four (6.9%) subjects experienced neurotoxicity (1 [1.7%] subject [0.76 mg] experienced grade 1 partial seizures; 1 [1.7%] subject [12 mg] had grade 1 agraphia related to CRS; 1 [1.7%] subject [12 mg] had grade 3 confusional state related to CRS; 1 [1.7%] subject [12 mg] had grade 3 confusion in the setting of influenza and leptomeningeal disease).

In summary, treatment was well tolerated with doses administered up to and including 60 mg. No dose limiting toxicities were observed and thus a maximum tolerated dose was not reached. There were no severe (grade 3 or higher) CRS events and no treatment-related deaths.

Evaluation of Clinical Response and Mechanism of Action

Pharmacodynamic (PD) biomarkers were also studied to evaluate clinical responses to epcoritamab and mechanism of action (MOA). Biomarker analyses were conducted using peripheral blood to evaluate the effects of epcoritamab on circulating immune cells and cytokines using flow cytometry and immunoassays, respectively. Epcoritamab induced a rapid and sustained depletion of circulating B cells (if present at baseline after prior anti-CD20 therapy). A transient decrease in peripheral CD4+ and CD8+ T cells was observed within 6 hrs of first dose and subsequent dosing induced expansion of both CD8+ and CD4+ T cells from baseline. Additionally, activation markers CD69 and CD279 were upregulated on CD4+ and CD8+ T cells. Exploratory analysis of biomarkers associated with clinical response indicated a trend for greater expansion of activated and total T cells (both CD8+ and CD4+) and higher IFNγ levels in patients who had a partial or complete response to epcoritamab.

Step-up dosing and SC administration of epcoritamab during dose escalation were implemented to mitigate CRS. Moderate elevations of CRS related cytokines, IL-6 and TNF, were observed. These PD biomarker changes in T cells and cytokines were consistently observed across different B-NHL classifications. Additional biomarker analyses are ongoing and updated data will be presented.

The mechanism of action of epcoritamab involves targeting the T-cell surface antigen CD3 and the B-cell surface antigen CD20, triggering T-cell-mediated killing of CD20 positive cells. DuoBody-CD3×CD20 was shown to induce T-cell activation and expansion leading to potent T-cell-mediated cytotoxicity towards malignant B cells, and observed data are consistent with the mechanism of action confirming the clinical activity of epcoritamab for the treatment of B-NHL.

Modelling

As the number of patients assessed in our clinical trial per cohort group were small, we resorted to analyzing patient data in modelling approaches in order to arrive at an optimal subcutaneous dose for epcoritamab in the treatment of DLBCL and FL.

Plasma epcoritamab concentration vs time pharmacokinetics (PK) data was available from patients treated from 0.0128 mg to the 48 mg full dose. A population PK model was developed, using the available PK data and Monolix population PK modelling software (MonolixSuite), for subcutaneous administration of epcoritamab. A one compartment model with first order absorption, linear and michaelis-menten elimination was determined to be the model that best describe the PK data.

Based on a population PK model, epcoritamab exhibits slow absorption with Tmax of 2.96 (48.7%) days (geometric mean and CV). Model predicts the terminal half-life of epcoritamab to be 9.58 (112%) days (geometric mean and CV). Of note, s.c. administrated epcoritamab exhibits flip-flop kinetics where absorption rate is slower than elimination rate. As such, the terminal half-life is representative of absorption half-life and is independent of dose. At the full dose of 48 mg, the Cmax at steady state is 3.30E6 (75.0%) µg/mL (geometric mean and CV). Population PK analysis showed epcoritamab exhibits target-mediated drug disposition (TMDD). Simulation using the population PK model showed saturation of target-mediated drug disposition (>90%) occurred at dose levels >12 mg, indicating engagement and saturation of CD3 and CD20 in plasma (See FIG. 1).

However, engagement and saturation of target in plasma, as predicted by the population PK model, is not most relevant for efficacy assessment. Engagement and saturation at the site of action (near tumor) is more relevant. In addition, for a bispecific antibody, saturation of the two targets occurs sequentially, with the higher affinity targeting arm (CD20) reaching saturation first, followed by lower affinity targeting arm (CD3). Formation of trimer (cross-linking of the CD3 and CD20 by bispecific antibody) increases as concentration of bispecific antibody approaches the KD value of the CD20 arm. Trimer concentration eventually reaches a plateau as bispecific antibody concentration increases beyond KD value of the CD20 arm. Following the plateau, trimer concentration starts to decline once bispecific antibody concentration exceed the KD value of CD3 arm. Therefore, the maximum trimer formation occurs before complete saturation of CD3 and CD20. Hence, there is an optimal range at which the bispecific antibody will achieve maximal trimer formation, and in turn maximal efficacy.

In order to quantitatively predict trimer formation in a tumor, a semi-mechanistic model was developed. Initially, a semi-mechanistic PK/PD model was developed using pre-clinical monkey data. Investigation of epcoritamab in monkey generated rich data, including a range of doses (spanning 3 order of magnitudes, single dose and multiple dose) administrated i.v. and s.c., intensive PK data, blood T-cell count over time data, blood B-cell count over time data, as well as activated T-cell subset count over time data.

The developed model makes use of a minimal physiological based PK model (mPBPK) to provide physiologically relevant prediction of epcoritamab concentration in tissue. The model also takes into consideration trafficking of T-cell and B-cell from blood to tissue and back, the dynamic production and death of T/B cell, as well as feedback mechanism that maintains T/B cell homeostasis. The model incorporates binding of epcoritamab (in blood and in tissue) to CD3 on T-cell and CD20 on B-cell as well as crosslinking of CD3 and CD20, based on measured KD values for CD3 and CD20. The model links the formation of trimer to activation of T-cells, followed by expansion of T-cells. The activated T-cell then induces elimination of B-cell. The developed PK/PD model was fitted to PK, T-cell count, activated T-cell count, and B-cell count data simultaneously, using a population-based modeling approach and Monolix software.

The PK/PD model was able to describe to PK/PD data (plasma concentration, blood T-cell count, blood activated T-cell count and blood B-cell count data) reasonably well, based on model diagnostics such as observed vs. predicted, residual vs. predicted, and residual vs. time, model parameter estimate precision.

Next, an integrated human PK/PD model was subsequently developed based on the structure of the PK/PD model developed based on the monkey data. An overview of human PK/PD modeling analysis is shown in FIG. 2. The model leverages both non-clinical and clinical PK and efficacy data, to predict trimer formation and efficacy. Monolix software was used for fitting of model (both population PK model and monkey PK/PD model). Simulation were done using R (Microsoft) with the mrgsolve package. The model incorporates mPBPK model to predict epcoritamab concentration in tumor lesion. The model also incorporates T-cell, B-cell, and tumor cell count, as well as expression of CD3 and CD20 on these cells. In addition, the model incorporates dynamic binding of epcoritamab to CD3 and CD20 as well as formation of trimer. Finally, the PK/PD model incorporates tumor dynamics and tumor killing as a result of trimer formation and T-cell activation.

The human PK/PD model makes use of some relevant parameters estimated by the monkey PK/PD model. Human PK/PD model parameters were based on available clinical data or human specific values from literature. PK sub-model parameters were informed by fitting the mPBPK model to clinical PK data. Trimer formation sub-model parameters were based on patient biomarker data (e.g. T-cell count, B-cell count, tumor cell count), in vitro measurements (e.g. epcoritamab KD for CD3 and CD20 (16 and 5.4 nM, respectively), and/or literature values (e.g. CD3 expression on T-cell, CD20 expression on B-cell/tumor cell). The tumor dynamic sub-model parameters were based on literature values (e.g. tumor growth rate), patient tumor size data (e.g. baseline tumor size), or estimated by calibrating human PK/PD model predicted response rate to observed response rate from epcoritamab dose escalation trial (e.g. tumor killing rate). The calibrated model described the response rate (based on changes in lesion size) observed in the epcoritamab dose escalation trial well (FIG. 3), and as such the model is validated for in silico analysis to predict optimal dosing.

Hence, clinical trial simulations were subsequently performed using the integrated human PK/PD model, incorporating individual variability in key model parameters. Variability in model parameters are based on either observed inter-individual variability from epcoritamab dose escalation trial (e.g. T-Cell, B-Cell, and baseline tumor size, PK parameters) or based on literature value (eg, CD3, CD20 expression, tumor growth rate). Separate simulations were conducted for FL and DLBCL/HGBCL, distinguished by different tumor growth rate. For DLBCL/HGBCL a tumor doubling time of 1 month was used while for FL a tumor double time of 6 month was used.

The human PK/PD model (FIGS. 4 and 5) showed trimer formation plateaus at epcoritamab doses ≥48 mg in both FL and DLBCL/HGBCL. In addition, the PK/PD model predicts plateauing of efficacy (predicted expansion trial response rate) occurring at epcoritamab dose ≥48 mg (FIGS. 6 and 7) in both FL and DLBCL/HGBCL. Based on model prediction, an optimal dose of epcoritamab that can be selected is 48 mg, utilizing available clinical data from patients.

Further Analysis I

Following up the results presented above, patients continued to be assessed and/or receive treatment, and also further patients were treated with epcoritamab.

At this later time point of assessment, the total number of patients enrolled was 67, which included 45 patients (67%) with diffuse large B-cell lymphoma (DLBCL), 12 (18%) with follicular lymphoma (FL) and 4 (6%) with mantle cell lymphoma (MCL). Patients were heavily pretreated, with a median (range) of 3 (1-6) prior lines of therapy for patients with DLBCL, and 4.5 (1-18) for patients with FL, and 4 (3-5) for patients with MCL; in total 6 patients had received prior CAR-T therapy. Over half of patients (37/67; 55%) were refractory to their most recent systemic therapy and 35/67 (52%) were refractory to their most recent anti-CD20 mAb therapy.

At a median overall follow-up of 8.3 months, treatment is ongoing in 25 patients (37%). Median follow-up is 8.3 months for patients with DLBCL and 8.8 months for patients with FL. Epcoritamab was well tolerated and there were no discontinuations due to treatment-related adverse events (AEs). The most common treatment-emergent AEs (TEAEs) were pyrexia (70%), local injection-site reactions (48%) and fatigue (45%). With increased doses, TEAEs of special interest were consistent with previous reports: CRS events were all grade 1/2 (58%) with no grade 3/4 events and limited neurotoxicity was observed (6%; grade 1:3%; grade 3:3%; all transient).

There were no dose-limiting toxicities, tumor lysis syndrome, or febrile neutropenia events, and no deaths due to treatment-related AEs. Anti-tumor activity in evaluable patients with DLBCL and FL is shown in the Table 6. In 18 patients with DLBCL receiving epcoritamab ≥12 mg, overall response rate (ORR) was 66.7% with 6 patients achieving a complete response (CR). Of the 7 patients who received epcoritamab ≥48 mg (48 mg RP2D n=4; 60 mg n=3), all achieved a response, including CR in 2 patients. All patients with DLBCL who were previously treated with CAR-T therapy achieved a response (4/4: 2 CR; 2 partial response [PR]). Among all 8 patients with FL receiving epcoritamab ≥0.76 mg, ORR was 100%, with 2 patients achieving a CR.

TABLE 6

| Anti-tumor activity of epcoritamab in evaluable patients with R/R B-NHL | | | | |
|---|---|---|---|---|
| | DLBCL | | FL | |
| | ≥12 mg | ≥48 mg | ≥0.76 mg | ≥12 mg |
| Evaluable patients | 18[a] | 7 | 8 | 3 |
| Overall response rate, % | 66.7 | 100 | 100 | 100 |
| Complete response, n (%) | 6 (33.3) | 2 (28.6) | 2 (25.0) | 2 (66.7) |
| Partial response, n (%) | 6 (33.3) | 5 (71.4) | 6 (75.0)[b] | 1 (33.3) |
| Stable disease, n (%) | 1 (5.6) | 0 | 0 | 0 |
| Progressive disease, n (%) | 5 (27.8) | 0 | 0 | 0 |

Based on data snapshot. Response assessments were based on Lugano 2014 response criteria by investigator assessment (modified response evaluable population).
[a]Excludes 1 patient with COVID-19.
[b]Only 4 patients had PET scans (not mandatory until recent protocol amendment)

Furthermore, a total 4 patients with MCL received treatment with epcoritamab, one patient (blastoid; at 6 mg) died after rapid disease deterioration one week after receiving the priming dose (C1D1), one patient (at 12 mg) yielded SD at week 6 assessment, but PD at week 12, one patient (blastoid, at 48 mg) yielded PR at week 6 assessment but PD at week 12, and one patient (pleomorphic; priming dose 0.16 mg, intermediate dose 0.8 mg, 24 mg) yielded deep structural and metabolic CR at week 6 assessment, which was sustained at the most recent response assessment (Week 24: SPD=0 cm$^2$; DS=1). Three out of four patients with MCL experienced six CRS events during cycle 1, which were all grade 1 (i.e. fever as only finding) and resolved within 48 hrs of onset (#1, priming dose 40 µg, intermediate dose, full dose 6 mg, 1 episode of CRS within 24 hrs after priming dose; #2, priming dose 0.16 mg, intermediate dose 0.8 mg, full dose 24 mg, 2 episodes of CRS: first episode 4 days after priming dose, another episode 4 days after intermediate dose; #3 priming dose 0.16 mg, intermediate dose 0.8 mg, full dose 48 mg, 3 episodes of CRS: first episode within 24 hrs after priming dose, another 3 days after intermediate dose, and a third episode 24 hrs after 1st full dose). None of the CRS events led to delay of planned next epcoritamab administration, change of epcoritamab dose or discontinuation from the study. To conclude, epcoritamab demonstrated activity and good tolerability in MCL.

These results show that epcoritamab continues to demonstrate a favorable safety profile, with no grade ≥3 CRS events and limited neurotoxicity, in support of outpatient administration. The results show substantial single-agent efficacy, including complete responses in heavily pretreated patients with FL, MCL, and DLBCL.

In addition to assessing safety and efficacy parameters, further data was collected from patients (including patients receiving epcoritamab in the range from 0.0128-60 mg) for further PK/PD analysis. This further data analysis indicated that epcoritamab exhibited slow absorption, with a Tmax of 2.8 days, and a terminal half-life of 8.67 days, and target-mediated disposition (TMD). Like shown above, the model predicts the saturation of TMD to occur at dose levels ≥48 mg, indicating engagement and saturation of CD3 and CD20 in blood. Furthermore, the model was able to describe the exposure-response relationship observed in the clinic and clinical trial simulations using the PK/PD model demonstrated again that a 48-mg dose can achieve optimal trimer formation and clinical response in both FL and DLBCL. An exposure-adverse event analysis showed a flat relationship between epcoritamab exposure and risk of cytokine release syndrome (CRS) in the dose range evaluated.

Further Analysis II

In another further follow up from the results presented above, patients continued to be assessed and/or received treatment with epcoritamab.

At this later time point of assessment, the total number of patients enrolled was 68, which included 46 patients (68%) with diffuse large B-cell lymphoma (DLBCL), 12 (18%) with follicular lymphoma (FL) and 4 (6%) with mantle cell lymphoma (MCL). Patients were heavily pretreated, with a median (range) of 3 (1-6) prior lines of therapy for patients with DLBCL, and 4.5 (1-18) for patients with FL, and 4 (3-5) for patients with MCL; in total 6 (9%) patients had received prior CAR-T therapy. The majority of patients (59/68; 87%) were refractory to their most recent systemic therapy and 60/68 (88%) were refractory to their most recent anti-CD20 mAb therapy.

At a median duration of follow-up of 10 months, treatment is ongoing in 17 patients (25%). Median duration of follow-up is 7 months for patients with DLBCL and 12 months for patients with FL. With doses administered up to 60 mg, no dose-limiting toxicities were observed and the maximum tolerated dose was not reached. Epcoritamab was well tolerated and there were no discontinuations due to treatment-related adverse events (AEs). The most common treatment-emergent AEs (TEAEs) were pyrexia (69%), local injection-site reactions (47%) and fatigue (43%). The majority of adverse events were grade 1-2. With increased doses, TEAEs of special interest were consistent with previous reports: CRS events were all grade 1/2 (59%) with no grade 3/4 events (see table 7), and limited neurotoxicity was observed (6%; grade 1:3%; grade 3:3%; all transient with median [range] of 1.5 [<1-3] days and manageable with standard therapy). There was one patient with tumor lysis syndrome, grade 3 related to disease progression.

It was observed that most CRS events occurred in cycle 1, with no CRS event with the second full dose at 48 mg. The majority of events occurred and resolved in cycle 1. The median time (range) to resolution was 2 (1.0-9.0) days. Despite dose escalating to the recommended dosing of 48 mg, and also 60 mg, no CRS events were of grade 3 or higher. The risk of CRS was mitigated by the route of administration, step-up dosing, and pretreatment with corticosteroids.

TABLE 7

| Adverse events related to CRS | |
| --- | --- |
| Adverse events of special interest | All histologies (N = 68) |
| CRS, n (%) | 40 (59) |
| Grade 1 | 20 (29) |
| Grade 2 | 20 (29) |
| Symptoms of CRS ≥10%, n (%) | |
| Pyrexia | 40 (59) |
| Hypotension | 16 (24) |
| Hypoxia | 12 (18) |
| Tachycardia | 10 (15) |
| Chills | 7 (10) |

Anti-tumor activity in evaluable patients with DLBCL, FL and MCL is shown in the Table 8. In 22 patients with DLBCL receiving epcoritamab 12-60 mg, overall response rate (ORR) was 68% with 10 patients achieving a complete response (CR). Of the 11 DLBCL patients who received epcoritamab 48-60 mg (48 mg RP2D n=8; 60 mg n=3), 10 patients achieved a response, including CR in 6 patients. All patients with DLBCL who were previously treated with CAR-T therapy and response-evaluable achieved a response (4/4: 2 CR; 2 partial response [PR]). Among all 10 patients with FL receiving epcoritamab 0.76-48 mg, ORR was 90%, with 5 patients achieving a CR. Of the 5 patients with FL who received epcoritamab 12-48 mg, ORR was 80%, with 3 patients achieving a CR.

No further patients with MCL received treatment with epcoritamab. Briefly, of the four patients, one patient (blastoid; at 6 mg) died without response assessment one week after receiving the priming dose (C1D1) after presumed rapid disease deterioration, one patient (at 12 mg) yielded SD at week 6 assessment, but PD at week 12, one patient (blastoid, at 48 mg) yielded PR at week 6 assessment but PD at week 12, and one patient (pleomorphic; priming dose 0.16 mg, intermediate dose 0.8 mg, 24 mg) yielded deep structural and metabolic CR at week 6 assessment, which was sustained at most recent response assessment (Week 24: SPD=0 cm2; DS=1).

TABLE 8

Anti-tumor activity of epcoritamab in evaluable patients with R/R B-NHL

| Response* | DLBCL (n = 46) | | FL (n = 12) | | MCL[‡] |
| --- | --- | --- | --- | --- | --- |
| | 12-60 mg (n = 23) | 48-60 mg[†] (n = 12) | 0.76-48 mg (n = 11) | 12-48 mg (n = 5) | 0.76-48 mg(n = 4) |
| Evaluable patients, n | 22[§] | 11[§] | 10[‖] | 5 | 4** |
| ORR, n (%)[¶] | 15 (68) | 10 (91) | 9 (90)[††] | 4 (80) | 2 (50) |
| CR | 10 (46) | 6 (55) | 5 (50) | 3 (60) | 1 (25) |
| PR | 5 (23) | 4 (36) | 4 (40) | 1 (20) | 1 (25) |
| Stable disease, n (%) | 1 (5) | 0 | 0 | 0 | 1 (25) |
| Progressive disease, n (%) | 5 (23) | 0 | 1 (10) | 1 (20) | 0 |

*Response assessments were based on Lugano 2014 response criteria by investigator assessment (modified response-evaluable population).
[†]Includes 3 patients who received 60-mg dose before RP2D was determined.
[‡]3 patient had blastoid/pleomorphic MCL; 1 had unknown histology.
[§]Excludes 1 patient who discontinued before first assessment due to COVID-19.
[‖]Excludes 1 patient who discontinued before first assessment due to post cardiac (CABG) surgery.
[¶]Response rates are based on number of evaluable patients (defined as patients with at least 1 post-baseline disease assessment or who died without a post-baseline disease assessment).
**Includes 1 patient who died before response assessment.
[††]6/10 patients had response evaluation by PET scans (not mandatory until recent protocol amendment)

With regard to the PK/PD model as described above, this was continuously updated with further data obtained from patients. Results obtained were highly similar to e.g. the results depicted in FIGS. 1 and 3-7. The overall conclusions remained the same, for both FL and DLBCL predicted trimer formation was plateauing from 48-192 mg, and the predicted response rate started to plateau at 48 mg. An exposure—adverse event analysis was also performed indicating that there was an overall low risk of grade 2 CRS, with priming, intermediate and full dose, and a flat relationship between epcoritamab Cmax and grade 2 CRS. Based on the model and clinical trial simulations, the 48 mg full dose was identified as the biological efficacious dose, resulting in adequate target modulation and clinical activity weighed against the risk of adverse events.

CONCLUSIONS

Based on the favorable safety profile, combined with impressive efficacy profile with high response rates, including complete responses, epcoritamab has the potential to be best-in-class treatment at least for patients with relapsed or refractory DLBCL/HGBCL, FL and MCL. These data support future outpatient administration of epcoritamab. Based on clinical efficacy, safety data and PK/PD modelling, a recommended full dose can be at least 48 mg for both DLBCL/HGBCL and FL, and for B-NHL in general. Based on currently available data, a full dose of 60 mg can be contemplated. A full dose of 48 mg can be recommended. Safety data observed on the priming dose of 0.16 mg and the intermediate dose of 0.80 mg, together with the observation that all CRS events following these doses were of only mild-moderate (≤gr. 2) severity and were resolved with standard CRS management, indicates a priming dose and intermediate dose of 0.16 mg and 0.80 mg, respectively, can be recommended. Hence, cycle 1 can be recommended to comprise at days 1, 8, 15 and 22 of the 28-day cycle, the administration of 0.16 mg, 0.80 mg, 48 mg and 48 mg, respectively. Also, the cycles administered after cycle 1 can be recommended to include in cycles 2-3, administration of the full dose at days 1, 8, 15 and 22 of the 28-day cycle, from cycles 4-9, administration of the full dose at days 1 and 15 of the 28-day cycle and from cycles 10 and onwards administration of the full dose at day 1 of the 28-day cycle. Prophylaxis and premedication for CRS mitigation as outlined herein can be recommended from 3 to 4 consecutive days for all four weekly doses in cycle 1 and continued when CRS>gr. 1 is noted after the fourth weekly epcoritamab administration in cycle 1. Currently clinical trials are utilizing this dosing regimen with a recommended 48 mg full dose and expanding in i.a. FL, MCL and DLBCL/HGBCL, and a phase III trial has been initiated in relapsed, refractory DLBCL having failed or ineligible for HDT-ASCT.

Dose escalation and expansion part and phase III trial In total, 169 subjects have been treated across 3 ongoing trials of epcoritamab: GCT3013-01 (n=153 subjects total; 68 subjects in the dose escalation part, 85 subjects in the expansion part), GCT3013-04 (n=14 subjects; 7 subjects in the dose escalation part, 7 subjects in the expansion part), and GCT3013-05 (n=2 subjects).

GCT3013-01 is a phase I/II Open-Label trial investigating the safety and preliminary efficacy of epcoritamab in subjects with relapsed, progressive or refractory B-cell lymphoma. Patients have been treated in the dose escalation part, results thereof have been extensively described above. Further updates to the results as described above are provided below. Following up dose escalation, in the expansion part patients receive treatment with epcoritamab subcutaneously in 28-day cycles, within cycle 1, day 1, 0.16 mg, day 8 0.8 mg, days 15 and 22, 48 mg; cycles 2-3, day 1, 8, 15 and 22, 48 mg; cycles 4-9, day 1, 15, 48 mg; and cycles 10+, 48 mg on day 1. 153 subjects have been enrolled in this trial.

GCT3013-05 is a randomized open label phase III clinical trial of epcoritamab, in which the first patients have been treated. Patients enrolled are subjects with R/R DLBCL who failed a previous ASCT or are ineligible for ASCT at screening. Efficacy is compared with standard of care treatment, which involves R-GemOx, which is rituximab combined with gemcitabine and oxaliplatin; and rituximab combined with bendamustine. Epcoritamab is administered subcutaneously in 28-day cycles, within cycle 1, day 1, 0.16 mg, day 8 0.8 mg, days 15 and 22, 48 mg; cycles 2-3, day 1, 8, 15 and 22, 48 mg; cycles 4-9, day 1 and 15, 48 mg; and cycles 10+, 48 mg on day 1. 2 subjects have been enrolled in this trial.

GCT3013-04 is a phase I/II Open-Label trial cohort investigating the safety and preliminary efficacy of epcoritamab in Japanese Subjects with relapsed or refractory (R/R) B-NHL. Patients have been treated in the dose escalation and expansion parts, wherein patients receive treatment with epcoritamab subcutaneously in 28-day cycles, with in cycle 1; day 1, 0.16 mg, day 8 0.8 mg, days 15 and 22, 48 mg; cycles 2-3, day 1, 8, 15 and 22, 48 mg; cycles 4-9, day 1 and 15, 48 mg; and cycles 10+, 48 mg on day 1. 14 subjects have been enrolled in this trial.

TABLE 9

| Doses by Cohort - GCT3013-01 Dose Escalation Part | | |
|---|---|---|
| Cohort | Cycle 1 Doses (Days 1, 8, 15, and 22) | Number of Subjects (N = 68) |
| 1 | 0.004 mg, 0.0128 mg, 0.0128 mg, 0.0128 mg | 1 |
| 2 [a] | 0.0128 mg, 0.04 mg, 0.04 mg, 0.04 mg | 2 |
| 3 | 0.04 mg, 0.12 mg, 0.12 mg, 0.12 mg | 4 |
| 3 [b] | 0.04 mg, 0.38 mg, 0.38 mg, 0.38 mg | 1 |
| 4 | 0.12 mg, 0.38 mg, 0.38 mg, 0.38 mg | 1 |
| 5 | 0.04 mg, 0.76 mg, 0.76 mg, 0.76 mg | 7 |
| 6 | 0.04 mg, 0.25 mg, 1.5 mg, 1.5 mg | 5 |
| 7 | 0.04 mg, 0.5 mg, 3 mg, 3 mg | 6 |
| 8 | 0.04 mg, 0.5 mg, 6 mg, 6 mg | 7 |
| 8 [b] | 0.08 mg, 0.5 mg, 6 mg, 6 mg | 2 |
| 9 | 0.04 mg, 0.8 mg, 12 mg, 12 mg | 3 |
| 9 [b] | 0.08 mg, 1.6 mg, 12 mg, 12 mg | 4 |
| 10 | 0.04 mg, 0.8 mg, 24 mg, 24 mg | 6 |
| 10 [b] | 0.16 mg, 0.8 mg, 24 mg, 24 mg | 4 |
| 11 | 0.08 mg, 0.8 mg, 48 mg, 48 mg | 3 |
| 11 [b] | 0.16 mg, 0.8 mg, 48 mg, 48 mg | 9 |
| 12 | 0.16 mg, 0.8 mg, 60 mg, 60 mg | 3 |

Note:
To bridge the gap between priming and continuously escalating full doses, an intermediate dose of epcoritamab was added prior to dosing at the 1.5 mg full dose level. The last dose in Cycle 1 (ie, full dose) is continued in Cycle 2 and onwards.
[a] One subject in Cohort 2 received only the priming dose due to discontinuation (disease progression) from the trial prior tocompletion of the dose-limiting toxicity period (ie, 28 days) and was replaced.
[b] Cohort intended for parallel evaluation.

68 subjects have been treated with epcoritamab in the GCT3013-01 dose escalation part, including 15 subjects (22.1%) who, at the time of data cutoff, were continuing to receive epcoritamab in the 3 to 60 mg dosing groups (2 subjects at 3 mg, 1 subject at 6 mg, 2 subjects at 12 mg, 4 subjects at 24 mg, 4 subjects at 48 mg, and 2 subjects at 60 mg). Of the 53 subjects who had discontinued treatment, 46 subjects discontinued due to disease progression. Of the 68 subjects treated in the GCT3013-01 dose escalation part, the median age was 67.5 years, and the majority of subjects (45, 66.2%) were male. The median time from lymphoma diagnosis to first dose was 29.7 months. The median time since the most recent recurrence, relapse, or progression was 1.6 months. Of the various B-NHL subtypes enrolled, 46 subjects (67.6%) had DLBCL, and 12 subjects (17.6%) had FL. Patients enrolled had the following disease type: Diffuse large B-cell lymphoma, i.e. de novo (28), transformed (17) or unknown (1); high-grade B-cell lymphoma (3), primary mediastinal large B-cell lymphoma (1), follicular lymphoma (12), mantle-cell lymphoma (4), small lymphocytic lymphoma (1) and marginal zone lymphoma (1). Patients receiving the full dose included diffuse large B-cell lymphoma, i.e. de novo (9), Primary mediastinal large B-cell lymphoma (1), Follicular lymphoma (1), and Mantle-cell lymphoma (1).

85 subjects have been treated with epcoritamab in the GCT3013-01 expansion part, including 61 subjects (71.8%) who are continuing to receive epcoritamab at the time of data cutoff; 50 subjects were continuing in the aggressive B-cell non-Hodgkin lymphoma (aNHL) cohort and 11 subjects were in the indolent B-cell non-Hodgkin lymphoma (iNHL) cohort. Of the 24 subjects (28.2%) who discontinued treatment, 14 subjects discontinued due to disease progression. Of the 85 subjects treated in the GCT3013-01 expansion part, the median age was 68.0 years, and the majority of subjects (60, 70.6%) were male. The median time from lymphoma diagnosis to first dose was 24.9 months. The median time since the most recent refractory or relapse was 1.13 months. Of the various B-NHL subtypes enrolled, 71 (83.5%) subjects had DLBCL, and 13 (15.3%) subjects had FL. In the aggressive NHL cohort, most subjects had DLBCL, i.e. de novo (44), transformed (17), not applicable (5), unknown (3), missing (1); and one patient had high-grade B-cell lymphoma. Of the subjects in the indolent B-cell non-Hodgkin lymphoma cohort, 12 had follicular lymphoma grade 1-3A and one of unknown grade.

TABLE 10

| Subject Disposition - GCT3013-01 Expansion Part | | | |
|---|---|---|---|
| | Cohort | | |
| Number (%) of subjects[a] | aNHL | iNHL | Total |
| Full Analysis set (FAS) | 72 (100%) | 13 (100%) | 85 (100%) |
| Safety set | 72 (100%) | 13 (100%) | 85 (100%) |
| Treated subjects | | | |
| Ongoing trial treatment | 50 (69.4%) | 11 (84.6%) | 61 (71.8%) |
| Discontinued from trial treatment | 22 (30.6%) | 2 (15.4%) | 24 (28.2%) |
| Progressive disease[b] | 12 (16.7%) | 2 (15.4%) | 14 (16.5%) |
| Adverse event | 4 (5.6%) | 0 | 4 (4.7%) |
| Withdrawal by subject | 1 (1.4%) | 0 | 1 (1.2%) |
| Death | 1 (1.4%) | 0 | 1 (1.2%) |
| Other | 1 (1.4%) | 0 | 1 (1.2%) |
| Missing | 3 (4.2%) | 0 | 3 (3.5%) |
| Discontinued from trial | 11 (15.3%) | 1 (7.7%) | 12 (14.1%) |
| Death | 7 (9.7%) | 1 (7.7%) | 8 (9.4%) |
| Lost to follow-up | 0 | 0 | 0 |
| Withdrawal by subject | 1 (1.4%) | 0 | 1 (1.2%) |
| Other | 2 (2.8%) | 0 | 2 (2.4%) |
| Missing | 1 (1.4%) | 0 | 1 (1.2%) |

Note:
Percentages calculated based on number of subjects in FAS.
aNHL = aggressive B-cell non-Hodgkin lymphoma; FAS = Full Analysis set; iNHL = indolent B-cell non-Hodgkin lymphoma.
[a] FAS and safety set include all subjects exposed to epcoritamab.
[b] Progressive disease includes both clinical progression and documented radiographic disease progression.

Pharmacodynamics

Epcoritamab induced rapid and sustained depletion of circulating B-cells (in the subset of patients with detectable B-cells, which are absent in most subjects due to prior anti-CD20 therapy). B-cells were detected with an antibody against CD19. Subsequent dosing induced expansion of circulating T-cells from baseline and moderate elevations of circulating IFNγ, IL-6, and TNFα (by serum immunoassay) at doses greater than 12 mg. Transient decrease in peripheral CD4+ and CD8+ T-cells was observed within 6 hours of first SC dose, which is consistent with T-cell margination seen with other bispecifics. Importantly, subsequent dosing induced expansion of T-cells from baseline. Step-up dosing and SC administration of epcoritamab were implemented to mitigate CRS. SC administration of epcoritamab resulted in moderate IFNγ, IL-6, and TNFα elevations.

Efficacy

In the dose escalation part, evaluations of response to treatment were based on investigator assessments according to Lugano criteria (Cheson et al., 2014). Using the Full Analysis set, 18/46 subjects (39.1%) with DLBCL achieved a response (subjects with partial response or complete response are considered as responders). In subjects with FL, 9/12 (75.0%) achieved a response (Table 11).

Safety and Tolerability

All 68 subjects in the GCT3013-01 dose escalation part had experienced at least 1 treatment-emergent adverse event (TEAE). The 4 most common TEAEs were pyrexia (69.1%), CRS (58.8%), injection site reaction (47.1%), and fatigue (44.1%). In total, 80.9% of subjects had at least one grade 3 or higher TEAE. There were 13 subjects with TEAEs leading to death (11 subjects with malignant neoplasm

TABLE 11

Best Overall Response by Disease, Lugano Classification by Investigator Assessment—GCT3013-01 Dose Escalation Part—DLBCL and FL Subjects

| Number (%) of Subjects | Full Dose | | | | | | | | |
|---|---|---|---|---|---|---|---|---|---|
| | <0.76 mg | ≥0.76 mg | <12 mg | ≥12 mg | 12 mg | 24 mg | 48 mg | 48-60 mg | Total |
| Diffuse large B-cell lymphoma | | | | | | | | | |
| Best overall response | N = 7 | N = 39 | N = 23 | N = 23 | N = 5 | N = 6 | N = 9 | N = 12 | N = 46 |
| Complete response (CR) | 1 (14.3%) | 12 (30.8%) | 3 (13.0%) | 10 (43.5%) | 3 (60.0%) | 1 (16.7%) | 3 (33.3%) | 6 (50.0%) | 13 (28.3%) |
| Partial response (PR) | 0 | 5 (12.8%) | 0 | 5 (21.7%) | 1 (20.0%) | 0 | 4 (44.4%) | 4 (33.3%) | 5 (10.9%) |
| Stable disease (SD) | 0 | 4 (10.3%) | 3 (13.0%) | 1 (4.3%) | 0 | 1 (16.7%) | 0 | 0 | 4 (8.7%) |
| Progressive disease | 6 (85.7%) | 16 (41.0%) | 17 (73.9%) | 5 (21.7%) | 1 (20.0%) | 4 (66.7%) | 0 | 0 | 22 (47.8%) |
| Not evaluable | 0 | 0 | 0 | 0 | 0 | 0 | 0 | 0 | 0 |
| No assessments[a] | 0 | 2 (5.1%) | 0 | 2 (8.7%) | 0 | 0 | 2 (22.2%) | 2 (16.7%) | 2 (4.3%) |
| Overall response rate (CR + PR) (95% CI)[b] | 1 (14.3%) (0.4%, 57.9%) | 17 (43.6%) (27.8%, 60.4%) | 3 (13.0%) (2.8%, 33.6%) | 15 (65.2%) (42.7%, 83.6%) | 4 (80.0%) (28.4%, 99.5%) | 1 (16.7%) (0.4%, 64.1%) | 7 (77.8%) (40.0%, 97.2%) | 10 (83.3%) (51.6%, 97.9%) | 18 (39.1%) (25.1%, 54.6%) |
| Complete response rate (95% CI)[b] | 1 (14.3%) (0.4%, 57.9%) | 12 (30.8%) (17.0%, 47.6%) | 3 (13.0%) (2.8%, 33.6%) | 10 (43.5%) (23.2%, 65.5%) | 3 (60.0%) (14.7%, 94.7%) | 1 (16.7%) (0.4%, 64.1%) | 3 (33.3%) (7.5%, 70.1%) | 6 (50.0%) (21.1%, 78.9%) | 13 (28.3%) (16.0%, 43.5%) |
| Disease control rate (CR + PR + SD) (95% CI)[b] | 1 (14.3%) (0.4%, 57.9%) | 21 (53.8%) (37.2%, 69.9%) | 6 (26.1%) (10.2%, 48.4%) | 16 (69.6%) (47.1%, 86.8%) | 4 (80.0%) (28.4%, 99.5%) | 2 (33.3%) (4.3%, 77.7%) | 7 (77.8%) (40.0%, 97.2%) | 10 (83.3%) (51.6%, 97.9%) | 22 (47.8%) (32.9%, 63.1%) |
| Follicular lymphoma | | | | | | | | | |
| Best overall response | N = 1 | N = 11 | N = 7 | N = 5 | N = 1 | N = 3 | N = 1 | N = 1 | N = 12 |
| Complete response (CR) | 0 | 5 (45.5%) | 2 (28.6%) | 3 (60.0%) | 1 (100%) | 2 (66.7%) | 0 | 0 | 5 (41.7%) |
| Partial response (PR) | 0 | 4 (36.4%) | 3 (42.9%) | 1 (20.0%) | 0 | 1 (33.3%) | 0 | 0 | 4 (33.3%) |
| Stable disease (SD) | 1 (100%) | 0 | 1 (14.3%) | 0 | 0 | 0 | 0 | 0 | 1 (8.3%) |
| Progressive disease | 0 | 2 (18.2%) | 1 (14.3%) | 1 (20.0%) | 0 | 0 | 1 (100%) | 1 (100%) | 2 (16.7%) |
| Not evaluable | 0 | 0 | 0 | 0 | 0 | 0 | 0 | 0 | 0 |
| No assessments[a] | 0 | 0 | 0 | 0 | 0 | 0 | 0 | 0 | 0 |
| Overall response rate (CR + PR) (95% CI)[b] | 0 (0.0%, 97.5%) | 9 (81.8%) (48.2%, 97.7%) | 5 (71.4%) (29.0%, 96.3%) | 4 (80.0%) (28.4%, 99.5%) | 1 (100%) (2.5%, 100%) | 3 (100%) (29.2%, 100%) | 0 (0.0%, 97.5%) | 0 (0.0%, 97.5%) | 9 (75.0%) (42.8%, 94.5%) |
| Complete response rate (95% CI)[b] | 0 (0.0%, 97.5%) | 5 (45.5%) (16.7%, 76.6%) | 2 (28.6%) (3.7%, 71.0%) | 3 (60.0%) (14.7%, 94.7%) | 1 (100%) (2.5%, 100%) | 2 (66.7%) (9.4%, 99.2%) | 0 (0.0%, 97.5%) | 0 (0.0%, 97.5%) | 5 (41.7%) (15.2%, 72.3%) |
| Disease control rate (CR + PR + SD) (95% CI)[b] | 1 (100%) (2.5%, 100%) | 9 (81.8%) (48.2%, 97.7%) | 6 (85.7%) (42.1%, 99.6%) | 4 (80.0%) (28.4%, 99.5%) | 1 (100%) (2.5%, 100%) | 3 (100%) (29.2%, 100%) | 0 (0.0%, 97.5%) | 0 (0.0%, 97.5%) | 10 (83.3%) (51.6%, 97.9%) |

Full Analysis set for DLBCL and FL subjects. Of the 4 subjects enrolled with mantle-cell lymphoma, 2 responded (1 CR, 1 PR). The remaining subjects had other B-cell non-Hodgkin lymphoma histologies.
[a]Subjects died without any post-baseline assessment.
[b]Based on the Clopper and Pearson method.

57 progression, 1 with euthanasia [also in the context of progressive disease], and 1 with COVID-19 [coronavirus disease 2019] pneumonia). None was considered related to epcoritamab. Serious adverse events (SAEs) were reported for 46 subjects (67.6%) of subjects. The most common SAE considered related to trial drug was pyrexia (19 subjects, 27.9%), which was reported as a symptom of CRS (see Section 4.6.2.2). The occurrence of TEAEs leading to permanent treatment discontinuation was low (13.2% of subjects). Adverse events of special interest (AESIs) included the following: 40 subjects (58.8%) experienced CRS, 4 subjects (5.9%) experienced neurological symptoms considered by the investigator to be immune mediated, and 1 subject (1.5%) experienced clinical tumor lysis syndrome. AESIs were captured on a separate AESI page in the eCRF. Symptoms relating to the AESI that met the seriousness criteria were reported as SAEs with the overall diagnosis as the main event. 46 of the 68 subjects (67.6%) treated in the GCT3013-01 dose escalation part had experienced at least 1 SAE. A total of 24 subjects (35.3%) experienced SAEs that were considered related to epcoritamab. The most common SAE considered related to trial drug was pyrexia (19 subjects, 27.9%), which was reported as a symptom of CRS.

76 of the 85 subjects (89.4%) in the GCT3013-01 expansion part had experienced at least 1 TEAE (Table 12). The 3 most common TEAEs were CRS (47.1%), fatigue (18.8%), and pyrexia (18.8%) (Table 13). In total, 40.0% of subjects had at least one grade 3 or higher TEAE (Table 14). There were 7 subjects with TEAEs leading to death. One subject experienced a TEAE leading to death that was considered related to epcoritamab by the investigator (immune effector cell-associated neurotoxicity syndrome [ICANS]). SAEs were reported for 55.3% of subjects. The most common SAE considered related to trial drug was CRS (25 subjects, 29.4%). The occurrence of TEAEs leading to permanent treatment discontinuation was low (5.9% of subjects). AESIs included the following: 40 subjects (47.1%) experienced CRS, 3 subjects (3.5%) experienced ICANS, and 1 subject (1.2%) experienced clinical tumor lysis syndrome.

As said, 7 of the 85 subjects (8.2%) treated in the GCT3013-01 expansion part had experienced TEAEs leading to death. The one subject experienced a TEAE leading to death that was considered related to epcoritamab by the investigator. This subject was a 72-year-old female with stage IV non-GCB DLBCL and medical history of diabetes, hypertension, hyperlipidemia, as well as right upper lobectomy due to lung cancer. At screening, the subject had pancreatic, splenic, and para-aortic lymphoma involvement. The subject experienced continuous abdominal pain 2 days after priming dose of 0.16 mg of epcoritamab and was later diagnosed with grade 3 pancreatitis, treated with multiple repeated doses of morphine, and progressive lymphoma was determined based on imaging. Four days after intermediate dose 0.8 mg of epcoritamab, grade 2 ICANS was reported, which later worsened to grade 4. In addition, grade 1 cerebral ischemia was observed at brain imaging. The study drug was withdrawn. The subject's condition deteriorated and the subject expired 17 days after intermediate dose 0.8 mg of epcoritamab, with death reported to be due to ICANS. However, metabolic encephalopathy caused by hyperammonemia in a subject with long history of diabetes, hypertension, hyperlipidemia, possible microangiopathy (suggested by new multifocal cerebral infarcts, splenic infarct, laboratory evidence of coagulopathy, and renal dysfunction), as well as an accumulation of active metabolites of morphine use (which are dependent on functioning kidneys for clearance), are very likely confounding factors for the neurotoxicity. Unwarranted administration of tocilizumab to treat neurologic symptoms in the absence of CRS is known to increase the potential for neurotoxicity by increasing the circulating levels of IL-6, and likely contributed to the worsening of neurotoxicity in this case.

TABLE 12

Summary of Treatment-Emergent Adverse Events - GCT3013-01 Expansion Part

| | Cohort | | |
| | aNHL (N = 72) | iNHL (N = 13) | Total (N = 85) |
|---|---|---|---|
| Number (%) of subjects with at least 1 | | | |
| TEAE | 64 (88.9%) | 12 (92.3%) | 76 (89.4%) |
| Related TEAE | 47 (65.3%) | 10 (76.9%) | 57 (67.1%) |
| Grade 3 and higher TEAE | 28 (38.9%) | 6 (46.2%) | 34 (40.0%) |
| Grade 3 and higher related TEAE | 11 (15.3%) | 1 (7.7%) | 12 (14.1%) |
| TEAE by worst toxicity grade | | | |
| Grade 1 | 19 (26.4%) | 5 (38.5%) | 24 (28.2%) |
| Grade 2 | 16 (22.2%) | 1 (7.7%) | 17 (20.0%) |
| Grade 3 | 17 (23.6%) | 5 (38.5%) | 22 (25.9%) |
| Grade 4 | 5 (6.9%) | 0 | 5 (5.9%) |
| Grade 5 | 6 (8.3%) | 1 (7.7%) | 7 (8.2%) |
| Missing | 1 (1.4%) | 0 | 1 (1.2%) |
| Serious TEAE | 40 (55.6%) | 7 (53.8%) | 47 (55.3%) |
| Serious related TEAE | 23 (31.9%) | 5 (38.5%) | 28 (32.9%) |
| TEAE leading to treatment discontinuation | 5 (6.9%) | 0 | 5 (5.9%) |
| TEAE leading to dose modification | 16 (22.2%) | 4 (30.8%) | 20 (23.5%) |
| Fatal TEAE | 6 (8.3%) | 1 (7.7%) | 7 (8.2%) |
| Adverse event of special interest | | | |
| Cytokine release syndrome | 33 (45.8%) | 7 (53.8%) | 40 (47.1%) |
| ICANS | 3 (4.2%) | 0 | 3 (3.5%) |
| Clinical tumor lysis syndrome | 1 (1.4%) | 0 | 1 (1.2%) |

Note:
Percentages calculated based on number of subjects in the safety set.
Adverse events are classified using the Medical Dictionary for Regulatory Activities (MedDRA) v23.1 and Common Terminology Criteria for Adverse Events (CTCAE) v5.0, and are counted only once per category. Cytokine release syndrome is graded per (Lee et al., 2019), and clinical tumor lysis syndrome according to Cairo-Bishop (Coiffier et al., 2008).
aNHL = aggressive B-cell non-Hodgkin lymphoma; ICANS = immune effector cell-associated neurotoxicity syndrome; iNHL = indolent B-cell non-Hodgkin lymphoma; TEAE = treatment-emergent adverse event.

TABLE 13

Treatment-Emergent Adverse Events Occurring in >10% of Subjects - GCT3013-01 Expansion Part

| Preferred Term | Total (N = 85) n (%) |
|---|---|
| Cytokine release syndrome | 40 (47.1%) |
| Fatigue | 16 (18.8%) |
| Pyrexia | 16 (18.8%) |
| Anaemia | 13 (15.3%) |
| Nausea | 12 (14.1%) |
| Injection site reaction | 11 (12.9%) |
| Thrombocytopenia | 11 (12.9%) |
| Abdominal pain | 9 (10.6%) |
| Diarrhoea | 9 (10.6%) |
| Dyspnoea | 9 (10.6%) |

Note:
Percentages calculated based on number of subjects in the Safety Set. Adverse events are classified using the Medical Dictionary for Regulatory Activities (MedDRA) v23.1 and are counted at most one time per preferred term.

TABLE 14

Treatment-Emergent Adverse Events of Grade 3 or Higher, by System Organ Class and Preferred Term - GCT3013-01 Expansion Part

| System Organ Class Preferred Term | Cohort | | |
|---|---|---|---|
| | aNHL (N = 72) | iNHL (N = 13) | Total (N = 85) |
| Number (%) of subjects with at least onegrade 3 or higher TEAE | 28 (38.9%) | 6 (46.2%) | 34 (40.0%) |
| Blood and lymphatic system disorders | 8 (11.1%) | 4 (30.8%) | 12 (14.1%) |
| Anaemia | 3 (4.2%) | 1 (7.7%) | 4 (4.7%) |
| Neutropenia | 3 (4.2%) | 1 (7.7%) | 4 (4.7%) |
| Thrombocytopenia | 2 (2.8%) | 1 (7.7%) | 3 (3.5%) |
| Febrile neutropenia | 2 (2.8%) | 0 | 2 (2.4%) |
| Lymphopenia | 2 (2.8%) | 0 | 2 (2.4%) |
| Lymph node pain | 0 | 1 (7.7%) | 1 (1.2%) |
| Infections and infestations | 7 (9.7%) | 1 (7.7%) | 8 (9.4%) |
| COVID-19 | 2 (2.8%) | 0 | 2 (2.4%) |
| Septic shock | 2 (2.8%) | 0 | 2 (2.4%) |
| Cellulitis | 1 (1.4%) | 0 | 1 (1.2%) |
| Infectious pleural effusion | 0 | 1 (7.7%) | 1 (1.2%) |
| Pyelonephritis | 1 (1.4%) | 0 | 1 (1.2%) |
| Respiratory tract infection | 1 (1.4%) | 0 | 1 (1.2%) |
| Investigations | 8 (11.1%) | 0 | 8 (9.4%) |
| Neutrophil count decreased | 5 (6.9%) | 0 | 5 (5.9%) |
| Blood lactate dehydrogenase increased | 1 (1.4%) | 0 | 1 (1.2%) |
| C-reactive protein increased | 1 (1.4%) | 0 | 1 (1.2%) |
| Platelet count decreased | 1 (1.4%) | 0 | 1 (1.2%) |
| Transaminases increased | 1 (1.4%) | 0 | 1 (1.2%) |
| General disorders and administration site conditions | 5 (6.9%) | 1 (7.7%) | 6 (7.1%) |
| Fatigue | 2 (2.8%) | 0 | 2 (2.4%) |
| Disease progression | 1 (1.4%) | 0 | 1 (1.2%) |
| General physical health deterioration | 0 | 1 (7.7%) | 1 (1.2%) |
| Generalised oedema | 1 (1.4%) | 0 | 1 (1.2%) |
| Malaise | 1 (1.4%) | 0 | 1 (1.2%) |
| Pyrexia | 1 (1.4%) | 0 | 1 (1.2%) |
| Respiratory, thoracic and mediastinal disorders | 5 (6.9%) | 0 | 5 (5.9%) |
| Dyspnoea | 2 (2.8%) | 0 | 2 (2.4%) |
| Pleural effusion | 2 (2.8%) | 0 | 2 (2.4%) |
| Respiratory failure | 1 (1.4%) | 0 | 1 (1.2%) |
| Neoplasms benign, malignant and unspecified (incl cysts and polyps) | 3 (4.2%) | 0 | 3 (3.5%) |
| Lung neoplasm | 1 (1.4%) | 0 | 1 (1.2%) |
| Malignant neoplasm progression | 1 (1.4%) | 0 | 1 (1.2%) |
| Tumour pain | 1 (1.4%) | 0 | 1 (1.2%) |
| Vascular disorders | 3 (4.2%) | 0 | 3 (3.5%) |
| Hypotension | 2 (2.8%) | 0 | 2 (2.4%) |
| Hypertension | 1 (1.4%) | 0 | 1 (1.2%) |
| Cardiac disorders | 1 (1.4%) | 1 (7.7%) | 2 (2.4%) |
| Atrial fibrillation | 0 | 1 (7.7%) | 1 (1.2%) |
| Cardiac failure | 1 (1.4%) | 0 | 1 (1.2%) |
| Gastrointestinal disorders | 1 (1.4%) | 1 (7.7%) | 2 (2.4%) |
| Abdominal pain | 0 | 1 (7.7%) | 1 (1.2%) |
| Pancreatitis | 1 (1.4%) | 0 | 1 (1.2%) |
| Immune system disorders | 2 (2.8%) | 0 | 2 (2.4%) |
| Cytokine release syndrome | 2 (2.8%) | 0 | 2 (2.4%) |
| Metabolism and nutrition disorders | 1 (1.4%) | 1 (7.7%) | 2 (2.4%) |
| Hyperglycaemia | 0 | 1 (7.7%) | 1 (1.2%) |
| Metabolic acidosis | 1 (1.4%) | 0 | 1 (1.2%) |
| Tumour lysis syndrome | 1 (1.4%) | 0 | 1 (1.2%) |
| Musculoskeletal and connective tissue disorders | 2 (2.8%) | 0 | 2 (2.4%) |
| Fistula | 1 (1.4%) | 0 | 1 (1.2%) |
| Musculoskeletal chest pain | 1 (1.4%) | 0 | 1 (1.2%) |
| Nervous system disorders | 2 (2.8%) | 0 | 2 (2.4%) |
| Immune effector cell-associated neurotoxicity syndrome | 1 (1.4%) | 0 | 1 (1.2%) |
| Spinal cord compression | 1 (1.4%) | 0 | 1 (1.2%) |

TABLE 14-continued

Treatment-Emergent Adverse Events of Grade 3 or Higher, by System Organ Class and Preferred Term - GCT3013-01 Expansion Part

| System Organ Class Preferred Term | Cohort | | |
|---|---|---|---|
| | aNHL (N = 72) | iNHL (N = 13) | Total (N = 85) |
| Endocrine disorders | 1 (1.4%) | 0 | 1 (1.2%) |
| Adrenal insufficiency | 1 (1.4%) | 0 | 1 (1.2%) |
| Hepatobiliary disorders | 1 (1.4%) | 0 | 1 (1.2%) |
| Hepatotoxicity | 1 (1.4%) | 0 | 1 (1.2%) |
| Hyperbilirubinaemia | 1 (1.4%) | 0 | 1 (1.2%) |
| Skin and subcutaneous tissue disorders | 1 (1.4%) | 0 | 1 (1.2%) |
| Skin lesion | 1 (1.4%) | 0 | 1 (1.2%) |

Note:

Percentages calculated based on number of subjects in the safety set. Adverse events are classified using the Medical Dictionary for Regulatory Activities (MedDRA) v23.1 and Common Terminology Criteria for Adverse Events (CTCAE) v5.0 and are counted at most one time per system organ class and at most one time per preferred term.
aNHL = aggressive B-cell non-Hodgkin lymphoma; COVID-19 = coronavirus disease 2019; iNHL = indolent B-cell non-Hodgkin lymphoma; TEAE = treatment-emergent adverse event.

47 of the 85 subjects (55.30%) treated in the GCT3013-01 expansion part had experienced at least 1 SAE (Table 23). A total of 28 subjects (32.9%) experienced SAEs considered related to epcoritamab. The most common SAE considered related to trial drug was CRS (25 subjects, 29.40%) (Table 15).

TABLE 15

Serious Treatment-Emergent Adverse Events Considered Related to Epcoritamab, by System Organ Class and Preferred Term - GCT3013-01 Expansion Part

| System Organ Class Preferred Term | Cohort | | |
|---|---|---|---|
| | aNHL (N = 72) | iNHL (N = 13) | Total (N = 85) |
| Number (%) of subjects with at least 1 serious related TEAE | 23 (31.9%) | 5 (38.5%) | 28 (32.9%) |
| Immune system disorders | 21 (29.2%) | 4 (30.8%) | 25 (29.4%) |
| Cytokine release syndrome | 21 (29.2%) | 4 (30.8%) | 25 (29.4%) |
| Neoplasms benign, malignant and unspecified (incl cysts and polyps) | 1 (1.4%) | 1 (7.7%) | 2 (2.4%) |
| Tumour flare | 1 (1.4%) | 1 (7.7%) | 2 (2.4%) |
| Respiratory, thoracic and mediastinal disorders | 2 (2.8%) | 0 | 2 (2.4%) |
| Dyspnoea | 1 (1.4%) | 0 | 1 (1.2%) |
| Pleural effusion | 1 (1.4%) | 0 | 1 (1.2%) |
| Endocrine disorders | 1 (1.4%) | 0 | 1 (1.2%) |
| Adrenal insufficiency | 1 (1.4%) | 0 | 1 (1.2%) |
| Gastrointestinal disorders | 1 (1.4%) | 0 | 1 (1.2%) |
| Pancreatitis | 1 (1.4%) | 0 | 1 (1.2%) |
| Investigations | 1 (1.4%) | 0 | 1 (1.2%) |
| C-reactive protein increased | 1 (1.4%) | 0 | 1 (1.2%) |
| Nervous system disorders | 1 (1.4%) | 0 | 1 (1.2%) |
| Immune effector cell-associated neurotoxicity syndrome | 1 (1.4%) | 0 | 1 (1.2%) |
| Vascular disorders | 1 (1.4%) | 0 | 1 (1.2%) |
| Hypotension | 1 (1.4%) | 0 | 1 (1.2%) |

Note:

Percentages calculated based on number of subjects in the safety set. Adverse events are classified using the Medical Dictionary for Regulatory Activities (MedDRA) v23.1 and are counted at most one time per system organ class and at most one time per preferred term.
aNHL = aggressive B-cell non-Hodgkin lymphoma; iNHL = indolent B-cell non-Hodgkin lymphoma; TEAE = treatment-emergent adverse event.

A total of 5 of the 85 subjects (5.9%) treated in the GCT3013-01 expansion part had experienced TEAEs leading to permanent discontinuation of trial drug: 1 subject each experienced lung neoplasm, malignant neoplasm progression, abdominal pain, hepatotoxicity, hyperbilirubinemia, progressive multifocal leukoencephalopathy, increased transaminases, immune effector cell-associated neurotoxicity syndrome, and respiratory failure (Table 16). Two subjects experienced multiple TEAEs leading to permanent discontinuation of treatment: one subject experienced lung neoplasm and respiratory failure; one subject experienced abdominal pain, hepatotoxicity, hyperbilirubinemia, and increased transaminases due to disease progression.

TABLE 16

Treatment-Emergent Adverse Events Leading to Permanent Discontinuation of Treatment, by System Organ Class and Preferred Term - GCT3013-01 Expansion Part.

| System Organ Class Preferred Term | Cohort | | |
| --- | --- | --- | --- |
| | aNHL (N = 72) | iNHL (N = 13) | Total (N = 85) |
| Number (%) of subjects with at least 1 TEAE leading to permanent treatment discontinuation | 5 (6.9%) | 0 | 5 (5.9%) |
| Neoplasms benign, malignant and unspecified (incl cysts and polyps) | 2 (2.8%) | 0 | 2 (2.4%) |
| Lung neoplasm | 1 (1.4%) | 0 | 1 (1.2%) |
| Malignant neoplasm progression | 1 (1.4%) | 0 | 1 (1.2%) |
| Gastrointestinal disorders | 1 (1.4%) | 0 | 1 (1.2%) |
| Abdominal pain | 1 (1.4%) | 0 | 1 (1.2%) |
| Hepatobiliary disorders | 1 (1.4%) | 0 | 1 (1.2%) |
| Hepatotoxicity | 1 (1.4%) | 0 | 1 (1.2%) |
| Hyperbilirubinaemia | 1 (1.4%) | 0 | 1 (1.2%) |
| Infections and infestations | 1 (1.4%) | 0 | 1 (1.2%) |
| Progressive multifocal leukoencephalopathy | 1 (1.4%) | 0 | 1 (1.2%) |
| Investigations | 1 (1.4%) | 0 | 1 (1.2%) |
| Transaminases increased | 1 (1.4%) | 0 | 1 (1.2%) |
| Nervous system disorders | 1 (1.4%) | 0 | 1 (1.2%) |
| Immune effector cell-associated neurotoxicity syndrome | 1 (1.4%) | 0 | 1 (1.2%) |
| Respiratory, thoracic and mediastinal disorders | 1 (1.4%) | 0 | 1 (1.2%) |
| Respiratory failure | 1 (1.4%) | 0 | 1 (1.2%) |

Note:
Percentages calculated based on number of subjects in the safety set. Adverse events are classified using the Medical Dictionary for Regulatory Activities (MedDRA) v23.1 and are counted at most one time per system organ class and at most one time per preferred term.
aNHL = aggressive B-cell non-Hodgkin lymphoma; iNHL = indolent B-cell non-Hodgkin lymphoma; = treatment-emergent adverse event.

Adverse Events of Special Interest

The following is a summary of epcoritamab AESIs:

Cytokine release syndrome, was reported in 86 subjects, including 40 subjects in the GCT3013-01 dose escalation part, 40 subjects in the GCT3013-01 expansion part, and 6 subjects in the GCT3013-04 dose escalation part. CRS was graded according to (Lee et al., 2019). All CRS events were grade 1 or 2, except for 2 events in the GCT3013-01 expansion part and 1 event in the GCT3013-04 dose escalation part that were grade 3.

Neurotoxicity is listed in the epcoritamab protocols as an AESI. In the dose escalation part of GCT3013-01 trial, neurological assessment was conducted according to CARTOX-10 scale (Neelapu et al., 2017). Suspected immune-mediated neurologic symptoms consistent with ICANS were captured as separate AESIs. In the expansion part of the GCT3013-01 trial and the GCT3013-04 trial, the ICANS cases are reported using the exact term of ICANS. Neurological symptoms reported as AESIs were reported in 7 subjects in GCT3013-01, including 4 subjects in the dose escalation part, and 3 subjects in the expansion part, and no subjects in the GCT3013-04 dose escalation part.

Clinical tumor lysis syndrome was reported in 2 subjects, including 1 subject in the GCT3013-01 dose escalation part, 1 subject in the GCT3013-01 expansion part, and no subjects in the GCT3013-04 dose escalation part. Clinical tumor lysis syndrome was graded according to Cairo-Bishop (Coiffier et al., 2008). Both events of tumor lysis syndrome were grade 3.

Summary of Clinical Data

This summarizes data for GCT3013-01 (safety for the dose-escalation and expansion parts, efficacy for the dose escalation part, and PK for the dose escalation part) and safety data for GCT3013-04 dose escalation part. No DLT has occurred, the MTD has not been reached, and the RP2D was declared to be a full dose of 48 mg. All 68 subjects in the GCT3013-01 dose escalation part experienced at least 1 TEAE; 80.9% of subjects had at least one grade 3 or higher TEAE. The most common TEAEs were pyrexia, CRS, injection site reaction, and fatigue. There were 13 subjects with TEAEs leading to death (11 subjects with malignant neoplasm progression, 1 with euthanasia [also in the context of progressive disease], and 1 with COVID-19 pneumonia). SAEs were reported for 67.6% of subjects. The most common SAE considered related to trial drug was pyrexia, which was reported as a symptom of CRS. TEAEs leading to permanent treatment discontinuation were reported in 13.2% of subjects. AESIs included the following: 40 subjects experienced CRS, 4 subjects experienced neurological symptoms considered by the investigator to be immune mediated, and 1 subject experienced clinical tumor lysis syndrome.

A total of 76 subjects (89.4%) in the GCT3013-01 expansion part experienced at least 1 TEAE; 40.0% of subjects had at least one grade 3 or higher TEAE. The most common TEAEs were CRS, fatigue, and pyrexia. There were 7 subjects with TEAEs leading to death (1 subject each with disease progression, general physical health deterioration, COVID-19, hepatotoxicity, malignant neoplasm progression, and immune effector cell-associated neurotoxicity syndrome). SAEs were reported for 55.3% of subjects. The most common SAE considered related to trial drug was CRS. TEAEs leading to permanent treatment discontinuation were reported in 5.9% of subjects. AESIs included the following: 40 subjects experienced CRS, 3 subjects experienced ICANS, and 1 subject experienced clinical tumor lysis syndrome.

All 7 subjects in the GCT3013-04 dose escalation part experienced at least 1 TEAE; 71.4% of subjects had at least one grade 3 or higher TEAE. The most common TEAEs were CRS and injection site erythema. No subjects experienced a TEAE leading to treatment discontinuation, an SAE, or a TEAE leading to death. Two subjects experienced TEAEs leading to dose modification. AESIs of CRS occurred in 6 subjects (85.7%).

Epcoritamab administration induced rapid and sustained depletion of circulating B-cells (in the subset of subjects with detectable B-cells, which are absent in most patients due to prior anti-CD20 therapy) and increases in peripheral T-cells and circulating IFNγ. No significant ADA (titers ≥1) against epcoritamab have been observed in patients. In the GCT3013-01 dose escalation part, for all dose levels combined, the ORR was 44.1%; for the RP2D level (48 mg), the ORR was 66.7%.

Class Effects

Adverse reactions reported for the class of compounds that epcoritamab belongs to, i.e., bispecific T-cell engagers, include CRS, neurological symptoms, and infection.

B-cell depletion may lead to increased risk for infections. Infections should be managed according to best medical practice. Monitoring of latent viral infection, eg, hepatitis B or cytomegalovirus, for subjects at risk should be performed during and after epcoritamab treatment. A total of 58 subjects in the GCT3013-01 trial and GCT3013-04 trial escalation part experienced infections. No epcoritamab-related infections were reported in the GCT3013-01 expansion or GCT3013-04 dose escalation parts.

CRS has been reported with epcoritamab, and other compounds or drugs targeting CD3 and chimeric antigen receptor T-cells. Close monitoring of vital signs, in particular temperature, blood pressure, and oxygen saturation, as well as laboratory assessments of hematology, liver and kidney parameters is important to secure a timely start of supportive care as needed. Supportive care based on (Lee et al., 2019) and (Neelapu et al., 2017) can include, but is not limited to:

Infusion of saline

Systemic glucocorticosteroids, antihistamines, antipyrexia

Support for blood pressure

Support for ventilation

Monoclonal antibody against IL-6R, IL-6, or IL-1 (eg, tocilizumab, siltuximab, and/or anakinra)

Additional CRS risk reducing measures were implemented including prophylactic corticosteroid administration for 4 consecutive days in relation to epcoritamab administration in Cycle 1. The majority of CRS events have been reported as grade 1 and 2; only 3 subjects reported grade 3 CRS.

In total, 86 subjects reported at least 1 CRS event in the GCT3013-01 and GCT3013-04 dose escalation parts. The majority of cases were of grade 1 or grade 2 CRS, whereas grade 3 CRS occurred in only 3 patents, which indicates grade 1 or grade 2 CRS is a very common events, whereas grade 3 appears to be common. Of those, 40 (58.8%) subjects (20 subjects—grade 1; 20 subjects—grade 2) were in the GCT3013-01 dose escalation part, 40 (47.1%) subjects (24 subjects—grade 1; 14 subjects—grade 2; 2 subjects—grade 3) in the GCT3013-01 expansion part, and 6 (85.7%) subjects (4 subjects—grade 1; 1 subject—grade 2; 1 subject—grade 3) in the GCT3013-04 dose escalation part. Out of the 86 subjects who experienced CRS events, 25 were reported as SAEs. All cases of CRS were assessed as related to epcoritamab and recovered/resolved. There were no life-threatening or fatal CRS cases reported. No CRS led to treatment discontinuation.

Neurological symptoms ranging from confusion to fatal cerebral edema have been reported with other compounds or drugs targeting CD3. Neurological assessment should be performed according to ICANS evaluation (Lee et al., 2019). The grading of ICANS requires assessment of the 10-point immune effector cell-associated encephalopathy score as well as evaluation of 4 other neurological domains: level of consciousness, seizures, motor symptoms, and signs of raised intracranial pressure/cerebral edema, which may occur with or without encephalopathy (refer to the protocol). Close monitoring of mental status during treatment is important to secure a timely start of supportive care as needed. Supportive care can include, but is not limited to:

Initiation of IV hydration

Withhold oral intake

Avoid medications that cause central nervous system depression

Initiation of corticosteroids

Anti-cytokine therapy

Anti-convulsive therapy

A total of 7 subjects experienced adverse events related to neurological symptoms (AESIs). Three subjects in the GCT3013-01 expansion part developed ICANS, which was fatal in 1 subject. Four of the 7 subjects were from the GCT3013-01 dose escalation part and experienced 3 serious AESIs of grade 3 depressed level of consciousness, grade 3 hypersomnia, grade 1 partial seizure, and 2 non-serious AESIs of grade 1 dysgraphia and grade 1 agraphia.

The invention claimed is:

1. A method of treating a B-cell non-Hodgkin lymphoma (B-NHL) in a human subject, the method comprising subcutaneously administering a dose of 0.16 mg of epcoritamab to the subject on day one (1) of treatment and subcutaneously administering a dose of 0.8 mg of epcoritamab to the subject on day eight (8) of treatment, wherein the subject does not experience cytokine release syndrome (CRS) or experiences manageable cytokine release syndrome of grade 1 or grade 2, and wherein after day eight (8) of treatment a dose of 48 mg of epcoritamab is subcutaneously administered in intervals to the subject until progressive disease develops or unacceptable toxicity occurs.

2. The method of claim 1, wherein 48 mg of epcoritamab is administered subcutaneously to the human subject on days 15 and 22 of treatment.

3. The method of claim 1, wherein said B-NHL is selected from the group consisting of diffuse large B-cell lymphoma (DLBCL), high-grade B-cell lymphoma (HGBCL), primary mediastinal large B-cell lymphoma (PMBCL), mantle cell lymphoma (MCL), follicular lymphoma (FL), marginal-zone lymphoma (MZL), chronic lymphocytic leukemia (CLL), and small lymphocytic lymphoma (SLL).

4. The method of claim 3, wherein said B-NHL is diffuse large B-cell lymphoma (DLBCL).

5. The method of claim 3, wherein said B-NHL is mantle cell lymphoma (MCL).

6. The method of claim 3, wherein said B-NHL is follicular lymphoma (FL).

7. The method of claim 3, wherein said B-NHL is marginal-zone lymphoma (MZL).

8. The method of claim 3, wherein said B-NHL is small lymphocytic lymphoma (SLL).

9. The method of claim 3, wherein said B-NHL is relapsed or refractory B-NHL.

10. The method of claim 3, wherein said B-NHL is chronic lymphocytic lymphoma (CLL).

11. The method of claim 1, wherein prior to the day 1 of treatment with epcoritamab the human subject has received at least one prior line of treatment for the B-NHL.

12. The method of claim 1, wherein prior to the day 1 of treatment with epcoritamab the human subject has received at least two prior lines of treatment for the B-NHL.

13. The method of claim 2, wherein said B-NHL is selected from the group consisting of diffuse large B-cell lymphoma (DLBCL), high-grade B-cell lymphoma (HGBCL), primary mediastinal large B-cell lymphoma (PMBCL), mantle cell lymphoma (MCL), follicular lymphoma (FL), marginal-zone lymphoma (MZL), chronic lymphocytic leukemia (CLL), and small lymphocytic lymphoma (SLL), and wherein the patient achieves a complete response (CR).

14. The method of claim 13, wherein said B-NHL is diffuse large B-cell lymphoma (DLBCL).

15. The method of claim 13, wherein said B-NHL is mantle cell lymphoma (MCL).

16. The method of claim 13, wherein said B-NHL is follicular lymphoma (FL).

17. The method of claim 13, wherein said B-NHL is marginal-zone lymphoma (MZL).

18. The method of claim 13, wherein said B-NHL is small lymphocytic lymphoma (SLL).

19. The method of claim 13, wherein said B-NHL is relapsed or refractory B-NHL.

20. The method of claim 13, wherein said B-NHL is chronic lymphocytic lymphoma (CLL).

21. A method of treating a B-cell non-Hodgkin lymphoma (B-NHL) in a human subject, the method comprising administering epcoritamab subcutaneously in 28-day cycles, wherein:

a) a priming dose of 0.16 mg is administered on day 1, an intermediate dose of 0.8 mg is administered on day 8, and a full dose of 48 mg is administered on days 15 and 22 of the first cycle;

b) a full dose of 48 mg is administered on days 1, 8, 15 and 22 of cycles 2-3;

c) a full dose of 48 mg is administered on days 1 and 15 of cycles 4-9; and d) a full dose of 48 mg is administered on day 1 of subsequent cycles until progressive disease develops or unacceptable toxicity occurs.

22. The method of claim 21, wherein said B-NHL is selected from the group consisting of diffuse large B-cell lymphoma (DLBCL), high-grade B-cell lymphoma (HGBCL), primary mediastinal large B-cell lymphoma (PMBCL), mantle cell lymphoma (MCL), follicular lymphoma (FL), marginal-zone lymphoma (MZL), chronic lymphocytic leukemia (CLL), and small lymphocytic lymphoma (SLL).

23. The method of claim 22, wherein said B-NHL is diffuse large B-cell lymphoma (DLBCL).

24. The method of claim 22, wherein said B-NHL is mantle cell lymphoma (MCL).

25. The method of claim 22, wherein said B-NHL is follicular lymphoma (FL).

26. The method of claim 22, wherein said B-NHL is marginal-zone lymphoma (MZL).

27. The method of claim 22, wherein said B-NHL is small lymphocytic lymphoma (SLL).

28. The method of claim 22, wherein said B-NHL is relapsed or refractory B-NHL.

29. The method of claim 22, wherein said B-NHL is chronic lymphocytic lymphoma (CLL).

30. The method of claim 21, wherein prior to the day 1 of treatment with epcoritamab the human subject has received at least one prior line of treatment for the B-NHL.

31. The method of claim 21, wherein prior to the day 1 of treatment with epcoritamab the human subject has received at least two prior lines of treatment for the B-NH.

\* \* \* \* \*